(12) United States Patent
Cao

(10) Patent No.: US 8,900,851 B2
(45) Date of Patent: Dec. 2, 2014

(54) MULTI-WELL PLATFORM

(75) Inventor: Jian Cao, South Setauket, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 199 days.

(21) Appl. No.: 13/055,088

(22) PCT Filed: Jul. 20, 2009

(86) PCT No.: PCT/US2009/004184
§ 371 (c)(1),
(2), (4) Date: Apr. 20, 2011

(87) PCT Pub. No.: WO2010/011281
PCT Pub. Date: Jan. 28, 2010

(65) Prior Publication Data
US 2011/0201669 A1    Aug. 18, 2011

Related U.S. Application Data

(60) Provisional application No. 61/082,612, filed on Jul. 22, 2008.

(51) Int. Cl.
| C12M 1/34 | (2006.01) |
| C12Q 1/68 | (2006.01) |
| G01N 33/50 | (2006.01) |
| G01N 33/574 | (2006.01) |

(52) U.S. Cl.
CPC ........ *C12Q 1/6886* (2013.01); *C12Q 2600/112* (2013.01); *C12Q 2600/136* (2013.01); *G01N 2500/00* (2013.01); *C12Q 2600/118* (2013.01); *C12Q 2600/154* (2013.01); *G01N 33/5029* (2013.01); *C12Q 2600/158* (2013.01); *G01N 33/57415* (2013.01)

USPC .............. 435/287.1; 435/288.3; 435/287.8; 435/288.4; 435/305.1; 435/305.2; 435/325; 435/395; 435/397

(58) Field of Classification Search
None
See application file for complete search history.

(56) References Cited

U.S. PATENT DOCUMENTS

| 4,683,195 A | 7/1987 | Mullis et al. ................. 435/6.11 |
| 4,683,202 A | 7/1987 | Mullis .......................... 435/91.2 |

(Continued)

FOREIGN PATENT DOCUMENTS

| WO | WO 2005/012872 | * | 2/2005 |
| WO | WO 2006/074357 | | 7/2006 |

OTHER PUBLICATIONS
Michishita (Cancer Letters. 2006. 239: 71-77.*

(Continued)

*Primary Examiner* — Carla Myers
(74) *Attorney, Agent, or Firm* — Medlen & Carroll, LLP

(57) ABSTRACT

The present invention relates to the diagnosis and treatment of cancer, and in particular breast cancer. Specifically, in some embodiments the invention relates to methods of diagnosing cancer, and in particular breast cancer, using an antibody specific for a gene product that localizes selectively to the endoplasmic reticulum of the cancer cell(s). In some embodiments, the invention relates to methods of treating cancer, and in particular breast cancer, by administering a composition comprising an RNA interference sequence (e.g., shRNA, RNAi and/or siRNA molecule) characterized by an ability to inhibit an mRNA molecule, which mRNA molecule is encoded by the C43 gene (SEQ ID NO: 1). The invention additionally relates to methods for detecting cancer cells by detecting reduced methylation of the C43 promoter, and methods for reducing cancer metastasis by using demethylation inhibitors that result in increased methylation of the C43 promoter. The invention additionally relates to an in vitro 3-dimensional assay for detecting migrating cells, identifying test agents and/or nucleotide sequences that alter cell migration.

7 Claims, 20 Drawing Sheets

(56) References Cited

U.S. PATENT DOCUMENTS

| | | | | |
|---|---|---|---|---|
| 4,965,188 | A | 10/1990 | Mullis et al. | 435/6.12 |
| 5,270,163 | A | 12/1993 | Gold et al. | 435/6.11 |
| 5,736,137 | A | 4/1998 | Anderson et al. | 424/133.1 |
| 5,760,029 | A | 6/1998 | Jadhav et al. | 514/210.16 |
| 7,273,855 | B2 | 9/2007 | Jupe | 514/44 R |
| 7,312,060 | B2 | 12/2007 | Rothschild et al. | 435/194 |
| 2005/0009113 | A1* | 1/2005 | Goldbard et al. | 435/7.2 |
| 2006/0003311 | A1 | 1/2006 | Fulde et al. | 435/4 |
| 2006/0013031 | A1* | 1/2006 | Ravkin et al. | 365/63 |
| 2007/0154928 | A1 | 7/2007 | Mack et al. | 435/6.14 |
| 2007/0178534 | A1* | 8/2007 | Murphy et al. | 435/7.2 |
| 2007/0292901 | A1* | 12/2007 | Costello et al. | 435/7.23 |

OTHER PUBLICATIONS

Blondelle, et al., "Soluble combinatorial libraries of organic, peptidomimetic and peptide-diversities." *Trends Anal. Chem.*, 14:83-92 (1995).

Capdeville, et al., "GLIVEC (STI571, IMATINIB), A Rationally Developed, Targeted Anticancer Drug." *Nat. Rev. Drug Discov.*, 1:493-502 (2002).

Carthew, "Gene silencing by double-stranded RNA." *Curr. Opin. Cell Biol.*, 13(2):244-248 (2001).

Cho, et al., "An Unnatural Biopolymer." *Science*, 261:1303 (1993).

Carrell, et al., "A Novel Procedure for the Synthesis of Libraries Containing Small Organic Molecules." *Angew. Chem. Int. Ed. Engl.*, 33:2059 (1994a).

Carell, et al., "A Solution-Phase Screening Procedure for the Isolation of Active Compounds from a Library of Molecules." *Angew. Chem. Int. Ed. Engl.*, 33:2061 (1994b).

de Kruif, et al., "Biosynthetically lipid-modified human scFv fragments from phage display libraries as targeting molecules for immunoliposomes." *FEBS Lett.*, 399:232-236 (1996).

DeWitt, et al., "Diversomers": An Approach to Nonpeptide, Nonoligomeric Chemical Diversity. *PNAS USA*, 90:6909 (1993).

Dancey, et al., "Strategies for optimizing combinations of molecularly targeted anticancer agents." *Nat. Rev. Drug Discov.*, 5:649-659 (2006).

Debnath, et al., "Modelling glandular epithelial cancers in three-dimensional cultures." *Nature Reviews Cancer*, 5:675-688 (2005).

Ding, et al., "Synthesis and biological activity of oligosaccharide libraries." *Adv. Expt. Med. Biol.*, 376:261-269 (1995).

Ecker and Crook, "Combinatorial drug discovery: Which methods will produce the greatest value?" *Bio/Technology*, 13:351-360 (1995).

Erb, et al., "Recursive deconvolution of combinatorial chemical libraries." *PNAS USA*, 91:11422 (1994).

Gallop, et al., "Applications of combinatorial technologies to drug discovery. 1. Background and peptide combinatorial libraries." *J. Med. Chem.*, 37:1233 (1994).

Gordon, et al., "Applications of combinatorial technologies to drug discovery. 2. Combinatorial organic synthesis, library screening strategies, and future directions." *J. Med. Chem.*, 37:1385-1401 (1994).

Hanahan, et al., "The Hallmarks of Cancer." *Cell*, 100:57-70 (2000).

Karaoglu, et al., "Functional characterization of Ost3p. Loss of the 34-kD subunit of the *Saccharomyces cerevisiae* oligosaccharyltransferase results in biased underglycosylation of acceptor substrates." *J. Cell Biol.*, 130:567-577 (1995).

Kim, et al., "Three-dimensional in vitro tissue culture models of breast cancer-a review." *Breast Cancer Research and Treatment*, 85:281-291 (2004).

Koivunen, et al., "Isolation of a Highly Specific Ligand for the alpha 5 beta 1 Integrin from a Phage Display Library." *J. Cell Biol.*, 124:373-380 (1994).

Kunz-Schughart, et al., "The use of 3-D cultures for high-throughput screening: the multicellular spheroid model." *J Biomol Screen*, 9:273-285 (2004).

Lam, "Application of combinatorial library methods in cancer research and drug discovery." *Anticancer Drug Des.*, 12:145 (1997).

Lang, et al., "Inhibitors for Metastasis Development." *Recent Patents on Anti-Cancer Drug Discovery*, 1:69-80 (2006).

Liang, et al., "Parallel synthesis and screening of a solid phase carbohydrate library." *Science*, 274:1520-1522 (1996).

Matsuzaki, et al., "Clinicopathologic significance of *KIAA1199* overexpression in human gastric cancer." *Ann Surg Oncol.*, 16(7):2042-51 (2009).

Pitot, et al., "*Fundamentals of Oncology*." pp. 15-28 (1978).

Szyf, "Epigenetics, DNA methylation, and chromatin modifying drugs." *Annu. Rev. Pharmacol. Toxicol.*, 49:243-263 (2009).

Thiery, et al., "Epithelial-mesenchymal transitions in tumour progression." *Nat. Rev. Cancer*, 2:442-454 (2002).

Ui-Tei, et al., "Functional dissection of siRNA sequence by systematic DNA substitution: modified siRNA with a DNA seed arm is a powerful tool for mammalian gene silencing with significantly reduced off-target effect." *Nucleic Acids Res.*, 32:936-948 (2008).

Williams, et al., "Therapeutic anticancer efficacy of a synthetic diazonamide analog in the absence of overt toxicity." *PNAS USA*, 104:2074-2079 (2007).

York, et al., "The structures of arabinoxyloglucans produced by solanaceous plants." *Carb. Res.*, 285:99-128 (1996).

Zhang, et al., "A Simple Statistical Parameter for Use in Evaluation and Validation of High Throughput Screening Assays." *J. Biomol. Screen*, 4:67-73 (1999).

Zuckennann, et al., "Discovery of Nanomolar Ligands for 7-Transmembrane G-Protein-Coupled Receptors from a Diverse N-(Substituted)glycine Peptoid Library." *J. Med. Chem.*, 37:2678-85 (1994).

Abe, et al., "Mutations in the gene encoding KIAA1199 protein, an inner-ear protein expressed in Deiters' cells and the fibrocytes, as the cause of nonsyndromic hearing loss." *Journal of Human Genetics*, 48:564-570 (2003).

Sabates-Bellver, "Transcriptome Profile of Human Colorectal Adenomas." *Mol Cancer Res.*, 5:1263-1275 (2007).

\* cited by examiner

FIG. 2. SEQ ID NO:1

5'-
gagctagcgctcaagcagagcccagcgcggtgctatcggacagagcctggcgagcgcaagcggcgcggggagccagcgg
ggctgagcgcggccagggtctgaacccagatttcccagactagctaccactccgcttgcccacgccccgggagctcgcggcg
cctggcggtcagcgaccagacgtccggggccgctgcgctcctggcccgcgaggcgtgacactgtctcggctacagacccag
agggagcacactgccaggatgggagctgctggaggcaggacttcctcttcaaggccatgctgaccatcagctggctcactct
gacctgcttccctggggccacatccacagtggctgctgggtgccctgaccagagccctgagttgcaacccctggaaccctggcc
atgaccaagaccaccatgtgcatatcggccagggcaagacactgctgctcacctcttctgccacggtctattccatccacatctca
gagggaggcaagctggtcattaaagaccacgacgagccgattgttttgcgaacccggcacatcctgattgacaacggaggaga
gctgcatgctgggagtgccctctgccctttccagggcaatttcaccatcattttgtatggaagggctgatgaaggtattcagccgg
atccttactatggtctgaagtacattggggttggtaaaggaggcgctcttgagttgcatggacagaaaaagctctcctggacatttc
tgaacaagaccccttcacccaggtggcatggcagaaggaggctatttttttgaaaggagctggggccaccgtggagttattgttcat
gtcatcgaccccaaatcaggcacagtcatccattctgaccggtttgacacctatagatccaagaaagagagtgaacgtctggtcc
agtatttgaacgcggtgcccgatggcaggatcctttctgttgcagtgaatgatgaaggttctcgaaatctggatgacatggccagg
aaggcgatgaccaaattgggaagcaaacacttcctgcaccttggatttagacacccttggagttttctaactgtgaaaggaaatcc
atcatcttcagtggaagaccatattgaatatcatggacatcgaggctctgctgctgcccgggtattcaaattgttccagacagagca
tggcgaatatttcaatgtttctttgtccagtgagtgggttcaagacgtggagtggacggagtggttcgatcatgataaagtatctcag
actaaaggtggggagaaaatttcagacctctggaaagctcacccaggaaaaatatgcaatcgtcccattgatatacaggccacta
caatggatggagttaacctcagcaccgaggttgtctacaaaaaaggccaggattataggtttgcttgctacgaccggggcagag
cctgccggagctaccgtgtacggttcctctgtgggaagcctgtgaggcccaaactcacagtcaccattgacaccaatgtgaaca
gcaccattctgaacttggaggataatgtacagtcatggaaacctggagatacccctggtcattgccagtactgattactccatgtacc
aggcagaagagttccaggtgcttccctgcagatcctgcgccccccaaccaggtcaaagtggcagggaaaccaatgtacctgcac
atcggggaggagatagacggcgtggacatgcgggcggaggttgggcttctgagccggaacatcatagtgatgggggagatg
gaggacaaatgctaccccctacagaaaccacatctgcaatttctttgacttcgatacctttgggggccacatcaagtttgctctggga
tttaaggcagcacacttggagggcacggagctgaagcatatgggacagcagctggtgggtcagtacccgattcacttccacctg
gccggtgatgtagacgaaaggggaggttatgacccacccacatacatcagggacctctccatccatcatacattctctcgctgcg
tcacagtccatggctccaatggcttgttgatcaaggacgttgtgggctataactctttgggccactgcttcttcacggaagatgggc
cggaggaacgcaacacttttgaccactgtcttggcctccttgtcaagtctggaaccctcctcccctcggaccgtgacagcaagat
gtgcaagatgatcacagaggactcctacccggggtacatccccaagcccaggcaagactgcaatgctgtgtccaccttctggat
ggccaatcccaacaacaacctcatcaactgtgccgctgcaggatctgaggaaactggattttggttttattttttccaccacgtaccaac
gggcccctccgtgggaatgtactccccaggttattcagagcacattccactgggaaaattctataacaaccgagcacattccaact
accgggctggcatgatcatagacaacggagtcaaaaccaccgaggcctctgccaaggacaagcggccgttcctctcaatcatc
tctgccagatacagccctcaccaggacgccgacccgctgaagccccgggagccggccatcatcagacacttcattgcctacaa
gaaccaggaccacggggcctggctgcgcggcggggatgtgtggctggacagctgccggtttgctgacaatggcattggcctg
accctggccagtggtggaaccttcccgtatgacgacggctccaagcaagagataaagaacagcttgtttgttggcgagagtggc
aacgtggggacggaaatgatggacaataggatctggggccctggcggcttggaccatagcggaaggaccctccctataggcc
agaattttccaattagaggaattcagttatatgatggcccccatcaacatccaaaactgcactttccgaaagtttgtggccctggagg
gccggcacaccagcgccctggccttccgcctgaataatgcctggcagagctgcccccataacaacgtgaccggcattgcctttg
aggacgttccgattacttccagagtgttcttcggagagcctgggccctggttcaaccagctggacatggatggggataagacatc
tgtgttccatgacgtcgacggctccgtgtccgagtaccctggctcctacctcacgaagaatgacaactggctggtccggcaccca
gactgcatcaatgttcccgactggagagggggccatttgcagtgggtgctatgcacagatgtacattcaagcctacaagaccagta
acctgcgaatgaagatcatcaagaatgacttccccagccaccctctttacctggagggggcgctcaccaggagcacccattacc
agcaataccaaccggttgtcaccctgcagaagggctacaccatccactgggaccagacggccccgccgaactcgccatctg
gctcatcaacttcaacaagggcgactggatccgagtgggctctgctacccgcgaggcaccacattctccatcctctcggatgtt
cacaatcgcctgctgaagcaaacgtccaagacgggcgtcttcgtgaggaccttgcagatggacaaagtggagcagagctacc
ctggcaggagccactactactgggacgaggactcagggctgttgttcctgaagctgaaagctcagaacgagagagagaagttt

FIG. 2 Cont.

gctttctgctccatgaaaggctgtgagaggataaagattaaagctctgattccaaagaacgcaggcgtcagtgactgcacagcca
cagcttaccccaagttcaccgagagggctgtcgtagacgtgccgatgcccaagaagctctttggttctcagctgaaaacaaagg
accatttcttggaggtgaagatggagagttccaagcagcacttcttccacctctggaacgacttcgcttacattgaagtggatggg
aagaagtacccccagttcggaggatggcatccaggtggtggtgattgacgggaaccaagggcgcgtggtgagccacacgagct
tcaggaactccattctgcaaggcataccatggcagcttttcaactatgtggcgaccatccctgacaattccatagtgcttatggcat
caaagggaagatacgtctccagaggcccatggaccagagtgctggaaaagcttggggcagacaggggtctcaagttgaaaga
gcaaatggcattcgttggcttcaaaggcagcttccggcccatctgggtgacactggacactgaggatcacaaagccaaaatcttc
caagttgtgcccatccctgtggtgaagaagaagaagttgtgaggacagctgccgcccggtgccacctcgtggtagactatgacg
gtgactcttggcagcagaccagtgggggatggctgggtcccccagcccctgccagcagctgcctgggaaggccgtgtttcag
ccctgatgggccaagggaaggctatcagagaccctggtgctgccacctgcccctactcaagtgtctacctggagcccctgggg
cggtgctggccaatgctggaaacattcactttcctgcagcctcttgggtgcttctctcctatctgtgcctcttcagtgggggtttggg
gaccatatcaggagacctggggttgtgctgacagcaaagatccactttggcaggagccctgacccagctaggaggtagtctgga
gggctggtcattcacagatccccatggtcttcagcagacaagtgagggtggtaaatgtaggagaaagagccttggccttaagga
aatctttactcctgtaagcaagagccaacctcacaggattaggagctggggtagaactggctatccttggggaagaggcaagcc
ctgcctctggccgtgtccacctttcaggagactttgagtggcaggtttggacttggactagatgactctcaaaggcccttttagttct
gagattccagaaatctgctgcatttcacatggtacctggaacccaacagttcatggatatccactgatatccatgatgctgggtgcc
ccagcgcacacgggatggagaggtgagaactaatgcctagcttgaggggtctgcagtccagtagggcaggcagtcaggtcca
tgtgcactgcaatgccaggtggagaaatcacagagaggtaaaatggaggccagtgccatttcagaggggaggctcaggaagg
cttcttgcttacaggaatgaaggctgggggcattttgctggggggagatgaggcagcctctggaatggctcagggattcagccct
ccctgccgctgcctgctgaagctggtgactacggggtcgcctttgctcacgtctctctggcccactcatgatggagaagtgtggt
cagaggggagcaatgggctttgctgcttatgagcacagaggaattcagtccccaggcagccctgcctctgactccaagagggt
gaagtccacagaagtgagctcctgccttagggcctcatttgctcttcatccagggaactgagcacagggggcctccaggagacc
ctagatgtgctcgtactccctcggcctgggatttcagagctggaaatatagaaaatatctagcccaaagccttcattttaacagatg
gggaaagtgagcccccaagatgggaaagaaccacacagctaagggagggcctggggagcccacccctagcccttgctgcc
acaccacattgcctcaacaaccggccccagagtgcccaggcactcctgaggtagcttctggaaatggggacaagtcccctcga
aggaaaggaaatgactagagtagaatgacagctagcagatctcttccctcctgctcccagcgcacacaaacccgccctccccctt
ggtgttggcggtccctgtggccttcactttgttcactacctgtcagcccagcctgggtgcacagtagctgcaactccccattggtgc
tacctggctctcctgtctctgcagctctacaggtgaggcccagcagagggagtagggctcgccatgtttctggtgagccaatttg
gctgatcttgggtgtctgaacagctattgggtccaccccagtcccttcagctgctgcttaatgccctgctctctccctggcccacct
tatagagagcccaaagagctcctgtaagaggagaactctatctgtggtttataatcttgcacgaggcaccagagtctccctgggt
cttgtgatgaactacatttatcccctttcctgccccaaccacaaactctttccttcaaagagggcctgcctggctccctccacccaac
tgcacccatgagactcggtccaagagtccattcccaggtgggagccaactgtcagggaggtctttcccaccaaacatctttcag
ctgctgggaggtgaccatagggctctgcttttaaagatatggctgcttcaaaggccagagtcacaggaaggacttcttccaggga
gattagtggtgatggagaggagagttaaaatgacctcatgtccttcttgtccacggttttgttgagttttcactcttctaatgcaagggt
ctcacactgtgaaccacttaggatgtgatcactttcaggtggccaggaatgttgaatgtctttggctcagttcatttaaaaaagatatc
tatttgaaagttctcagagttgtacatatgtttcacagtacaggatctgtacataaaagtttctttcctaaaccattcaccaagagccaa
tatctaggcattttcttggtagcacaaattttcttattgcttagaaaattgtcctccttgttatttctgtttgtaagacttaagtgagttaggt
ctttaaggaaagcaacgctcctctgaaatgcttgtctttttctgttgccgaaatagctggtccttttcgggagttagatgtatagagt
gtttgtatgtaaacatttcttgtaggcatcaccatgaacaaagatatattttctatttatttattatatgtgcacttcaagaagtcactgtca
gagaaataaagaattgtcttaaatgtc-3'

FIG. 3. SEQ ID NO:2

5'- CCT CTC CAT CCA TCA TAC ATT -3'

FIG. 4. SEQ ID NO:3 (GenBank accession number EF155570).

5'- GCA CAG GTT CCA GGG ACA ATT -3'

1) Sequence of C43 protein (SEQ ID NO:4)

```
MGAAGRQDFLFKAMLTISWLTLTCFPGATSTVAAGCPDQSPELQPWNPGH  50
DQDHHVHIGQGKTLLLTSSATVYSIHISEGGKLVIKDHDEPIVLRTRHIL  100
IDNGGELHAGSALCPFQGNFTIILYGRADEGIQPDPYYGLKYIGVGKGGA  150
LELHGQKKLSWTFLNKTLHPGGMAEGGYFFERSWGHRGVIVHVIDPKSGT  200
VIHSDRFDTYRSKKESERLVQYLNAVPDGRILSVAVNDEGSRNLDDMARK  250
AMTKLGSKHFLHLGFRHPWSFLTVKGNPSSSVEDHIEYHGHRGSAAARVF  300
KLFQTEHGEYFNVSLSSEWVQDVEWTEWFDHDKVSQTKGGEKISDLWKAH  350
PGKICNRPIDIQATTMDGVNLSTEVVYKKGQDYRFACYDRGRACRSYRVR  400
FLCGKPVRPKLTVTIDTNVNSTILNLEDNVQSWKPGDTLVIASTDYSMYQ  450
AEEFQVLPCRSCAPNQVKVAGKPMYLHIGEEIDGVDMRAEVGLLSRNIIV  500
MGEMEDKCYPYRNHICNFFDFDTFGGHIKFALGFKAAHLEGTELKHMGQQ  550
LVGQYPIHFHLAGDVDERGGYDPPTYIRDLSIHHTFSRCVTVHGSNGLLI  600
KDVVGYNSLGHCFFTEDGPEERNTFDHCLGLLVKSGTLLPSDRDSKMCKM  650
ITEDSYPGYIPKPRQDCNAVSTFWMANPNNNLINCAAAGSEETGFWFIFH  700
HVPTGPSVGMYSPGYSEHIPLGKFYNNRAHSNYRAGMIIDNGVKTTEASA  750
KDKRPFLSIISARYSPHQDADPLKPREPAIIRHFIAYKNQDHGAWLRGGD  800
VWLDSCRFADNGIGLTLASGGTFPYDDGSKQEIKNSLFVGESGNVGTEMM  850
DNRIWGPGGLDHSGRTLPIGQNFPIRGIQLYDGPINIQNCTFRKFVALEG  900
RHTSALAFRLNNAWQSCPHNNVTGIAFEDVPITSRVFFGEPGPWFNQLDM  950
DGDKTSVFHDVDGSVSEYPGSYLTKNDNWLVRHPDCINVPDWRGAICSGC  1000
YAQMYIQAYKTSNLRMKIIKNDFPSHPLYLEGALTRSTHYQQYQPVVTLQ  1050
KGYTIHWDQTAPAELAIWLINFNKGDWIRVGLCYPRGTTFSILSDVHNRL  1100
QSYPGRSHYYWDEDSGLLFLKLKAQNEREKFAFCSMKGCERIKIKALIPK  1150
NAGVSDCTATAYPKFTERAVVDVPMPKKLFGSQLKTKDHFLEVKMESSKQ  1200
HFFHLWNDFAYIEVDGKKYPSSEDGIQVVVIDGNQGRVVSHTSFRNSILQ  1250
GIPWQLFNYVATIPDNSIVLMASKGRYVSRGPWTRVLEKLGADRGLKLKE  1300
QMAFVGFKGSFRPIWVTLDTEDHKAKIFQVVPIPVVKKKKL*         1341
```

FIG. 10

A.
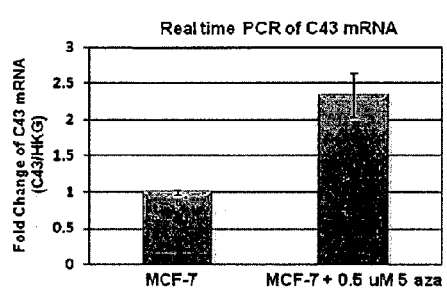
B.
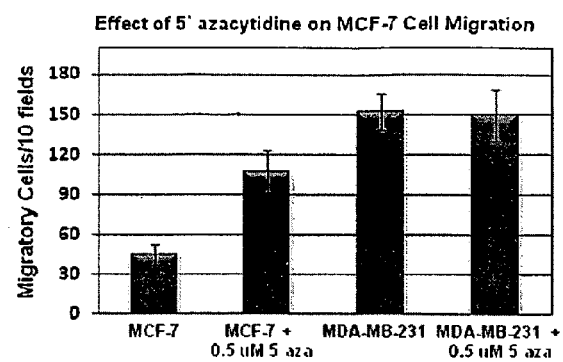
Fig. 17

SEQUENCE LISTING

```
<160> NUMBER OF SEQ ID NOS: 17

<210> SEQ ID NO 1
<211> LENGTH: 7080
<212> TYPE: DNA
<213> ORGANISM: Homo sapiens

<400> SEQUENCE: 1
gagctagcgc tcaagcagag cccagcgcgg tgctatcgga cagagcctgg cgagcgcaag      60
cggcgcgggg agccagcggg gctgagcgcg gccagggtct gaacccagat ttcccagact     120
agctaccact ccgcttgccc acgccccggg agctcgcggc gcctggcggt cagcgaccag     180
acgtccgggg ccgctgcgct cctggcccgc gaggcgtgac actgtctcgg ctacagaccc     240
agagggagca cactgccagg atgggagctg ctgggaggca ggacttcctc ttcaaggcca     300
tgctgaccat cagctggctc actctgacct gcttccctgg ggccacatcc acagtggctg     360
ctgggtgccc tgaccagagc cctgagttgc aaccctggaa ccctggccat gaccaagacc     420
accatgtgca tatcggccag ggcaagacac tgctgctcac ctcttctgcc acggtctatt     480
ccatccacat ctcagaggga ggcaagctgg tcattaaaga ccacgacgag ccgattgttt     540
tgcgaacccg gcacatcctg attgacaacg gaggagagct gcatgctggg agtgccctct     600
gcccttccca gggcaatttc accatcattt tgtatggaag ggctgatgaa ggtattcagc     660
cggatcctta ctatggtctg aagtacattg gggttggtaa aggaggcgct cttgagttgc     720
atggacagaa aaagctctcc tggacatttc tgaacaagac ccttcaccca ggtggcatgg     780
```

```
cagaaggagg ctatttttt gaaaggagct ggggccaccg tggagttatt gttcatgtca      840
tcgaccccaa atcaggcaca gtcatccatt ctgaccggtt tgacacctat agatccaaga     900
aagagagtga acgtctggtc cagtatttga acgcggtgcc cgatggcagg atcctttctg    960
ttgcagtgaa tgatgaaggt tctcgaaatc tggatgacat ggccaggaag gcgatgacca    1020
aattgggaag caaacacttc ctgcaccttg gatttagaca cccttggagt tttctaactg    1080
tgaaaggaaa tccatcatct tcagtggaag accatattga atatcatgga catcgaggct    1140
ctgctgctgc ccgggtattc aaattgttcc agacagagca tggcgaatat ttcaatgttt    1200
ctttgtccag tgagtgggtt caagacgtgg agtggacgga gtggttcgat catgataaag    1260
tatctcagac taaaggtggg gagaaaattt cagacctctg gaaagctcac ccaggaaaaa    1320
tatgcaatcg tcccattgat atacaggcca ctacaatgga tggagttaac ctcagcaccg    1380
aggttgtcta caaaaaggc caggattata ggtttgcttg ctacgaccgg ggcagagcct     1440
gccggagcta ccgtgtacgg ttcctctgtg ggaagcctgt gaggcccaaa ctcacagtca    1500
ccattgacac caatgtgaac agcaccattc tgaacttgga ggataatgta cagtcatgga    1560
aacctgagga taccctggtc attgccagta ctgattactc catgtaccag gcagaagagt    1620
tccaggtgct tccctgcaga tcctgcgccc caaccaggt caaagtggca gggaaaccaa     1680
tgtacctgca catcggggag gagatagacg gcgtggacat gcgggcggag gttgggcttc    1740
tgagccggaa catcatagtg atgggggaga tggaggacaa atgctacccc tacagaaacc    1800
acatctgcaa tttctttgac ttcgatacct tggggggcca catcaagttt gctctgggat    1860
ttaaggcagc acacttggag ggcacggagc tgaagcatat gggacagcag ctggtgggtc    1920
agtacccgat tcacttccac ctggccggtg atgtagacga aggggaggt tatgacccac      1980
ccacatacat cagggacctc tccatccatc atacattctc tcgctgcgtc acagtccatg    2040
gctccaatgg cttgttgatc aaggacgttg tgggctataa ctctttgggc cactgcttct    2100
tcacggaaga tgggccggag gaacgcaaca cttttgacca ctgtcttggc ctccttgtca    2160
agtctggaac cctcctcccc tcggaccgtg acagcaagat gtgcaagatg atcacagagg    2220
actcctaccc ggggtacatc cccaagccca ggcaagactg caatgctgtg tccaccttct    2280
ggatggccaa tcccaacaac aacctcatca actgtgccgc tgcaggatct gaggaaactg    2340
gattttggtt tattttttcac cacgtaccaa cgggcccctc cgtgggaatg tactccccag    2400
gttattcaga gcacattcca ctgggaaaat tctataacaa ccgagcacat tccaactacc    2460
gggctggcat gatcatagac aacggagtca aaaccaccga ggcctctgcc aaggacaagc    2520
ggccgttcct ctcaatcatc tctgccagat acagccctca ccaggacgcc gacccgctga    2580
agccccggga gccggccatc atcagacact tcattgccta caagaaccag gaccacgggg    2640
cctggctgcg cggcggggat gtgtggctgg acagctgccg gtttgctgac aatggcattg    2700
gcctgaccct ggccagtggt ggaaccttcc cgtatgacga cggctccaag caagagataa    2760
agaacagctt gtttgttggc gagagtggca acgtggggac ggaaatgatg gacaatagga    2820
tctgggccc tggcggcttg gaccatagcg aaggaccct cctataggc cagaattttc       2880
caattagagg aattcagtta tatgatgccc ccatcaacat ccaaaactgc actttccgaa    2940
agtttgtggc cctggagggc cggcacacca gcgccctggc cttccgcctg aataatgcct    3000
ggcagagctg ccccccataac aacgtgaccg gcattgcctt tgaggacgtt ccgattactt    3060
ccagagtgtt cttcggagag cctgggccct ggttcaacca gctggacatg gatggggata    3120
```

```
agacatctgt gttccatgac gtcgacggct ccgtgtccga gtaccctggc tcctacctca    3180
cgaagaatga caactggctg gtccggcacc cagactgcat caatgttccc gactggagag    3240
gggccatttg cagtgggtgc tatgcacaga tgtacattca agcctacaag accagtaacc    3300
tgcgaatgaa gatcatcaag aatgacttcc ccagccaccc tctttacctg gaggggcgc     3360
tcaccaggag cacccattac cagcaatacc aaccggttgt caccctgcag aagggctaca    3420
ccatccactg ggaccagacg gcccccgccg aactcgccat ctggctcatc aacttcaaca    3480
agggcgactg gatccgagtg gggctctgct acccgcgagg caccacattc tccatcctct    3540
cggatgttca caatcgcctg ctgaagcaaa cgtccaagac gggcgtcttc gtgaggacct    3600
tgcagatgga caaagtggag cagagctacc ctggcaggag ccactactac tgggacgagg    3660
actcagggct gttgttcctg aagctgaaag ctcagaacga gagagagaag tttgctttct    3720
gctccatgaa aggctgtgag aggataaaga ttaaagctct gattccaaag aacgcaggcg    3780
tcagtgactg cacagccaca gcttacccca agttcaccga gagggctgtc gtagacgtgc    3840
cgatgcccaa gaagctcttt ggttctcagc tgaaaacaaa ggaccatttc ttggaggtga    3900
agatggagag ttccaagcag cacttcttcc acctctggaa cgacttcgct tacattgaag    3960
tggatgggaa gaagtacccc agttcggagg atggcatcca ggtggtggtg attgacggga    4020
accaagggcg cgtggtgagc cacacgagct caggaactc  cattctgcaa ggcataccat    4080
ggcagctttt caactatgtg gcgaccatcc ctgacaattc catagtgctt atggcatcaa    4140
agggaagata cgtctcccaga ggcccatgga ccagagtgct ggaaaagctt ggggcagaca    4200
ggggtctcaa gttgaaagag caaatggcat tcgttggctt caaaggcagc ttccggccca    4260
tctgggtgac actggacact gaggatcaca aagccaaaat cttccaagtt gtgcccatcc    4320
ctgtggtgaa gaagaagaag ttgtgaggac agctgccgcc cggtgccacc tcgtggtaga    4380
ctatgacggt gactcttggc agcagaccag tgggggatgg ctgggtcccc cagcccctgc    4440
cagcagctgc ctgggaaggc cgtgtttcag ccctgatggg ccaagggaag ctatcagag    4500
accctggtgc tgccacctgc ccctactcaa gtgtctacct ggagcccctg ggcggtgct     4560
ggccaatgct ggaaacattc actttcctgc agcctcttgg gtgcttctct cctatctgtg    4620
cctcttcagt gggggtttgg ggaccatatc aggagacctg ggttgtgctg acagcaaaga    4680
tccactttgg caggagccct gacccagcta ggaggtagtc tggagggctg gtcattcaca    4740
gatccccatg gtcttcagca gacaagtgag ggtggtaaat gtaggagaaa gagccttggc    4800
cttaaggaaa tctttactcc tgtaagcaag agccaacctc acaggattag gagctggggt    4860
agaactggct atccttgggg aagaggcaag ccctgcctct ggccgtgtcc acctttcagg    4920
agactttgag tggcaggttt ggacttggac tagatgactc tcaaaggccc ttttagttct    4980
gagattccag aaatctgctg catttcacat ggtacctgga acccaacagt tcatggatat    5040
ccactgatat ccatgatgct gggtgcccca gcgcacacgg gatggagagg tgagaactaa    5100
tgcctagctt gaggggtctg cagtccagta gggcaggcag tcaggtccat gtgcactgca    5160
atgccaggtg gagaaatcac agagaggtaa aatggaggcc agtgccattt cagaggggag    5220
gctcaggaag gcttcttgct tacaggaatg aaggctgggg cattttgct  gggggagat     5280
gaggcagcct ctggaatggc tcagggattc agccctccct gccgctgcct gctgaagctg    5340
gtgactacgg ggtcgccctt tgctcacgtc tctctggccc actcatgatg gagaagtgtg    5400
gtcagagggg agcaatgggc tttgctgctt atgagcacag aggaattcag tcccaggca     5460
gccctgcctc tgactccaag agggtgaagt ccacagaagt gagctcctgc cttagggcct    5520
```

-continued

```
catttgctct tcatccaggg aactgagcac aggggcctc caggagaccc tagatgtgct    5580
cgtactccct cggcctggga tttcagagct ggaaatatag aaaatatcta gcccaaagcc    5640
ttcattttaa cagatgggga aagtgagccc ccaagatggg aaagaaccac acagctaagg    5700
gagggcctgg ggagcccac cctagcccctt gctgccacac cacattgcct caacaaccgg    5760
ccccagagtg cccaggcact cctgaggtag cttctggaaa tggggacaag tccctcgaa    5820 ggaaaggaaa tgactagagt agaatgacag ctagcagatc tcttccctcc tgctcccagc    5880
gcacacaaac ccgccctccc cttggtgttg gcggtccctg tggccttcac tttgttcact    5940
acctgtcagc ccagcctggg tgcacagtag ctgcaactcc ccattggtgc tacctggctc    6000
tcctgtctct gcagctctac aggtgaggcc cagcagaggg agtagggctc gccatgtttc    6060
tggtgagcca atttggctga tcttgggtgt ctgaacagct attgggtcca ccccagtccc    6120
tttcagctgc tgcttaatgc cctgctctct ccctggccca ccttatagag agcccaaaga    6180
gctcctgtaa gagggagaac tctatctgtg gtttataatc ttgcacgagg caccagagtc    6240
tccctgggtc ttgtgatgaa ctacatttat cccctttcct gccccaacca caaactcttt    6300
ccttcaaaga gggcctgcct ggctccctcc acccaactgc acccatgaga ctcggtccaa    6360
gagtccattc cccaggtggg agccaactgt cagggaggtc tttcccacca aacatctttc    6420
agctgctggg aggtgaccat agggctctgc ttttaaagat atggctgctt caaaggccag    6480
agtcacagga aggacttctt ccagggagat tagtggtgat ggagaggaga gttaaaatga    6540
cctcatgtcc ttcttgtcca cggttttgtt gagttttcac tcttctaatg caagggtctc    6600
acactgtgaa ccacttagga tgtgatcact ttcaggtggc caggaatgtt gaatgtcttt    6660
ggctcagttc atttaaaaaa gatatctatt tgaaagttct cagagttgta catatgtttc    6720
acagtacagg atctgtacat aaaagtttct ttcctaaacc attcaccaag agccaatatc    6780
taggcatttt cttggtagca caaattttct tattgcttag aaaattgtcc tccttgttat    6840
ttctgtttgt aagacttaag tgagttaggt ctttaaggaa agcaacgctc ctctgaaatg    6900
cttgtctttt ttctgttgcc gaaatagctg gtccttttc gggagttaga tgtatagagt    6960
gtttgtatgt aaacatttct tgtaggcatc accatgaaca aagatatatt ttctatttat    7020
ttattatatg tgcacttcaa gaagtcactg tcagagaaat aaagaattgt cttaaatgtc    7080
```

<210> SEQ ID NO 2
<211> LENGTH: 21
<212> TYPE: DNA
<213> ORGANISM: Homo sapiens

<400> SEQUENCE: 2
cctctccatc catcatacat t                                              21

<210> SEQ ID NO 3
<211> LENGTH: 21
<212> TYPE: DNA
<213> ORGANISM: Homo sapiens

<400> SEQUENCE: 3
gcacaggttc cagggacaat t                                              21

<210> SEQ ID NO 4
<211> LENGTH: 1341
<212> TYPE: PRT
<213> ORGANISM: Homo sapiens

<400> SEQUENCE: 4

```
Met Gly Ala Ala Gly Arg Gln Asp Phe Leu Phe Lys Ala Met Leu Thr
1               5                   10                  15

Ile Ser Trp Leu Thr Leu Thr Cys Phe Pro Gly Ala Thr Ser Thr Val
            20                  25                  30

Ala Ala Gly Cys Pro Asp Gln Ser Pro Glu Leu Gln Pro Trp Asn Pro
        35                  40                  45

Gly His Asp Gln Asp His His Val His Ile Gly Gln Gly Lys Thr Leu
    50                  55                  60

Leu Leu Thr Ser Ser Ala Thr Val Tyr Ser Ile His Ile Ser Glu Gly
65                  70                  75                  80

Gly Lys Leu Val Ile Lys Asp His Asp Glu Pro Ile Val Leu Arg Thr
                85                  90                  95

Arg His Ile Leu Ile Asp Asn Gly Gly Glu Leu His Ala Gly Ser Ala
            100                 105                 110

Leu Cys Pro Phe Gln Gly Asn Phe Thr Ile Ile Leu Tyr Gly Arg Ala
        115                 120                 125

Asp Glu Gly Ile Gln Pro Asp Pro Tyr Tyr Gly Leu Lys Tyr Ile Gly
    130                 135                 140

Val Gly Lys Gly Gly Ala Leu Glu Leu His Gly Gln Lys Lys Leu Ser
145                 150                 155                 160

Trp Thr Phe Leu Asn Lys Thr Leu His Pro Gly Gly Met Ala Glu Gly
                165                 170                 175

Gly Tyr Phe Phe Glu Arg Ser Trp Gly His Arg Gly Val Ile Val His
            180                 185                 190

Val Ile Asp Pro Lys Ser Gly Thr Val Ile His Ser Asp Arg Phe Asp
        195                 200                 205

Thr Tyr Arg Ser Lys Lys Glu Ser Glu Arg Leu Val Gln Tyr Leu Asn
    210                 215                 220

Ala Val Pro Asp Gly Arg Ile Leu Ser Val Ala Val Asn Asp Glu Gly
225                 230                 235                 240

Ser Arg Asn Leu Asp Asp Met Ala Arg Lys Ala Met Thr Lys Leu Gly
                245                 250                 255

Ser Lys His Phe Leu His Leu Gly Phe Arg His Pro Trp Ser Phe Leu
            260                 265                 270

Thr Val Lys Gly Asn Pro Ser Ser Val Glu Asp His Ile Glu Tyr
        275                 280                 285

His Gly His Arg Gly Ser Ala Ala Ala Arg Val Phe Lys Leu Phe Gln
    290                 295                 300

Thr Glu His Gly Glu Tyr Phe Asn Val Ser Leu Ser Ser Glu Trp Val
305                 310                 315                 320

Gln Asp Val Glu Trp Thr Glu Trp Phe Asp His Asp Lys Val Ser Gln
                325                 330                 335

Thr Lys Gly Gly Glu Lys Ile Ser Asp Leu Trp Lys Ala His Pro Gly
            340                 345                 350

Lys Ile Cys Asn Arg Pro Ile Asp Ile Gln Ala Thr Thr Met Asp Gly
        355                 360                 365

Val Asn Leu Ser Thr Glu Val Tyr Lys Lys Gly Gln Asp Tyr Arg
    370                 375                 380

Phe Ala Cys Tyr Asp Arg Gly Arg Ala Cys Arg Ser Tyr Arg Val Arg
385                 390                 395                 400

Phe Leu Cys Gly Lys Pro Val Arg Pro Lys Leu Thr Val Thr Ile Asp
                405                 410                 415
```

```
Thr Asn Val Asn Ser Thr Ile Leu Asn Leu Glu Asp Asn Val Gln Ser
            420                 425                 430

Trp Lys Pro Gly Asp Thr Leu Val Ile Ala Ser Thr Asp Tyr Ser Met
            435                 440                 445

Tyr Gln Ala Glu Glu Phe Gln Val Leu Pro Cys Arg Ser Cys Ala Pro
            450                 455                 460

Asn Gln Val Lys Val Ala Gly Lys Pro Met Tyr Leu His Ile Gly Glu
465                 470                 475                 480

Glu Ile Asp Gly Val Asp Met Arg Ala Glu Val Gly Leu Leu Ser Arg
                485                 490                 495

Asn Ile Ile Val Met Gly Glu Met Glu Asp Lys Cys Tyr Pro Tyr Arg
            500                 505                 510

Asn His Ile Cys Asn Phe Phe Asp Phe Asp Thr Phe Gly Gly His Ile
            515                 520                 525

Lys Phe Ala Leu Gly Phe Lys Ala Ala His Leu Glu Gly Thr Glu Leu
            530                 535                 540

Lys His Met Gly Gln Gln Leu Val Gly Gln Tyr Pro Ile His Phe His
545                 550                 555                 560

Leu Ala Gly Asp Val Asp Glu Arg Gly Gly Tyr Asp Pro Pro Thr Tyr
                565                 570                 575

Ile Arg Asp Leu Ser Ile His His Thr Phe Ser Arg Cys Val Thr Val
            580                 585                 590

His Gly Ser Asn Gly Leu Leu Ile Lys Asp Val Val Gly Tyr Asn Ser
            595                 600                 605

Leu Gly His Cys Phe Phe Thr Glu Asp Gly Pro Glu Glu Arg Asn Thr
            610                 615                 620

Phe Asp His Cys Leu Gly Leu Leu Val Lys Ser Gly Thr Leu Leu Pro
625                 630                 635                 640

Ser Asp Arg Asp Ser Lys Met Cys Lys Met Ile Thr Glu Asp Ser Tyr
                645                 650                 655

Pro Gly Tyr Ile Pro Lys Pro Arg Gln Asp Cys Asn Ala Val Ser Thr
            660                 665                 670

Phe Trp Met Ala Asn Pro Asn Asn Asn Leu Ile Asn Cys Ala Ala Ala
            675                 680                 685

Gly Ser Glu Glu Thr Gly Phe Trp Phe Ile Phe His His Val Pro Thr
            690                 695                 700

Gly Pro Ser Val Gly Met Tyr Ser Pro Gly Tyr Ser Glu His Ile Pro
705                 710                 715                 720

Leu Gly Lys Phe Tyr Asn Asn Arg Ala His Ser Asn Tyr Arg Ala Gly
                725                 730                 735

Met Ile Ile Asp Asn Gly Val Lys Thr Thr Glu Ala Ser Ala Lys Asp
            740                 745                 750

Lys Arg Pro Phe Leu Ser Ile Ile Ser Ala Arg Tyr Ser Pro His Gln
            755                 760                 765

Asp Ala Asp Pro Leu Lys Pro Arg Glu Pro Ala Ile Ile Arg His Phe
            770                 775                 780

Ile Ala Tyr Lys Asn Gln Asp His Gly Ala Trp Leu Arg Gly Asp
785                 790                 795                 800

Val Trp Leu Asp Ser Cys Arg Phe Ala Asp Asn Gly Ile Gly Leu Thr
                805                 810                 815

Leu Ala Ser Gly Gly Thr Phe Pro Tyr Asp Asp Gly Ser Lys Gln Glu
            820                 825                 830
```

-continued

```
Ile Lys Asn Ser Leu Phe Val Gly Glu Ser Gly Asn Val Gly Thr Glu
            835                 840                 845

Met Met Asp Asn Arg Ile Trp Gly Pro Gly Gly Leu Asp His Ser Gly
850                 855                 860

Arg Thr Leu Pro Ile Gly Gln Asn Phe Pro Ile Arg Gly Ile Gln Leu
865                 870                 875                 880

Tyr Asp Gly Pro Ile Asn Ile Gln Asn Cys Thr Phe Arg Lys Phe Val
                885                 890                 895

Ala Leu Glu Gly Arg His Thr Ser Ala Leu Ala Phe Arg Leu Asn Asn
            900                 905                 910

Ala Trp Gln Ser Cys Pro His Asn Asn Val Thr Gly Ile Ala Phe Glu
            915                 920                 925

Asp Val Pro Ile Thr Ser Arg Val Phe Phe Gly Glu Pro Gly Pro Trp
            930                 935                 940

Phe Asn Gln Leu Asp Met Asp Gly Asp Lys Thr Ser Val Phe His Asp
945                 950                 955                 960

Val Asp Gly Ser Val Ser Glu Tyr Pro Gly Ser Tyr Leu Thr Lys Asn
                965                 970                 975

Asp Asn Trp Leu Val Arg His Pro Asp Cys Ile Asn Val Pro Asp Trp
            980                 985                 990

Arg Gly Ala Ile Cys Ser Gly Cys Tyr Ala Gln Met Tyr Ile Gln Ala
            995                1000                1005

Tyr Lys Thr Ser Asn Leu Arg Met Lys Ile Ile Lys Asn Asp Phe
    1010                1015                1020

Pro Ser His Pro Leu Tyr Leu Glu Gly Ala Leu Thr Arg Ser Thr
    1025                1030                1035

His Tyr Gln Gln Tyr Gln Pro Val Val Thr Leu Gln Lys Gly Tyr
    1040                1045                1050

Thr Ile His Trp Asp Gln Thr Ala Pro Ala Glu Leu Ala Ile Trp
    1055                1060                1065

Leu Ile Asn Phe Asn Lys Gly Asp Trp Ile Arg Val Gly Leu Cys
    1070                1075                1080

Tyr Pro Arg Gly Thr Thr Phe Ser Ile Leu Ser Asp Val His Asn
    1085                1090                1095

Arg Leu Gln Ser Tyr Pro Gly Arg Ser His Tyr Tyr Trp Asp Glu
    1100                1105                1110

Asp Ser Gly Leu Leu Phe Leu Lys Leu Lys Ala Gln Asn Glu Arg
    1115                1120                1125

Glu Lys Phe Ala Phe Cys Ser Met Lys Gly Cys Glu Arg Ile Lys
    1130                1135                1140

Ile Lys Ala Leu Ile Pro Lys Asn Ala Gly Val Ser Asp Cys Thr
    1145                1150                1155

Ala Thr Ala Tyr Pro Lys Phe Thr Glu Arg Ala Val Val Asp Val
    1160                1165                1170

Pro Met Pro Lys Lys Leu Phe Gly Ser Gln Leu Lys Thr Lys Asp
    1175                1180                1185

His Phe Leu Glu Val Lys Met Glu Ser Ser Lys Gln His Phe Phe
    1190                1195                1200

His Leu Trp Asn Asp Phe Ala Tyr Ile Glu Val Asp Gly Lys Lys
    1205                1210                1215

Tyr Pro Ser Ser Glu Asp Gly Ile Gln Val Val Val Ile Asp Gly
    1220                1225                1230

Asn Gln Gly Arg Val Val Ser His Thr Ser Phe Arg Asn Ser Ile
```

Leu Gln Gly Ile Pro Trp Gln Leu Phe Asn Tyr Val Ala Thr Ile
1235                1240                1245

Pro Asp Asn Ser Ile Val Leu Met Ala Ser Lys Gly Arg Tyr Val
    1250                1255                1260

Ser Arg Gly Pro Trp Thr Arg Val Leu Glu Lys Leu Gly Ala Asp
1265                1270                1275

Arg Gly Leu Lys Leu Lys Glu Gln Met Ala Phe Val Gly Phe Lys
    1280                1285                1290

Gly Ser Phe Arg Pro Ile Trp Val Thr Leu Asp Thr Glu Asp His
1295                1300                1305

Lys Ala Lys Ile Phe Gln Val Val Pro Ile Pro Val Val Lys Lys
    1310                1315                1320

Lys Lys Leu
1325                1330                1335

1340

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gtggaagacc atattgaata t                                    21

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
gcctctccat ccatcataca tt                                   22

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gccatctggc tcatcaactt                                      20

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gctccaagca agagataaag a                                    21

<210> SEQ ID NO 9
<211> LENGTH: 21
<212> TYPE: DNA
<213> ORGANISM: Artificial Sequence
<220> FEATURE:
<223> OTHER INFORMATION: Synthetic

```
<400> SEQUENCE: 9
ggacggaaat gatggacaat a                                          21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
gggataagac atctgtgttc c                                          21

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
gcacccagac tgcatcaatg t                                          21

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
gcacccatta ccagcaatac c                                          21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ggaccttgca gatggacaaa g                                          21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
gcccactcat gatggagaag t                                          21

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
gcaatgggct ttgctgctta t                                          21

<210> SEQ ID NO 16
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 16
ggaaatgact agagtagaat g                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
ggtctttccc accaaacatc t                                              21
```

MULTI-WELL PLATFORM

This application is the U.S. National Stage of International Application PCT/US2009/04184, filed Jul. 20, 2009, which claims priority under 35 U.S.C. 119(e) to U.S. provisional Application Ser. No. 61/082,612, filed on Jul. 22, 2008, herein incorporated by reference in its entirety for all purposes.

FIELD OF THE INVENTION

The present invention relates to the diagnosis and treatment of cancer, and in particular breast cancer. Specifically, in some embodiments the invention relates to methods of diagnosing cancer, and in particular breast cancer, using an antibody specific for a gene product that localizes selectively to the endoplasmic reticulum of the cancer cell(s). In some embodiments, the invention relates to methods of treating cancer, and in particular breast cancer, by administering a composition comprising an RNA interference sequence (e.g., shRNA, RNAi and/or siRNA molecule) characterized by an ability to hybridize to an mRNA molecule, which mRNA molecule is encoded by the C43 gene (SEQ ID NO: 1). The invention additionally relates to methods for detecting cancer cells by detecting reduced methylation of the C43 promoter, and methods for reducing cancer metastasis by using demethylation inhibitors that result in increased methylation of the C43 promoter. The invention additionally relates to an in vitro 3-dimensional assay for detecting migrating cells, identifying test agents and/or nucleotide sequences that alter cell migration.

BACKGROUND

Breast cancer is the second most common type of cancer (after lung cancer) and is the most common cause of cancer death among women worldwide. The number of breast cancer cases globally has increased significantly since the 1970s, a phenomenon partly blamed on modern lifestyles in the Western world, with the highest incidence occurring in North America. Women in the United States have a 1 in 8 (12.5%) lifetime chance of developing invasive breast cancer and a 1 in 35 (3%) chance of breast cancer causing their death. In 2007, breast cancer caused over 40,000 deaths in the U.S. The most life-threatening aspect of cancer is metastasis. Crucial steps in this disseminated process include cell migration and invasion of tumor cells into the vasculature and surrounding matrices. Metastatic cancers that spread to other tissues distant from the original tumor site are the most serious form of breast cancer. The most common place for breast cancer to metastasize is into the lymph nodes under the arm or above the collarbone on the same side as the cancer. Other common sites of breast cancer metastasis are the brain, the bones, and the liver.

Evidence suggests that at the time of diagnosis, a high proportion of patients already have micrometastasis. Early detection coupled with effective therapeutic intervention is crucial in surviving breast cancer. While breast cancer mortality rates have been gradually declining, due at least in part to improved screening and treatment methods, presently available diagnostic markers for breast cancer often fail to detect cancerous cells early enough for therapeutic intervention to prevent metastasis.

There is thus a need to identify mechanisms responsible for the metastatic process, diagnostic markers for breast cancer that enable early detection of cells exhibiting a metastatic phenotype, and therapeutic target(s) for inhibiting cancer cell migration and invasion.

SUMMARY OF THE INVENTION

The present invention, in some embodiments, relates to the diagnosis and treatment of cancer, and in particular breast cancer. In some embodiments, the invention relates to methods of diagnosing cancer, and in particular breast cancer, using an antibody specific for a gene product that localizes to the endoplasmic reticulum of the cancer cell(s). In some embodiments, the invention relates to methods of treating cancer, and in particular breast cancer, by administering to a subject in need thereof or suspected of being in need thereof, a composition comprising a molecule capable of inhibiting an mRNA molecule encoded by the C43 gene. It is not necessary that there be complete inhibition, for the present application it is sufficient for there to be some inhibition. In some embodiments, said hybridization is diagnostic of cancer, and in particular breast cancer.

A first general embodiment of the present invention contemplates a composition comprising an shRNA molecule comprising nucleotide Sequence ID NO: 2.

A second general embodiment of the present invention contemplates a method of treating cancer, and in particular breast cancer, comprising: providing; a subject with cancer or suspected of having cancer, and in particular breast cancer; and a composition comprising an shRNA molecule capable of inhibiting the mRNA molecule encoded by nucleotide Sequence ID NO: 1; and administering said composition to said subject. In one embodiment, said subject is a human. In another embodiment, the mode of said administration includes but is not limited to intravenous, intrathecal, subcutaneous, intramuscular, direct injection into the tumor and inhalation. In another embodiment, the composition is co-administered with an anti-cancer drug. In a further embodiment, the composition is administered after an anti-cancer. In one embodiment, the composition is Paclitaxel. In one embodiment the cancer is metastatic. In another embodiment the cancer is chemoresistant.

Antibody treatment of human beings with cancer is well-known in the art, for example in U.S. Pat. No. 5,736,137 (herein incorporated by reference). Anti-sense treatment of human beings with cancer is also well-known in the art, for example U.S. Pat. No. 7,273,855 (herein incorporated by reference).

A third general embodiment of the present invention contemplates a method of diagnosing cancer, and in particular breast cancer, comprising: providing: a subject; a tissue sample from a subject; and an antibody specific for the gene product encoded by Sequence ID NO: 1; introducing said antibody to said tissue; and determining whether said antibody binds said gene product in said tissue. In one embodiment, said antibody binds said gene product in the endoplasmic reticulum of said tissue.

In some embodiments, the invention relates to methods of diagnosing cancer, and in particular breast cancer, using an antibody specific for a gene product that localizes to the endoplasmic reticulum of the cancer cell(s). In some embodiments, said antibody is specific for the C43 gene product. In some embodiments, said antibody detects the C43 gene product in a cell obtained from a tissue sample, such as a tissue biopsy.

In some embodiments, the invention relates to methods of treating cancer, and in particular breast cancer, by administering to a subject in need thereof or suspected of being in need thereof, a composition comprising a molecule capable of inhibiting an mRNA molecule encoded by the C43 gene. In some embodiments, said molecule is an antisense molecule capable of recognizing and binding C43 RNA (including but not limited to mRNA and non-spliced RNA). In some embodiments, said anti-sense molecule is administered to an individual with cancer, in particular breast cancer, at a sufficient dose such that C43 RNA is inhibited or the amount of C43 (RNA or protein) is reduced. In some embodiments, said anti-sense molecule is an siRNA, shRNA, and/or RNAi molecule. It is not necessary that there be complete inhibition or reduction, for the present application it is sufficient for there to be some inhibition or reduction. Anti-sense treatment of human beings with cancer is well known in the art, for example U.S. Pat. No. 7,273,855 (herein incorporated by reference).

It is not intended that the present invention is limited to the particular type of cancer. In some embodiments, the invention relates to methods of treating cancer, said cancer including but not limited to, prostate cancer, colon cancer, lung cancer, liver cancer, pancreatic cancer, and brain cancer. In some embodiments, the invention relates to methods of diagnosing cancer, said cancer including but not limited to, prostate cancer, colon cancer, lung cancer, liver cancer, pancreatic cancer, and brain cancer.

A fourth general embodiment of the present invention contemplates a method of identifying an anti-cancer agent comprising: providing; a cell that expresses C43; and a candidate agent suspected of being capable of inhibiting C43 expression; contacting said agent with said cell; and determining whether said agent inhibits an activity of said cell. In one embodiment, the agent is an antibody that binds the C43 protein. In another embodiment, the agent is an shRNA that inhibits C43 RNA. In yet another embodiment, the agent kills the cell. In a further embodiment, said agent inhibits the motility of the cell. In one embodiment, cell motility is determined using a collagen matrix.

In some embodiments, the present invention contemplates a method of identifying an anti-cancer agent comprising: providing a cancer cell(s), and a type I collagen matrix; suspending the cancer cells in the type I collagen matrix; extracting a droplet containing said cancer cells and said matrix; introducing said droplet to a multi-well plate; solidifying said droplet via heating to form a gel; layering said gel with an additional droplet of collagen, and examining properties associate with said cancer cells. In one embodiment, the present invention contemplated a method of identifying an anti-cancer agent comprising: providing a cancer cell(s), and a type I collagen matrix; suspending the cancer cell(s) in the type I collagen matrix; mixing the cancer cells in the matrix with an agent suspected of having anti-cancer activity; and assessing the anti-cancer activity of the agent. In one embodiment, the cancer cells are labeled with a fluorescent dye. In another embodiment, the cancer cells are examined with a fluorimeter. In another embodiment, the cancer cells are examined via fluorescent emission.

The present invention also contemplates kits. In one embodiment, the kit comprises a) a first containing means (e.g. tubes, vials, etc) containing a cell or cell line that expresses the C43 gene; and b) a second containing means containing a candidate agent suspected of being capable of inhibiting C43 expression. In another embodiment, the kit comprises a) a first containing means (e.g. tubes, vials, etc) containing an in vivo C43 transcription and translation system; and b) a second containing means containing a candidate agent suspected of being capable of inhibiting C43 expression. In another embodiment, the kit comprises a) a first containing means (e.g. tubes, vials, etc) containing an in vitro C43 transcription and translation system; and b) a second containing means containing a candidate agent suspected of being capable of inhibiting C43 expression. Such kits may include antibodies, including but not limited to antibodies specific for the C43 gene product, and anti-sense nucleic acid molecules specific for C43 RNA, including but not limited to shRNA nucleic acid molecules. Importantly, the kit is not limited to the particular components of said C43 screening system; a variety of components are contemplated (e.g. ribosomes), as for example in U.S. Pat. No. 7,312,060, herein incorporated by reference.

In one embodiment, the invention provides a method for detecting a cancer cell, comprising detecting increased expression of C43 nucleotide sequence SEQ ID NO:1 compared to a normal cell. In another embodiment, the invention provides a method for detecting a cancer cell, comprising a) providing normal cells and sample cells from a subject, the sample cells suspected to comprise cancer cells, and b) detecting increased expression of C43 nucleotide sequence SEQ ID NO:1 in at least a portion of the sample cells compared to the normal cells, thereby detecting a cancer cell. In one embodiment, the cancer cell is metastatic. In a further embodiment, detecting comprises contacting the endoplasmic reticulum of the cell with antibody that specifically binds to C43 polypeptide sequence (SEQ ID NO:4). In an alternative embodiment, the detecting comprises detecting mRNA encoded by C43 nucleotide sequence (SEQ ID NO:1).

The invention further provides a method for reducing cancer metastasis in a subject, comprising a) providing i) a mammalian subject in need of reducing cancer metastasis, and ii) a composition comprising an agent that reduces the biological activity of C43 protein (SEQ ID NO:4), and b) administering a therapeutic amount of the composition that reduces cancer metastasis to the subject. The invention also provides a method for inhibiting cancer metastasis in a subject, comprising a) providing i) a mammalian subject in need of inhibiting cancer metastasis, and ii) a composition comprising an agent that reduces the biological activity of C43 protein (SEQ ID NO:4), and b) administering a therapeutic amount of the composition under conditions such that cancer metastasis is inhibited in the subject. Also provided herein is a method for treating cancer in a subject, comprising a) providing i) a mammalian subject diagnosed with cancer, and ii) a composition comprising an agent that reduces the biological activity of C43 protein (SEQ ID NO:4), and b) administering a therapeutic amount of the composition to the subject. In one embodiment, the agent that reduces the biological activity of C43 protein comprises an RNA interference sequence that specifically binds to mRNA encoded by the C43 nucleotide sequence (SEQ ID NO:1). Alternatively, the agent that reduces the biological activity of C43 protein comprises an agent that reduces demethylation of the promoter region of C43 nucleotide sequence SEQ ID NO:1. In a further embodiment, the agent that reduces demethylation of the promoter region of C43 nucleotide sequence (SEQ ID NO:1) is selected from the group consisting of S-adenosyl-L-methionine (SAM), 5'-methylthioadenosine (MTA), and methylated DNA binding domain 2 (MBD2) antisense oligonucleotide. In another embodiment, the cancer metastasis is chemo resistant. In a further embodiment, the composition is co-administered with an anti-cancer drug and/or after administration of an anti-cancer drug. In a particular embodiment, the mammalian subject is a human.

Also provided by the invention is a method for detecting a cancer cell, comprising detecting decreased methylation of the promoter region of C43 nucleotide sequence (SEQ ID NO:1) compared to a normal cell. The invention also provides a method for detecting a cancer cell, comprising a) providing normal cells and sample cells from a subject, the sample cells suspected to comprise cancer cells, and b) detecting decreased methylation of the promoter region of C34 nucleotide sequence (SEQ ID NO:1) in at least a portion of the sample cells compared to the normal cells, thereby detecting a cancer cell. In one embodiment, the cancer cell is metastatic. In a further embodiment, the cell is comprised in a sample, exemplified by a sample that is obtained from tissue of a mammal.

The invention also provides a method for reducing cancer metastasis in a subject, comprising a) providing i) a mammalian subject in need of reducing cancer metastasis, and ii) a composition comprising an agent that reduces demethylation of the promoter region of C43 nucleotide sequence (SEQ ID NO:1), and b) administering a therapeutic amount of the composition that reduces cancer metastasis to the subject. The invention further provides a method for inhibiting cancer metastasis in a subject, comprising a) providing i) a mammalian subject in need of inhibiting cancer metastasis, and ii) a composition comprising an agent that reduces demethylation of the promoter region of C43 nucleotide sequence (SEQ ID NO:1), and b) administering a therapeutic amount of the composition under conditions such that cancer metastasis is inhibited in the subject. The invention further provides a method for treating cancer in a subject, comprising a) providing i) a mammalian subject diagnosed with cancer, and ii) a composition comprising an agent that reduces demethylation of the promoter region of C43 nucleotide sequence (SEQ ID NO:1), and b) administering a therapeutic amount of the composition to the subject.

Also provided herein is a method for detecting migrating cells in a sample, comprising a) introducing the sample into a first 3-dimensional matrix, b) contacting the first 3-dimensional matrix with a second 3-dimensional matrix, and c) detecting the presence of cells in the second 3-dimensional matrix, thereby detecting migrating cells in the sample. In one embodiment, the method further comprises d) determining the number of cells in the second 3-dimensional matrix. In an alternative embodiment, the migrating cells comprise cancer cells, exemplified by metastatic cancer cells.

The invention also provides a method for detecting migrating cells in a cell sample, comprising a) providing i) a first well, ii) a cell sample, and iii) a solution, b) mixing the cell sample and the solution to produce a cell suspension, c) introducing the cell suspension into the first well, d) incubating the cell suspension under conditions such that the suspension forms a first 3-dimensional matrix having a first matrix surface that is not in contact with a surface of the first well surface, e) introducing the solution into the first well and in contact with the first matrix surface, f) incubating the solution under conditions such that the solution forms a second 3-dimensional matrix in contact with the first matrix surface, g) incubating the first well that comprises the first 3-dimensional matrix and the second 3-dimensional matrix under conditions for cell migration, and h) detecting the presence of cells in the second 3-dimensional matrix, thereby detecting the presence of migrating cells in the cell sample. In one embodiment, the incubating conditions in step g) comprise contacting the second matrix with cell culture medium. In another embodiment, the culture medium comprises an agent, for determining the agent's effect on cell migration. In a further embodiment, the first well is comprised in a 96-well plate. In another embodiment, the first well comprises a second well, and the introducing of step c) is into the second well.

The invention further provides a method for identifying a test agent as reducing cell migration, comprising a) providing i) a target cell that expresses C43 protein (SEQ ID NO:4), and ii) a test agent, b) contacting the test agent with the target cell to produce a contacted cell, and c) detecting migration by the contacted cell, wherein reduced migration of the contacted cell compared to migration of a control cell in the absence of the test agent identifies the test agent as reducing migration of a cell. The invention also provide a method for identifying a test agent capable of reducing cell migration, comprising a) providing i) a target cell that expresses C43 protein (SEQ ID NO:4), and ii) a test agent, b) contacting the test agent with the target cell to produce a contacted cell, and c) detecting migration by the contacted cell, wherein reduced migration of the contacted cell compared to migration of a target cell in the absence of the test agent identifies the test agent as reducing migration of a cell. Additionally provided herein is a method for identifying a test agent capable of reducing cell migration, comprising a) providing i) a target cell that expresses C43 protein (SEQ ID NO:4), ii) a control cell, and iii) a test agent, b) contacting the test agent with the target cell to produce a contacted cell, and c) detecting migration by the contacted cell, wherein reduced migration of the contacted cell compared to migration of the control cell in the absence of the test agent identifies the test agent as reducing migration of a cell. In one embodiment, detecting migration of step c) comprises detecting migration in a 3-dimensional matrix. In a particular embodiment, the target cell is a cancer cell. In a further embodiment, the target cell is a transgenic cell. In yet a further embodiment, the transgenic cell is selected from the group consisting of cancer cell and normal cell.

The invention also provides a method for identifying a nucleotide sequence of interest as altering cell migration, comprising a) providing a cell comprising a nucleotide sequence of interest, b) introducing the transgenic cell into a first 3-dimensional matrix, c) contacting the first 3-dimensional matrix with a second 3-dimensional matrix, and d) detecting migration of the transgenic cells from the first 3-dimensional matrix to the second 3-dimensional matrix, wherein altered migration of the transgenic cells compared to migration of a control cell lacking the nucleotide sequence of interest identifies the nucleotide sequence of interest as altering cell migration. The invention also provides a method for identifying a nucleotide sequence of interest as altering cell migration, comprising a) providing a transgenic cell comprising a nucleotide sequence of interest and a control cell lacking the nucleotide sequence of interest, b) introducing the transgenic cell into a first 3-dimensional gel that comprises type I collagen, c) contacting the first 3-dimensional gel with a second 3-dimensional gel comprising type I collagen, and d) detecting migration of the transgenic cells from the first 3-dimensional gel to the second 3-dimensional gel, wherein altered migration of the transgenic cells compared to migration of the control cell lacking the nucleotide sequence of interest identifies the nucleotide sequence of interest as altering cell migration. In one embodiment, the cell is transgenic and the nucleotide sequence of interest is heterologous to the cell.

The invention also provides multi-well platform comprising a plurality of wells, wherein at least one well has a surface that comprises a second well. In one embodiment, the well surface is at the bottom of the at least one well. In another embodiment, the second well comprises a 3-dimensional matrix that contains cells. In a particular embodiment, the plurality of wells is arranged in a two-dimensional linear array pattern. In an exemplary embodiment, the plurality of wells is from 24 wells to 10,000 wells, such as a multiple of 96.

DEFINITIONS

To facilitate the understanding of this invention a number of terms are defined below. Terms defined herein (unless otherwise specified) have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, terms defined in the singular are intended to include those terms defined in the plural and vice versa.

As used herein, the terms "patient" and "subject" refer to a human or animal who is ill or who is undergoing treatment for disease, but does not necessarily need to be hospitalized. For example, out-patients and persons in nursing homes are "patients."

As used herein, the terms "treat", "treating", "treatment" and grammatical equivalents refers to combating a disease or disorder, as for example in the management and care of a patient. In one embodiment, treating a disease (e.g., cancer, metastasis, etc.) includes reducing one or more symptoms of the disease.

As used herein, the terms "diagnose", "diagnosis" or "diagnosing" refers to the recognition of a disease by its signs and symptoms (e.g., resistance to conventional therapies), or genetic analysis, pathological analysis, histological analysis, and the like.

As used herein, the term "diagnostic" refers to a compound that assists in the identification and characterization of a health or disease state. The diagnostic can be used in standard assays as is known in the art.

As used herein, the terms "localize" or "localized" refer to confinement to an area or volume concomitant with the area or volume occupied by the cell, organelle, molecule, protein, or nucleic acid such as DNA or RNA sought to be located in reference to the rest of the tissue (with respect to cells) or within a cell.

As used herein, the term "hybridize", "hybridization", or "hybridizing" refers to the pairing of complementary nucleic acids resulting in the formation of a partially or wholly complementary nucleic acid duplex by association of single strands of nucleic acid. Hybridization usually occurs between DNA and RNA strands or previously unassociated DNA strands, but also between two RNA strands; and may be used to detect and isolate specific sequences, measure homology, or define other characteristics of one or both strands. Hybridization and the strength of hybridization (i.e., the strength of the association between the nucleic acids) is impacted by such factors as the degree of complementary between the nucleic acids, stringency of the conditions involved, the melting temperature of the formed hybrid, and the G:C ratio within the nucleic acids.

As used herein, the terms "inhibit", "suppress" or "silence" refer to the act of diminishing, alleviating, preventing, reducing or eliminating. For example, a compound that inhibits cancer may kill all cancerous cells or prevent, arrest or slow further cancerous cell growth. These terms find use in both in vitro as well as in vivo systems, as for example the inhibiting the growth or proliferation of cancer cells. It is not necessary that there be complete inhibition, suppression or silencing, for the present application it is sufficient for there to be some inhibition, suppression or silencing.

As used herein, the term "downregulate" or "downregulation" refers to a decrease, relative to an appropriate control, in the amount of a given molecule, protein, gene product, or nucleic acid such as DNA or RNA due to exposure to or contact with an inhibitor.

As used herein, the terms "proliferate", "proliferation" and grammatical equivalents refers to increasing in number by growth, reproduction or multiplication of similar forms, such as the reproduction of similar cells.

As used herein, the term "overexpress", "overexpressing" and grammatical equivalents, refers to the production of a gene product at levels that exceeds production in normal or control cells. The term "overexpression" or "highly expressed" may be specifically used in reference to levels of mRNA to indicate a higher level of expression than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in all tissues) present in each sample can be used as a means of normalizing or standardizing the mRNA-specific signal observed on Northern blots. Overexpression may likewise result in elevated levels of proteins encoded by said mRNAs.

As used herein, the term "disseminate" or "disseminated" refers to being scattered or distributed over a range (in area or volume), whether evenly or unevenly, such as being spread over a large area of a body, tissue, or organ.

As used herein, the term "gene" refers to the deoxyribonucleotide sequences comprising the coding region of a gene, including sequences located adjacent to the coding region on both the 5' and 3' ends for a distance of several kb on either end such that the gene corresponds to the length of the full-length mRNA. The sequences located 5' of the coding region and present on the mRNA are referred to as 5' non-translated sequences. The sequences located 3' or downstream of the coding region and present on the mRNA are referred to as 3' non-translated sequences. A genomic form or clone of a gene contains coding sequences, termed exons, alternating with non-coding sequences termed "introns" or "intervening regions" or "intervening sequences." Introns are segments of a gene that are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. In addition to containing introns, genomic forms of a gene may also include sequences located on both the 5' and 3' end of the sequences that are not present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

As used herein, the term "coding region" refers to the nucleotide sequences that encode the amino acids found in the nascent polypeptide as a result of translation of an mRNA molecule. The coding region may be bounded, for examples in eukaryotes, on the 5' side by the nucleotide triplet "ATG"

which encodes the initiator methionine and on the 3' side by one of the three triplets that specify stop codons (i.e., TAA, TAG, TGA).

As used herein, the term "protein" refers to the sequence of amino acids encoded by a specific gene comprising any of a group of complex organic compounds, which contain carbon, hydrogen, oxygen, nitrogen, and usually sulfur, the characteristic element being nitrogen. Twenty different amino acids are commonly found in proteins, and each protein has a unique genetically defined amino acid sequence, which determines its specific shape and function.

As used herein, the term the terms "peptide", "peptide sequence", "amino acid sequence", "polypeptide", and "polypeptide sequence" are used interchangeably to refer to at least two amino acids or amino acid analogs that are covalently linked by a peptide bond or an analog of a peptide bond. The term "peptide" includes oligomers and polymers of amino acids or amino acid analogs. The term "peptide" also includes molecules that generally contain from about two (2) to about twenty (20) amino acids. The term "peptide" also includes molecules that are commonly referred to as polypeptides, which generally contain from about twenty (20) to about fifty amino acids (50). The term "peptide" also includes molecules that are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A "synthetic peptide" is a peptide that is produced by artificial means in vitro.

As used herein, the term "antibody" refers to polyclonal and monoclonal antibodies. Polyclonal antibodies, which are formed in the animal as the result of an immunological reaction against a protein of interest or a fragment thereof, can be readily isolated from the blood using well-known methods and purified, for example by column chromatography. Monoclonal antibodies can also be prepared using known methods (See, Winter and Milstein, Nature, 349, 293-299, 1991). As used herein, the term "antibody" encompasses recombinantly prepared, and modified antibodies and antigen-binding fragments thereof, such as chimeric antibodies, humanized antibodies, multifunctional antibodies, bi-specific or oligo-specific antibodies, single-stranded antibodies and antibody fragments (e.g. Fab, $Fab_2$, etc.). The term "reactive" when used in reference to an antibody indicates that the antibody is capable of binding an antigen of interest.

As used herein, the term "endoplasmic reticulum" or "E.R." refers to an ultramicroscopic organelle present in nearly all cells of higher plants and animals, consisting of a more or less continuous system of membrane-bound cavities throughout the cytoplasm of a cell. Two forms of "endoplasmic reticulum" have been distinguished: i) rough (i.e., granular) E.R., which bears large numbers of ribosomes on the outer surface of its membrane and is basophilic, and ii) smooth E.R., which contains no ribosomes and has no distinctive staining properties.

As used herein, the term "lymph node(s)" refers to any of the accumulations of lymphoid tissue organized as definite lymphoid organs, situated along the course of lymphatic vessels, and consisting of an outer cortical and an inner medullary part. The lymph nodes are the main source of lymphocytes of the peripheral blood and, as part of the reticuloendothelial system, serve as a defense mechanism by removing noxious agents, such as bacteria and toxins, and play a role in antibody production.

As used herein, the term "vasculature" refers to any specific part of the circulatory system, such as the channels through which fluids of the body circulate; often restricted to the vessels conveying blood.

As used herein, the term "immunodeficient" refers to a state in which the immune system's ability to fight infectious disease is compromised or entirely absent. Immunodeficiency may result from administration of immunosuppressive drugs, irradiation, malnutrition, genetic abnormality, or a disease process. An individual with an immunodeficiency of any kind is said to be immunocompromised, and may be particularly vulnerable to opportunistic infections, in addition to normal infections.

As used herein, the term "shRNA" or "short hairpin RNA" refers to a sequence of ribonucleotides comprising a single-stranded RNA polymer that makes a tight hairpin turn on itself to provide a "double-stranded" or duplexes region. shRNA can be used to silence gene expression via RNA interference. shRNA hairpin is cleaved into short interfering RNAs (siRNA) by the cellular machinery and then bound to the RNA-induced silencing complex (RISC). It is believed that the complex inhibits RNA as a consequence of the complexed siRNA hybridizing to and cleaving RNAs that match the siRNA that is bound thereto.

As used herein, the term "RNA interference" or "RNAi" refers to the silencing or decreasing of gene expression by shRNA, RNAi and/or siRNA. "RNA interference sequence" refers to an shRNA sequence, RNAi sequence and/or siRNA sequence that specifically binds to a target mRNA sequence. RNA interference is the process of sequence-specific, post-transcriptional gene silencing in animals and plants, initiated by shRNA and/or siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. It is not necessary that there be complete inhibition, for the present application it is sufficient for there to be some inhibition. RNAi inhibits the gene by compromising the function of a target RNA, completely or partially. Both plants and animals mediate RNAi by the RNA-induced silencing complex (RISC); a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. Cell Biol. 13(2): 244-248 (2001)) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

As used herein, the term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand", and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in both vertebrates and invertebrates, and in triggering sequence-specific RNA degradation during posttranscriptional gene silencing in plants.

As used herein, the term "mRNA" or "messenger RNA" refers to RNA molecules that serve as templates for protein synthesis; in eukaryotes mRNAs have characteristic posttranscriptional modifications including the 5'-cap and poly-A tail. The base sequence of an mRNA transcript completely specifies the corresponding polypeptide amino acid sequence.

As used herein, a "nucleic acid" is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide", as used herein, is a nucleic acid containing a sequence that is greater than about 100 nucleotides in length. An "oligonucleotide", as used herein, is a short polynucleotide or a portion of a polynucleotide. An "oligonucleotide" typically contains a sequence of about two to about one hundred bases. The word "oligo" is sometimes used in place of the word "oligonucleotide". Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a nucleic acid at which a new linkage would be to a 5' pentose carbon is its 5' terminal nucleotide (by convention sequences are written, from right to left, in the 5' to 3' direction). The end of a nucleic acid at which a new linkage would be to a 3' pentose carbon is its 3' terminal nucleotide. A terminal nucleotide, as used herein, is the nucleotide at the end position of the 3'- or 5'-terminus. DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, the term "luciferase" refers to one of a variety of monooxygenases that catalyze a reaction producing bioluminescence in certain marine crustaceans, fish, bacteria, and insects. The luciferase enzyme is a flavoprotein that oxidizes luciferin to an electronically excited compound that emits energy in the form of light. The color of light emitted varies with the organism.

As used herein, the term "polymerase chain reaction" or "PCR" refers to the method of K. B. Mullis disclosed and claimed in U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration, of an amplified segment of the desired target sequence. The length of the amplified segment of the desired target sequence is determined by the relative positions of the primers with respect to each other, and therefore, this length is a controllable parameter. By virtue of the repetitive aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "concanavalin A" refers to a mitogen that stimulates cell division. As used herein, a "mitogen" is a chemical substance, often a protein, which encourages cells to divide by triggering-signal transduction pathways in which mitogen-activated protein kinase is involved. Mitogens are often used to stimulate proliferation of cells, including but not limited to lymphocytes.

As used herein, the term "data mining" refers to the extraction of information implicitly stored or captured in large databases, data warehouses, Internet websites, other massive information repositories, or data streams.

As used herein, the term "DNA microarray database" refers to an information repository from a collection of microscopic DNA spots, commonly representing single genes, arrayed on a solid surface. Qualitative or quantitative measurements with DNA microarrays utilize the selective nature of DNA-DNA or DNA-RNA hybridization under high-stringency conditions and fluorophore-based detection. DNA arrays are commonly used for expression profiling, or for comparative genomic hybridization.

As used herein, the term "intravenous" refers a mode of administration of a substance such as a drug or a nutrient solution, within or into a vein.

As used herein, the term "intrathecal" refers to a mode of administration of a substance such as a drug or a nutrient solution through the theca of the spinal cord into the subarachnoid space.

As used herein, the term "inhalation" refers to a mode of administration of a substance such as a drug or a nutrient solution by the nasal or oropharyngeal respiratory route for local or systemic effect by drawing an aerosol into the lungs with the breath.

As used herein, an "aerosol" is defined as a suspension of liquid or solid particles of a substance (or substances) in a gas. The present invention contemplates the use of both atomizers and nebulizers of various types. An "atomizer" is an aerosol generator without a baffle, whereas a "nebulizer" uses a baffle to produce smaller particles.

As used herein, the term "intramuscular" refers to a mode of administration of a substance such as a drug or a nutrient solution by directly introducing the compound within the substance of a muscle.

As used herein, the term "subcutaneous" refers to a mode of administration of a substance such as a drug or a nutrient solution by introducing the compound beneath the skin (intradermally or subdermally) such that the body absorbs it.

As used herein, the term "sample" is used in its broadest sense. In one sense, it is meant to include a specimen or culture obtained from a biological source. Biological samples include blood products, such as plasma, serum and the like. Such examples are not however to be construed as limiting the sample types applicable to the present invention.

As used herein, the terms "cancer cell" and "tumor cell" refer to a cell undergoing early, intermediate or advanced stages of multi-step neoplastic progression as previously described (Pitot et al., Fundamentals of Oncology, 15-28 (1978)), herein incorporated by reference. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as a "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell". A dysplastic cell resembles an immature epithelial cell, is generally spatially disorganized within the tissue and loses its specialized structures and functions. During the intermediate stages of neoplastic progressions an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive i.e., they either invade adjacent tissues, or are shed from the primary site and circulate through the blood and lymph to other locations in the body where they initiate secondary cancers. The term "cancer" or "neoplasia" refers to a plurality of cancer cells. "Aggressive cancer cells" are cancer cells that are capable of metastasizing.

As used herein, the term "cancer grade" refers to the morphology of abnormal cancer cells and how quickly the tumor is likely to grow and spread. Specific factors used to determine tumor grade vary with each type of cancer, but generally include the structure and growth pattern of the cells. Tumor grade is commonly described by four degrees of severity: Grades 1, 2, 3, and 4. The cells of Grade 1 tumors typically resemble normal cells, and tend to grow and multiply slowly. Grade 1 tumors are generally considered the least aggressive in behavior. Conversely, the cells of Grade 3 or Grade 4 tumors typically do not look like normal cells of the same type. Grade 3 and 4 tumors tend to grow rapidly and spread faster than tumors with a lower grade.

As used herein, the term "cancer stage" or "stage of cancer" refers to a qualitative or quantitative assessment of the level of advancement of a cancer, including the extent or severity of the cancer, based on factors such as the location of the primary tumor, tumor size, number of tumors, and lymph node involvement. Criteria used to determine the stage of a cancer include, but are not limited to, the size of the tumor, whether the tumor has spread to other parts of the body and where the cancer has spread (e.g., within the same organ or region of the body or to another organ).

As used herein, the term "anti-cancer" or "anti-cancer drug" refers to a drug, substance, compound or chemical formulation that reduces one or more symptoms of cancer. Thus in one embodiment, an anti-cancer drug has the ability to inhibit, suppress, silence and/or kill a cancerous cell. It is not necessary for the anti-cancer drug to produce complete inhibition, suppression or silencing, for the present application it is sufficient for there to be some inhibition, suppression or silencing.

As used herein, the term "recurrence" refers to the return of symptoms and/or disease after a remission.

As used herein, the term "Her-2 status" refers to the level of Her-2 protein on the surface of certain cancer cells. HER2 is a receptor for a particular growth factor called human epidermal growth factor, which occurs naturally in the body. When human epidermal growth factor attaches itself to HER2 receptors on breast cancer cells, it can stimulate the cells to divide and grow. Some breast cancer cells have a lot more HER2 receptors than others. In this case, the tumor is described as being HER2-positive. Tumors that are HER2-positive tend to grow more quickly than other types of breast cancer. Knowing if a cancer is HER2-positive can sometimes affect the choice of treatment. It is thought that about 1 in 5 women with breast cancer will have HER2-positive tumors.

As used herein, the terms "cell line" and "immortalized cell" refer to a cell that is capable of a greater number of cell divisions in vitro before cessation of proliferation and/or senescence as compared to a primary cell from the same source. A cell line includes, but does not require, that the cells be capable of an infinite number of cell divisions in culture. The number of cell divisions may be determined by the number of times a cell population may be passaged (i.e., subcultured) in vitro culture. Passaging of cells is accomplished by methods known in the art. Cell lines may be generated spontaneously or by transformation. A "spontaneous cell line" is a cell line that arises during routine culture of cells. A "transformed cell line" refers to a cell line that is generated by the introduction of a "transgene" comprising nucleic acid (usually DNA) into a primary cell or into a finite cell line by means of human intervention.

As used herein, the term "tumor progression" refers to any event which first promotes the transition of a normal non-neoplastic cell to a cancerous neoplastic one. Such events include ones that occur prior to the onset of neoplasia, and which predispose, or act as a step towards, the cell becoming neoplastic. These events can, for example, include ones that cause a normal cell to exhibit a pre-neoplastic phenotype. Second, such events can also include ones that promote unhindered cell proliferation and/or tumor cell invasion of adjacent tissue. Third, tumor progression can include events that promote the transition of a tumor cell to a metastatic state.

As used herein, the term "carcinoma" refers to a malignant new growth made up of epithelial cells tending to infiltrate the surrounding tissues and give rise to metastases.

As used herein, the term "MDA-MB-435 cells" refers to a human breast cancer cell line derived from mammary gland primary ductal carcinoma.

As used herein, the term "MDA-MB-231 cells" refers to a human breast adenocarcinoma cell line derived from a metastatic pleural effusion, a collection of fluid in the pleural space of a metastatic human breast carcinoma. As used herein, the "pleural space" is the region between the outer pleural membrane (attached to the chest wall) and the inner pleural membrane (covering the lungs and other internal organs).

As used herein, the term "COS-1 cells" refers to an African green monkey kidney fibroblast-like cell line.

As used herein, the term "MCF-7 cells" refers to a human breast cancer cell line derived from mammary gland epithelial adenocarcinoma. The MCF7 line retains several characteristics of differentiated mammary epithelium including ability to process estradiol via cytoplasmic estrogen receptors and the capability of forming domes.

As used herein, "human HT1080 fibrosarcoma cells" refers to a human derived connective tissue fibrosarcoma cell line.

As used herein, the term "NIH 3T3 cells" refers to a mouse embryonic fibroblast cell line.

As used herein, the term "PC3 cells" refers to a human prostate cancer cell line.

As used herein, the term "LNCaP cells" refers to a human prostate cancer cell line originally isolated from a metastatic lesion of human prostate adenocarcinoma. Unlike PC3 cells, the growth of LNCaP cells is androgen-dependent.

As used herein, the term "fibrosarcoma" refers to a malignant tumor composed of cells and fibers derived from fibroblasts, which produce collagen but otherwise lack cellular differentiation. Fibrosarcomas are grossly grayish white and firm, invade locally, and metastasizes hematogenously.

As used herein, the term "fibroblast" refers to a flat elongated connective tissue cell with cytoplasmic processes at each end, having a flat, oval, vesicular nucleus. Fibroblasts form the fibrous tissues in the body, including tendons, aponeuroses, supporting and binding tissues of all sorts. A fibroblastoma is a tumor arising from fibroblasts, divided into fibromas and fibrosarcomas.

As used herein, the term "epithelial" refers to the cells of the epithelium, the covering of internal and external surfaces of the body, including the lining of vessels and other small cavities. The epithelium is classified based on the layers' depth and the shape of the superficial cells.

As used herein, the terms "metastasis", "metastatic" and "metastasize" refer to the transfer of abnormal cells from one primary site, organ or location to another not directly connected with it to form new foci of disease due the transfer of cells, as in malignant tumors. The capacity to metastasize is a characteristic of all malignant tumors.

As used herein, the term "mode" refers to a manner, way, or method of acting. As for example, one might employ a variety of "modes of administering" a therapeutic compound to a patient.

As used herein, the term "confocal microscopy" refers to an optical imaging technique used to increase contrast and/or reconstruct three-dimensional images by eliminating out-of-focus light in specimens that are thicker than the focal plane. Since only light within the focal plane is detected, image quality is better than standard wide-field images.

As used herein, the term "BLAST" or "Basic Local Alignment Search Tool" refers to a program that identifies regions of local similarity between biological sequences by comparing nucleotide or protein sequences to sequence databases and calculating the statistical significance of matches. BLAST can be used to infer functional and evolutionary relationships between sequences as well as help identify members of gene families.

As used herein, the term "RACE" or "Rapid Amplification of cDNA Ends" refers to a technique used in molecular biology to obtain the partial sequence of an RNA transcript. RACE results in the production of a DNA copy of the RNA sequence of interest, using reverse transcription and followed by PCR amplification of the DNA copy. The amplified DNA copy is then sequenced to obtain a partial sequence of the original RNA. RACE can provide the sequence of an RNA transcript from a small known sequence within the transcript to the 5' end (5' RACE) or 3' end (3' RACE) of the RNA.

As used herein, the term "collagen" refers to a group of fibrous proteins that occur in vertebrates as the chief constituent of connective tissue fibrils and in bones and yield gelatin and glue upon boiling with water. Collagen is the major insoluble fibrous structural protein in the extracellular matrix and connective tissue, has great tensile strength, and is the main component of fascia, cartilage, ligaments, tendons, bone and teeth. Type I collagen is present in scar tissue, tendons, skin, artery walls, fibrocartilage, and the organic part of bones and teeth. A "collagen matrix", as used herein, refers to a mixture of Type-I collagen and a gel (including but not limited to gelatin, agar, agarose, and polyacrylamide) that can produce a 3-dimensional structure after solidifying. Type I collagen is commercially available (BectonDickinson Biosciences, CA) and may be prepared using methods known in the art (e.g., from tendons).

As used herein, the term "nutraceutical" refers to extracts of foods claimed to have a medicinal effect on human health, including the prevention and/or treatment of a disease.

As used herein, the term "phenotypic screening" refers to the analysis of a substance or compound based on its effect(s) on the structure or physiological activities of cells or tissues. Since phenotypic screening provides information about effects on cell or tissue structure or function it may be used at an early stage of examination to eliminate compounds that are toxic or do not produce the desired cellular response.

As used herein, the term "green fluorescent protein" or "GFP" refers to a protein originally isolated from the jellyfish that fluoresces green when exposed to blue light. In cell and molecular biology, the GFP gene is frequently used as a reporter of expression. In modified forms it has been used to make biosensors. The GFP gene can be introduced into organisms and maintained in their genome. Since GFP does not generally harm living cells it may be used for a variety of in vitro and in vivo applications. Proteins that fluoresce to produce other colors are also available, in particular blue fluorescent protein (BFP), cyan fluorescent protein (CFP) and yellow fluorescent protein (YFP).

As used herein, the term "pharmacokinetic" refers to the determination of the fate a substance (i.e. nutrients, metabolites, hormones, toxins, drugs etc.) after being administered to a living organism. Pharmacokinetics examines the effect the organism has on the administered substance, and is often divided into several areas including, but not limited to, the extent and rate of absorption, distribution, metabolism and excretion.

As used herein, the term "DAPI" or "4',6-diamidino-2-phenylindole" refers to a fluorescent stain that binds strongly to DNA and is used extensively in fluorescence microscopy. Since DAPI will pass through an intact cell membrane, it may be used to stain both live and fixed cells.

As used herein, the term "dimethyl sulfoxide" or "DMSO" refers to is a chemical compound with the formula $(CH_3)_2SO$.

As used herein, the term "xenograft" refers to the surgical transplant or graft of tissue or organs from an individual of one species, genus or family into an individual of another species, genus, or family.

As used herein, the term "orthotopic" or "orthotopic implantation" refers to a cell or tissue transplant grafted into its normal place in the body.

As used herein, the term "half-life" refers to the time interval required for a quantity to decay to half of its initial value. As for example, the time it takes a substance or compound to lose half of its pharmacologic, physiologic, or radiologic activity.

As used herein, the term "kit" is used in reference to a combination of reagents and other materials. It is contemplated that the kit may include reagents such as antibodies, control proteins, as well as testing containers (e.g., microtiter plates, etc.). It is not intended that the term "kit" be limited to a particular combination of reagents and/or other materials.

As used herein, the term "administer" and grammatical equivalents thereof means to mete out or dispense a remedy. For example, in medicine "administering" refers to the act of giving a treatment, such as a drug, to a patient. It may also refer to the may in which a treatment is given, as for example the dose or frequency of administration. The simultaneous administration of more than one treatment to a patient may be referred to as "co-administration".

As used herein, the term "library" refers to a structurally diverse population of randomized candidate bioactive agents such as proteins (which herein includes proteins, peptides and polypeptides), nucleic acids, small organic or inorganic molecules and chemical moieties to be screened for binding to a target molecule. A library provides a sufficient range of candidate bioactive agent diversity to allow binding to a particular target. Accordingly, a library should be large enough so that at least one of its members will have a structure that gives it affinity for the target.

As used herein, the term "chemoresistant" or "chemoresistance" refers to cancer cell(s) that do not respond to the cell-killing effects of anti-cancer drugs. The cancerous cell(s) may be resistant at the beginning of treatment, or may become resistant during the course of the treatment.

As used herein, the term "Paclitaxel" refers to a mitotic inhibitor used in cancer chemotherapy that interferes with normal microtubule breakdown during cell division. Paclitaxel is used to treat a variety of cancers, including but not limited to, lung cancer, ovarian cancer, breast cancer, and head and neck cancer.

The term "cancer" is used herein to refer to a malignant neoplasm, which may or may not be metastatic. Malignant neoplasms that can be diagnosed and/or treated using the methods of the invention include, for example, carcinomas such as lung cancer, breast cancer, prostate cancer, cervical cancer, pancreatic cancer, colon cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia. Malignant neoplasms are further exemplified by sarcomas (such as osteosarcoma and Kaposi's sarcoma).

"C43 protein" and "KIAA1199 protein" are used interchangeably to refer to an amino acid sequence (such as SEQ ID NO:4 of FIG. 10) encoded by the nucleotide sequence GenBank No. AB103330 and/or SEQ ID NO:1 of FIG. 2.

"Subject" "and "animal" interchangeably refer to any multicellular animal, preferably a mammal. Mammalian subjects include humans, non-human primates, murines, ovines, bovines, ruminants, lagomorphs, porcines, caprines, equines, canines, felines, ayes, etc.). Thus, mammalian subjects are exemplified by mouse, rat, guinea pig, hamster, ferret and chinchilla.

"Subject in need of reducing one or more symptoms of" a disease, e.g., in need of reducing cancer metastasis and/or in need of reducing one or more symptoms of cancer, includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable).

The terms "therapeutic amount," "pharmaceutically effective amount," "therapeutically effective amount," "biologically effective amount," and are used interchangeably herein to refer to an amount which is sufficient to achieve a desired result, whether quantitative or qualitative. In particular, a pharmaceutically effective amount is that amount that results in the reduction, delay, and/or elimination of undesirable effects (such as pathological, clinical, biochemical and the like) in the subject that are associated with disease. For example, a "therapeutic amount that reduces cancer metastasis" is an amount that that reduces, delays, and/or eliminates one or more symptoms of cancer metastasis. Also, a "therapeutic amount that reduces one or more symptoms of cancer" is an amount that reduces, delays, and/or eliminates one or more symptoms of cancer. The actual amount encompassed by the term "therapeutic amount" will depend on the route of administration, the type of subject being treated, and the physical characteristics of the specific subject under consideration. These factors and their relationship to determining this amount are well known to skilled practitioners in the medical, veterinary, and other related arts and are further discussed herein.

The terms "sample" and "specimen" as used herein are used in their broadest sense to include any composition that is obtained and/or derived from biological or environmental source, as well as sampling devices (e.g., swabs) that are brought into contact with biological or environmental samples. "Biological samples" include those obtained from an animal, body fluids such as urine, blood, plasma, fecal matter, cerebrospinal fluid (CSF), semen, sputum, and saliva, as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like.

The terms "reduce," "inhibit," "diminish," "suppress," "decrease," and grammatical equivalents (including "lower," "smaller," etc.) when in reference to the level of any molecule (e.g., amino acid sequence such as C43 protein, antibody that specifically binds to C43 protein, etc., and nucleic acid sequence such as those encoding any of the polypeptides described herein), cell (e.g., cancer cell, normal cell, metastatic cell, etc.), and/or phenomenon (e.g., cell migration activity, cell invasion activity, gene expression (as measured by expression of its mRNA and/or protein products), methylation, cancer metastasis (e.g., metastasis incidence, metastasis number, the rate of increase in metastasis tumor size such as diameter and/or volume), cancer and/or cancer symptoms (e.g., tumor incidence, tumor number, the rate of increase in tumor size, such as tumor diameter and/or volume, the presence of molecular markers of cancer cells such as oncogenes, the presence of cancer metastases, cell proliferation, cell differentiation, cell death, cell apoptosis, cell viability, cell survival, binding to a molecule, affinity of binding, expression of a nucleic acid sequence, transcription of a nucleic acid sequence, enzyme activity, etc.) in a first sample (or patient) relative to a second sample (or in a treated patient), mean that the quantity of molecule, cell, and/or phenomenon in the first sample (or patient) is lower than in the second sample (or in a treated patient) by any amount that is statistically significant using any art-accepted statistical method of analysis. In one embodiment, the reduction may be determined subjectively, for example when a patient refers to their subjective perception of disease symptoms, such as pain, fatigue, difficulty in breathing, clarity of vision, nausea, etc. In another embodiment, the quantity of molecule, cell, and/or phenomenon in the first sample is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in a second sample.

The terms "increase," "elevate," "raise," and grammatical equivalents (including "higher," "greater," etc.) when in reference to the level of any molecule (e.g., amino acid sequence such as C43 protein, antibody that specifically binds to C43 protein, etc., and nucleic acid sequence such as those encoding any of the polypeptides described herein), cell (e.g., cancer cell, normal cell, metastatic cell, etc.), and/or phenomenon (e.g., cell migration activity, cell invasion activity, gene expression (as measured by expression of its mRNA and/or protein products), methylation, cancer metastasis (e.g., metastasis incidence, metastasis number, the rate of increase in metastasis tumor size such as diameter and/or volume), cancer and/or cancer symptoms (e.g., tumor incidence, tumor number, the rate of increase in tumor size, such as tumor diameter and/or volume, the presence of molecular markers of cancer cells such as oncogenes, the presence of cancer metastases, cell proliferation, cell differentiation, cell death, cell apoptosis, cell viability, cell survival, binding to a molecule, affinity of binding, expression of a nucleic acid sequence, transcription of a nucleic acid sequence, enzyme activity, etc.) in a first sample (or patient) relative to a second sample (or treated patient), mean that the quantity of the molecule, cell and/or phenomenon in the first sample (or patient) is higher than in the second sample (or in a treated patient) by any amount that is statistically significant using any art-accepted statistical method of analysis. In one embodiment, the increase may be determined subjectively, for example when a patient refers to their subjective perception of disease symptoms, such as pain, fatigue, difficulty in breathing, clarity of vision, nausea, etc. In another embodiment, the quantity of molecule, cell, and/or phenomenon in the first sample is higher by any numerical percentage, such as at least 10% greater than, at least 25% greater than, at least 50% greater than, at least 75% greater than, and/or at least 90% greater than the quantity of the same molecule, cell and/or phenomenon in a second sample. In yet a further embodiment, the quantity of molecule, cell, and/or phenomenon in the first sample is higher by any numerical amount from 5 fold to 1000 fold, including from 5 fold to 500 fold, 10 fold to 400 fold, from 20 fold to 300 fold, from 30 fold to 200 fold, from 40 fold to 200 fold, from 50 fold to 200 fold.

The terms "change" and/or "alter" when in reference to the level of any molecule (e.g., amino acid sequence such as C43 protein, antibody that specifically binds to C43 protein, etc., and nucleic acid sequence such as those encoding any of the polypeptides described herein), cell (e.g., cancer cell, normal cell, metastatic cell, etc.), and/or phenomenon (e.g., cell migration activity, cell invasion activity, gene expression (as measured by expression of its mRNA and/or protein products), methylation, cancer metastasis (e.g., metastasis incidence, metastasis number, the rate of increase in metastasis tumor size such as diameter and/or volume), cancer and/or cancer symptoms (e.g., tumor incidence, tumor number, the rate of increase in tumor size, such as tumor diameter and/or volume, the presence of molecular markers of cancer cells such as oncogenes, the presence of cancer metastases, cell proliferation, cell differentiation, cell death, cell apoptosis, cell viability, cell survival, binding to a molecule, affinity of binding, expression of a nucleic acid sequence, transcription of a nucleic acid sequence, enzyme activity, etc.) refers to a quantitative increase or decrease. Alternatively, "change" refers to a qualitative alteration in a phenomenon or structure.

The term "substantially the same" when in reference to the level of any molecule (e.g., amino acid sequence such as C43 protein, antibody that specifically binds to C43 protein, etc., and nucleic acid sequence such as those encoding any of the polypeptides described herein), cell (e.g., cancer cell, normal cell, metastatic cell, etc.), and/or phenomenon (e.g., cell migration activity, cell invasion activity, gene expression (as measured by expression of its mRNA and/or protein products), methylation, cancer metastasis (e.g., metastasis incidence, metastasis number, the rate of increase in metastasis tumor size such as diameter and/or volume), cancer and/or cancer symptoms (e.g., tumor incidence, tumor number, the rate of increase in tumor size, such as tumor diameter and/or volume, the presence of molecular markers of dancer cells such as oncogenes, the presence of cancer metastases, cell proliferation, cell differentiation, cell death, cell apoptosis, cell viability, cell survival, binding to a molecule, affinity of binding, expression of a nucleic acid sequence, transcription of a nucleic acid sequence, enzyme activity, etc.) in a first sample relative to a second sample, means that the difference in quantity of measurement or phenomenon in the first sample compared to the second sample is not statistically significant. In one embodiment, the difference in quantity of measurement or phenomenon between the first and second samples is less than 10%.

Reference herein to any numerical range expressly includes each numerical value (including fractional numbers and whole numbers) encompassed by that range. To illustrate, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes whole numbers of 5, 6, 7, 8, 9, and 10, and fractional numbers 5.1, 5.2, 5.3, 5.4, 5.5, 5.6, 5.7, 5.8, 5.9, etc.

BRIEF DESCRIPTION OF THE DRAWINGS

For a more complete understanding of the features and advantages of the present invention, reference is now made to the detailed description of the invention along with the accompanying figures.

FIG. 2 depicts SEQ ID NO:1. The full length of C43 cDNA including the open reading frame of the C43 gene. Nucleotides 1735-1757 are underlined to indicate the location of SEQ ID NO: 2.

FIG. 3 depicts SEQ ID NO:2. The 21-nucleotide C43 shRNA molecule that spans nucleotides 1735-1757 of the open reading frame of SEQ ID NO: 1.

FIG. 4 depicts SEQ ID NO:3. The 21-nucleotide luciferase shRNA molecule that spans nucleotides 103-123 of the luciferase gene.

FIG. 10 shows the amino acid sequence of C43 protein (SEQ ID NO:4).

FIG. 17 shows enhanced expression of C43 in MCF-7 cells by inhibition of methylation. MCF-7 cells were left untreated or treated with an inhibitor of DNA methyltransferase, a-aza-deoxycytined (5-aza-dC). Expression of C43 was monitored by a real time RT PCR approach and cell migration ability was determined by a transwell chamber migration assay. Treated cells with 5-aza-dC increased endogenous C43 expression, suggesting that DNA methylation could be blocking the C43 expression in MCF-7 cells (A). Increased expression of C43 by inhibition of methylation in MCF-7 cells resulted in enhanced cell migration (B). No effect on C43 expression and cell migration was seen in MDA-MB-231 cells.

DETAILED DESCRIPTION OF THE INVENTION

The present invention relates to the diagnosis and treatment of cancer, and in particular breast cancer. Specifically, in some embodiments the invention relates to methods of diagnosing of cancer, and in particular breast cancer, using an antibody specific for a gene product that localizes selectively to the endoplasmic reticulum of cancer cell(s). In some embodiments, the invention relates to methods of treating of cancer, and in particular breast cancer, by administering a composition comprising a molecule characterized by an ability to inhibit an mRNA molecule encoded by the C43 gene. The invention additionally relates to methods for detecting cancer cells by detecting reduced methylation of the C43 promoter, and methods for reducing cancer metastasis by using demethylation inhibitors that result in increased methylation of the C43 promoter. The invention additionally relates to an in vitro 3-dimensional assay for detecting migrating and/or invading cells, identifying test agents and/or nucleotide sequences that alter cell migration and/or invasion. The invention is further described under A) C43 expression, B) C43 promoter methylation, and C) In vitro 3-dimensional invasion assay, and D) Kits.

A. C43 Expression

1. Methods for Detecting a Cancer Cell

The invention provides a method for detecting a cancer cell, comprising detecting increased expression of C43 nucleotide sequence SEQ ID NO:1 compared to a normal cell. The invention's methods are useful for detecting cancer cells, metastatic cancer cells, determining prognosis for cancer and/or metastasis relapse (e.g., FIG. 12). In one embodiment, the invention's methods are particularly useful for detecting metastatic cancer cells.

As used herein, "detecting increased expression" refers to detecting increased mRNA levels and/or increased polypeptide levels that are encoded by a DNA sequence, compared to a control sample. Data herein (e.g., Example VI) shows that C43 gene expression was from 5 to 6 higher in breast cancer cells compared to normal breast cells.

Thus in one embodiment, detecting increased expression of C43 involves detecting the C43 protein, such as by contacting the cell with antibody that specifically binds to C43 polypeptide sequence SEQ ID NO:4 (exemplified in FIG. 10).

"Specific for C43 polypeptide sequence" and "specifically binds to a C43 polypeptide sequence described as SEQ ID NO:4" shown in FIG. 10 includes antibody that is specific for at least a portion of C43 polypeptide described as SEQ ID NO:4. Examples of portions of C43 polypeptide include "antigenic" portions, i.e., portions that are capable of inducing a specific humoral immune response (including eliciting a soluble antibody response) and/or cell-mediated immune response (including eliciting a CTL response). Methods for determining antigenic portions of a polypeptide are known in the art.

Figure 20:
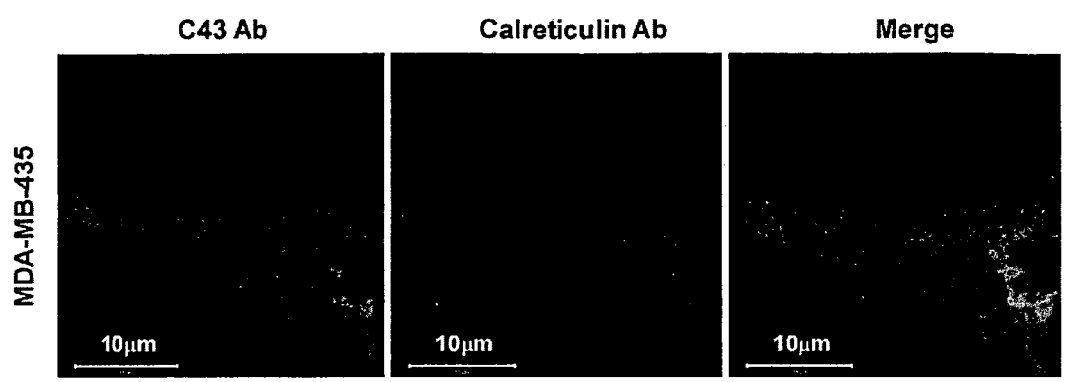
FIG. 20 shows detection of endogenous C43 using a polyclonal antibody. C43 is localized in the endoplasmic reticulum. Representative images of MDA-MB-435 cells stained with anti-C43 (left panel) and anti-calreticulin, a protein that is localized primarily in the ER. The anti-C43, and anti-calreticulin overlayed images are shown (right panel), where areas of C43 and calreticulin colocalization are shown in yellow. Images were taken on Zeiss LSM 510 META NLO Two-Photon Laser Scanning Confocal Microscope System with a 40× Plan Neofluar objective and DAPI/FITC/Texas Red filter set. Colocalization was determined to be 89% on the Carl Zeiss LSM Image Examiner software.

Antibodies specific for C43 polypeptide may be produced using known methods and commercial providers (e.g., PrimmBiotech, MA, U.S.A.). In one embodiment, plasmid DNA of C43 was sent to PrimmBiotech for antibody generation. Based on computational analysis of C43 amino acid sequence, the C-terminal region from aa1108-aa1340 was chosen for antibody production. The recombinant DNA was generated to encode nt 3582-nt 4281 of C43 gene and recombinant protein was expressed in E. coli. The purified protein was used to immunize rabbits following a standard protocol. The anti-serum was then collected and analyzed by ELISA. Antibodies that are specific for C43 polypeptide sequence are exemplified by those described in Examples V and IV. While not limiting the site of detection in a cell, in one embodiment, C43 protein can be detected by detecting the C43-antibody in the endoplasmic reticulum as exemplified in FIG. 20.

In another embodiment, detecting increased expression of C43 involves detecting the C43 mRNA that is encoded by C43 nucleotide sequence described as SEQ ID NO:1. "Detecting C43 nucleotide sequence" includes detecting at least a portion of C43 nucleotide sequence described as SEQ ID NO:1, such as portions used in PCR, Southern blots, etc.

It is not intended that the source of the cells that are tested using any of the invention's methods be limited to a particular source. Thus, in one embodiment, the cell is comprised in a sample, such as from tissue of a mammalian subject.

2. Methods for Reducing Cancer Metastasis in a Subject

Figure 12A:
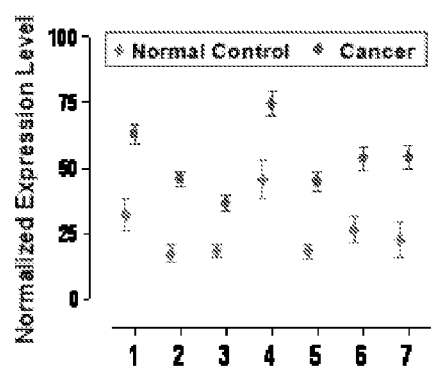
FIG. 12 shows data mining DNA microarray: A). By analysis of Oncomine and GEO databases, C43 expression patterns in more than 40 microarray data sets show significant alteration (P<0.01). Representative data are presented. A) High C43 expression in various human cancers. 1: Breast cancer, n=39, normal tissue, n=8; 2: ovarian cancer, n=99, normal, n=4; 3: lung cancer, n=31, normal, n=26; 4: pancreatic cancer, n=14, normal, n=11; 5: head & neck cancer, n=41, normal, n=13; 6: melanoma, n=26, normal, n=10; and 7: mesothelioma, n=40, normal, n=5. B) expression of C43 in ER-negative and positive breast cancer tissues: ER negative, n=77; positive, n=209. C) High expression of C43 in breast cancer recurrence. disease free, n=45; relapse, n=27.
Figure 12B:
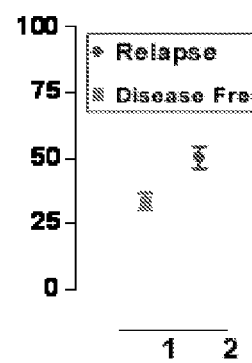
Figure 12C:
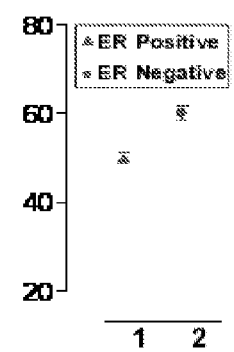
Figure 13:
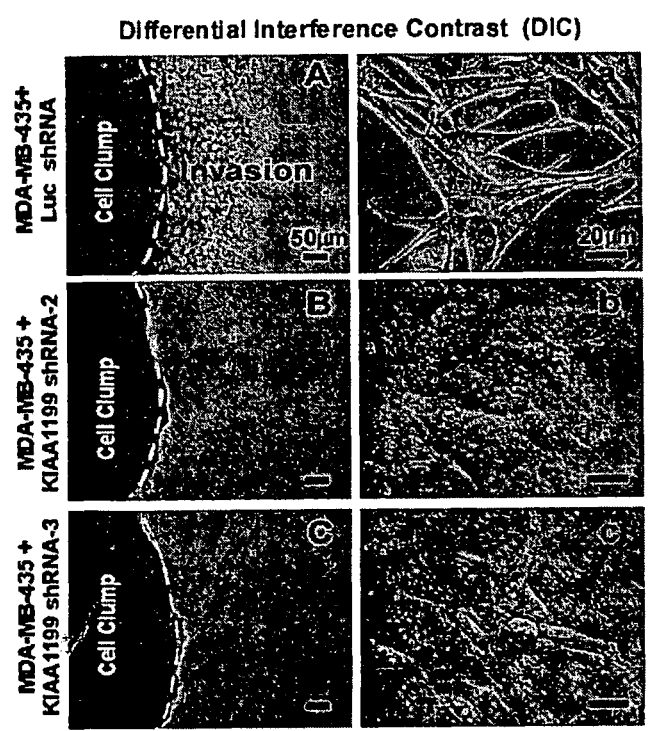
FIG. 13 shows phenotypic changes of MDA-MB-435 cells by downregulation of C43. Left panel: Loss of invasive ability of MDA-MB-435 cells by downregulation of C43. MDA-MB-435 cells expressing Luciferase shRNA control, C43 shRNA-2 and -3 were examined by the 3D invasion assay after 8 days. Knockdown of C43 in the cells results in loss of cell invasive ability, but does not alter cell proliferation. Right panel: Change of cell morphology of MDA-MB-435 cells by downregulation of C43. MDA-MB-435 cells expressing Luciferase shRNA shRNA, C43 shRNA-2 and -3 cultured on plastic dishes were observed under inverted microscopy with differential interference contrast (DIC).
Figure 14:
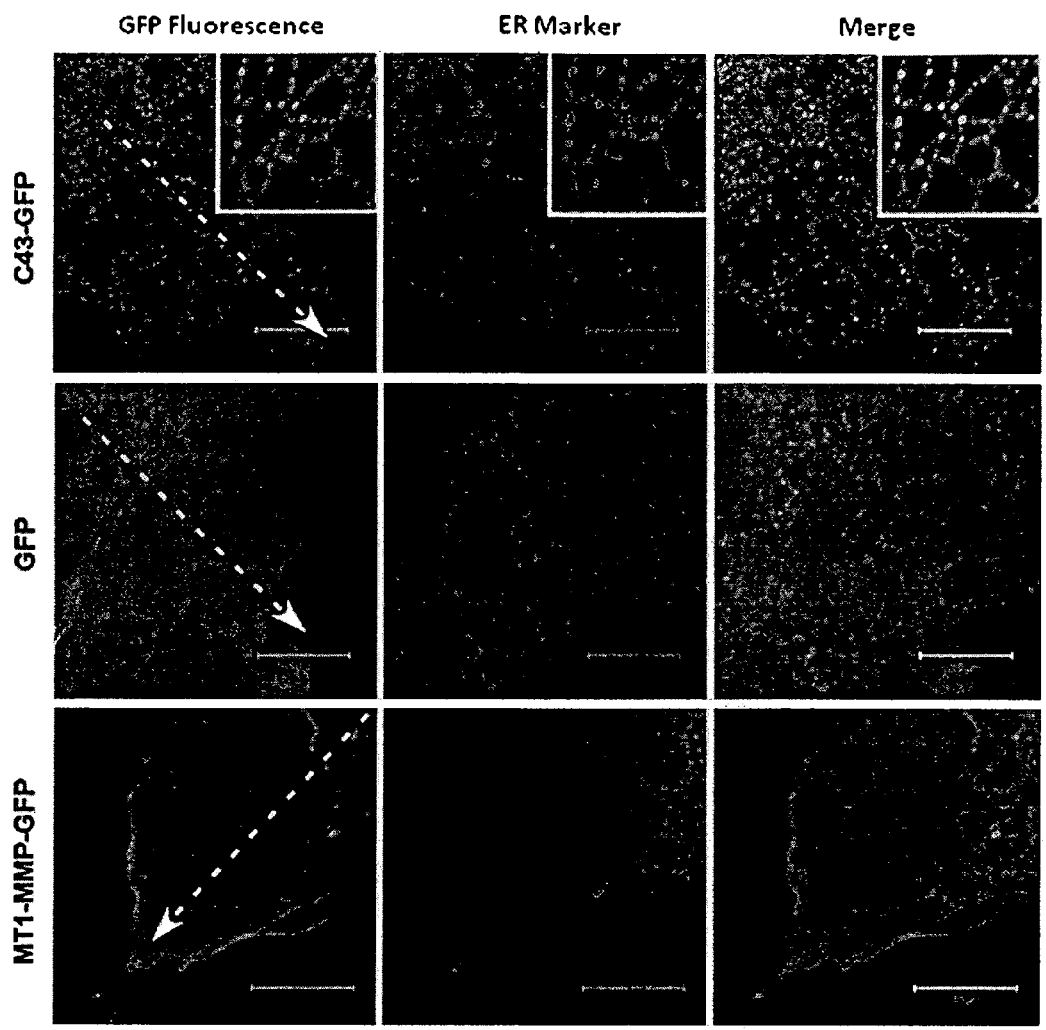
FIG. 14 shows endoplasmic reticulum (ER) localization of C43. COS-1 cells expressing GFP, MT1-GFP chimeric cDNA or C43-GFP chimeric cDNA were immunostained with ER marker, anti-calreticulin antibody. Based on GFP fluorescence, C43 displayed within a meshwork pattern in the cytoplasm and co-localized (over 90%) with ER marker, calreticulin. This meshwork pattern of C43 was not seen in control cells expressing GFP or MT1-GFP chimera. Inserts are enlarged pictures and arrows point to cell surface from the nuclear.
Figure 15A:
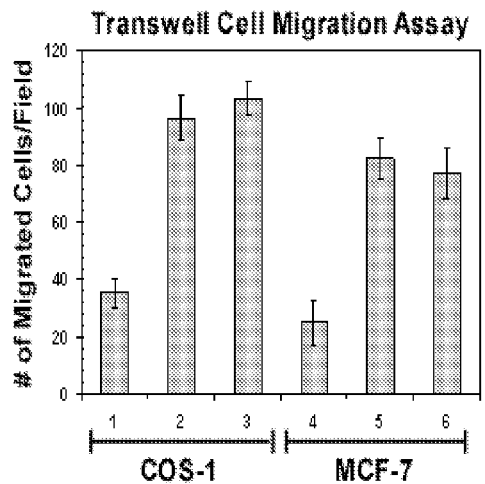
FIG. 15 shows that C43 plays a critical role in cell migration. A) Overexpresison of C43 enhanced cell migration. COS-1 cells and MCF-7 cells transfected with vector control (1 & 4), C43 (2 & 5) or MT1-MMP (3 & 6, positive control) cDNAs were evaluated by a Transwell Chamber migration assay after 6 hours. The cells were fixed and migratory cells were counted under microscopy with 20× objective. Ten fields were examined for each transfected cells. Each bar represents the mean±SE. B) Enhanced cell migration in MCF-7 cells expressing C43-GFP chimera. Minimally invasive human breast cancer MCF-7 cells stably transfected with GFP control and C43-GFP chimeric cDNA were mixed with type I collagen and dotted onto a 96-well plate. After solidification of the cell-collagen mixture, the dots were covered with culture medium followed by an 18 hour incubation. Cell migration was determined under microscopy. MCF-7 cells expressing C43-GFP had significant migration away from the initial dot, GFP control cells did not display any enhanced cell migration. Right panel shows nuclear staining with DAPI. C-D) Interference of endogenous C43 expression in aggressive breast cancer MDA-MB-435 cells failed to enhance cell migration. To determine the role of endogenous C43 in cell migration, a shRNA approach was employed. shRNAs against C43 were delivered into MDA-MB-435 cells by a retroviral infection approach. Employing a real time RT PCR approach, shRNA 2 and 3 were found to significantly decrease endogenous C43 expression in the cells. To determine the cell migratory ability, a phagokinetic assay was used. Decrease of C43 gene expression by an shRNA approach markedly inhibited MDA-MB-435 cell migration as compared to controls. This observation was further confirmed by a transwell chamber migration assay, confirming the role of C43 in cancer cell migration.
Figure 15B:
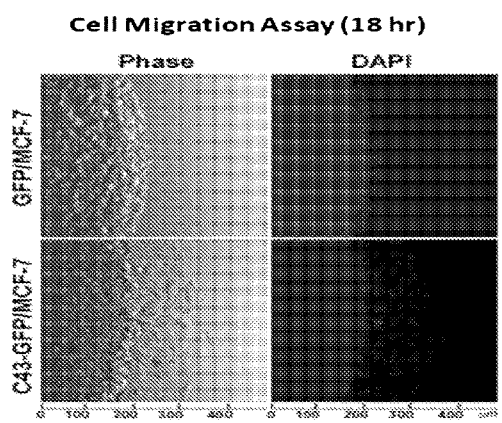
Figure 15C:
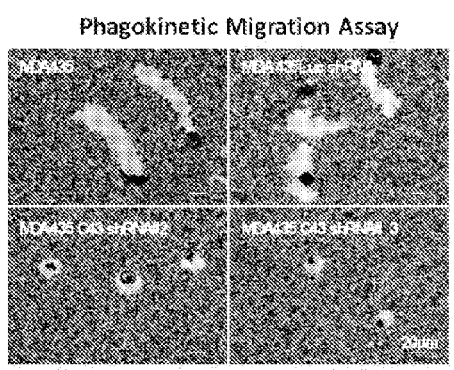
Figure 15D:
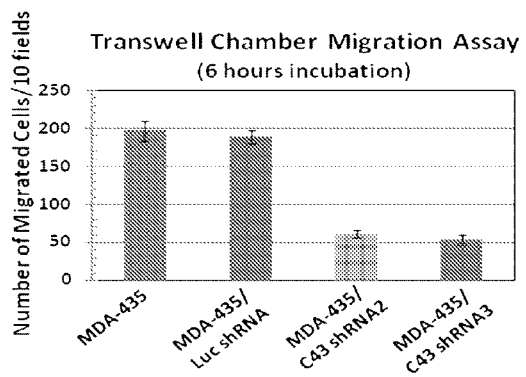

Data herein demonstrate upregulation of C43 gene in human breast cancer, ovarian cancer, lung cancer, pancreatic cancer, head and neck cancer, melanoma, and mesothelioma (FIG. 12). Thus, the invention also provides a method for reducing cancer metastasis (and/or reducing one or more symptoms of cancer) in a subject, comprising a) providing i) a mammalian subject in need of reducing cancer metastasis (and/or in need of reducing one or more symptoms of cancer), and ii) a composition comprising an agent that reduces the biological activity of C43 protein (SEQ ID NO:4) of FIG. 10, b) administering a therapeutic amount of the composition that reduces cancer metastasis (and/or reduces one or more symptoms of cancer) to the subject.

"Biological activity of C43 protein" comprises increasing cell migration and/or cell invasion activity in a cell that expresses the C43 protein compared to in the absence of C43 protein expression. "Migration," "migrating," "motility" and grammatical equivalents when used in reference to a cell, interchangeably refer to the spatial movement of a cell on a 2-dimensional substrate (such as a solid substrate, or on a feeder layer of cells on a solid substrate), and/or within a 3-dimensional matrix (such as within the 3-dimensional collagen matrix described herein). "Invasion," "invasive" and grammatical equivalents when used in reference to a cell, interchangeably refer to the spatial movement of a cell within a 3-dimensional matrix (such as within the 3-dimensional collagen matrix described herein). Therefore, an invading cell is necessarily also a migrating cell. In contrast, a migrating cell may be a non-invading or an invading cell.

I. PCR Subtraction Hybridization

PCR subtraction hybridization entails digesting a DNA molecule of interest and a reference DNA molecule (tester and driver, respectively) with a restriction endonuclease such as AluI to generate DNA fragment populations with median sizes of about 0.5 kb. Two different PCR adaptors that can join only to 5' ends of target DNAs (because their own 5' ends lack phosphate groups) are ligated to different aliquots of tester DNA. These ligated DNAs are denatured, mixed with an excess of driver DNA (that has no adaptors), and allowed to anneal. The two DNA pools are then mixed together, and more denatured driver DNA is added to further bind tester sequences that are alto present in the driver genome. Remaining complementary single strands of tester DNA are allowed to anneal, and the adaptor sequences are copied onto their 3' ends. PCR is then used to obtain exponential amplification of tester DNAs with different adaptors at each end. In contrast, amplification of DNAs with the same adaptor at each end is suppressed because self-annealing of inverted repeat adaptors inhibits binding of PCR primers. Tester DNAs with an adaptor at only one end undergo linear, but not exponential, amplification. This method offers several substantial advantages over earlier subtraction methods: (i) less DNA is needed; (ii) multiple rounds of hybridization and physical removal of tester-driver DNA complexes are not needed; and (iii) there is no need for complicated adaptor removal and re-addition, with additional rounds of PCR amplification, as in the representational difference analysis method.

II. RNAs that Silence Gene Expression (siRNA, RNAi, and shRNA).

RNA interference (RNAi) is a form of double-stranded (ds) RNA sequence-specific gene silencing. The first step in the RNAi pathway involves the generation of a sequence-specific RNA effector molecule by cleavage of a long dsRNA species into short interfering dsRNA (siRNA), typically from 21-25 nucleotides (nt) in length. These siRNA molecules may then facilitate the degradation of RNA molecules that are homologous to them. In some embodiments, siRNAs are 21-23 nt dsRNA duplexes with symmetric 2-3 nt 3' overhangs and 5'-phosphate and 3'-hydroxyl groups; this structure is characteristic of an RNaseIII-like enzymatic cleavage pattern. Studies have demonstrated that this process is restricted to the cytoplasm. In the first step, Dicer (a family of RNase III enzymes) cleaves long dsRNA to produce siRNA. These siRNAs are incorporated into a multiprotein RNA-inducing silencing complex (RISC). There is a strict requirement for the siRNA to be 5' phosphorylated to enter the RISC. siRNAs that lack 5' phosphate are rapidly phosphorylated by an endogenous kinase. The duplex siRNA is unwound, leaving the antisense strand to guide the RISC to its homologous target mRNA for endonucleolytic cleavage. The target mRNA is cleaved as a single site in the center of the duplex region between the guide siRNA and the target mRNA, 10 nt from the 5' end of the siRNA.

RNAi mediated by the introduction of long dsRNA has been used as a method to investigate gene function in various organisms including plants, planaria, Hydras, Trypanosomes, *Drosophila*, mosquitoes, and mouse oocytes. Long dsRNA enables the effective silencing of gene expression by presenting various siRNA sequences to the target mRNA. The applicability of this approach is limited in mammals because the introduction of dsRNA longer than 30 nucleotides induces an interferon response.

To promote efficient gene silencing using an siRNA to a single site in the target mRNA, the siRNA sequence must be chosen with care. The base composition of the siRNA sequence is not the only determinant of how effectively it will silence a gene; other factors are likely to play a role, such as the secondary structure of the mRNA target and the presence of RNA-binding proteins. In some embodiments, sequence motifs consistent with effective siRNA-directed silencing include $AAN_{19}TT$, $NAN_{19}NN$, $NARN_{17}YNN$ and $NANN_{17}YNN$ (where N is any nucleotide, R is a purine and Y is a pyrimidine). When choosing siRNAs, regions of complementary DNA are selected that have non-repetitive sequences. Preferably, intronic sequences are avoided, as mammalian RNA interference is a cytoplasmic process where, in general, no intronic RNA exists. In some embodiments, siRNAs with approximately 50% GC (3-70%) content are used. In other embodiments, sequences that are known sites for mRNA-binding proteins in the 5' untranslated region (UTR), 3' UTR, start codon, or exon-exon boundaries are avoided. In further embodiments, sequences that are 50-100 nt downstream of the start codon are preferably targeted. In yet other embodiments, effective siRNA-directed silencing is achieved by targeting the 3' portion of the gene. To ensure the chosen siRNA sequence targets a single gene, a BLAST search of the selected sequence is performed against sequence databases such as EST or Unigene libraries using the National Center for Biotechnology Information (NCBI) website (http://www.ncbi.nlm.nih.gov/), herein incorporated by reference. Potential off-target effects of the siRNA might be minimized by choosing an siRNA with maximum sequence divergence from the list of genes with partial sequence identity to the intended mRNA target.

Although originally identified for its ability to cleave long dsRNA, in vitro and in vivo data have shown that Dicer can process hairpin RNA structures. The main difference between the expression of the siRNAs as two different strands (sense and antisense) and the expression of the siRNAs from hairpin RNA is the dependency of the shRNA on Dicer processing. RNA molecules produced by Dicer cleavage may enter the RISC-mediated step of the cleavage pathway more efficiently than RNA molecules introduced directly as siRNAs.

Two types of retrovirus vectors have been used as gene delivery systems: i) oncoretrovirus vectors based on the Moloney murine leukemia virus (MoMuLV) or the murine stem cell virus (MSCV), and ii) lentivirus vectors derived from human immunodeficiency virus-1 (HIV-1). Lentiviruses are a class of retrovirus with two distinct characteristics that make them more effective gene delivery vectors than oncoretrovirus vectors. Unlike oncoretrovirus vectors, HIV-1 based lentivirus vectors can infect both actively dividing and non-dividing post-mitotic cells. In addition, oncoretroviruses undergo proviral silencing during development, which leads to decreased or abrogated gene expression. Lentivirus-based vectors are resistant to this silencing and therefore can be used to generate transgenic animals.

Chemically synthesizing siRNA sequences that effectively silence gene expression are also effective when generated from short hairpin RNA (shRNA). The length of the stem and the size and composition of the loop have been implicated in the efficiency of silencing. In some embodiments, stem lengths of 19-29 nucleotides silence genes effectively, indicating that stem length is not the main parameter governing efficient gene silencing. Longer stems provide more Dicer cleavage sites without having to cleave into the loop. In some embodiments, shorter duplex RNAs are more sensitive to the surrounding RNA sequence than longer duplex RNAs. It is not necessary that there be complete silencing, for the present application it is sufficient for there to be some silencing.

In one embodiment, the agent that reduces the biological activity of C43 protein comprises shRNA that specifically binds to mRNA encoded by the C43 nucleotide sequence SEQ ID NO:1 (FIG. 2), preferably that reduces expression of C43 polypeptide encoded by the C43 nucleotide sequence SEQ ID NO:1.

Methods for designing an shRNA sequence are known in the art including web-based software BLOCK-iT™ RNAi Designer available online at rnaidesigner.Invitrogen.com/rnaiexpress/. The BLOCK-iT™ RNAi Designer software may be used to design siRNA, Stealth RNAi™ siRNA, miR RNAi inserts and shRNA inserts for any target sequence. In one embodiment, C43 targeting sequences were further prioritized based on guidelines described by Ui-Tei et al. (Ui-Tei et al. Nucleic Acids Res., 32, 936-948). These criteria were: i. A/U at the 5' end of the antisense strand; ii. G/C at the 5' end of the sense strand; iii. AU-richness in the 5' terminal one-third of the antisense strand; and iv. the absence of any GC stretch over 9 bp in length. Exemplary designed C43 shRNA sequences are described in Table 1.

TABLE 1

Exemplary shRNA sequences that specifically bind to mRNA encoded by the C43 nucleotide sequence SEQ ID NO: 1 (FIG. 2) and that reduce expression of the encoded C43 polypeptide SEQ ID NO: 4 (FIG. 10).

| Reference No. | nt | Sequence | SEQ ID NO: |
|---|---|---|---|
| 1 | — | CCTCTCCATCC ATCATACATT | SEQ ID NO: 2 (FIG. 3) |
| 2 | nt 1104 | GTGGAAGACCA TATTGAATAT | SEQ ID NO: 5 |
| 3 | nt 1997 | GCCTCTCCATC CATCATACATT | SEQ ID NO: 6 |
| 4 | nt 3456 | GCCATCTGGCT CATCAACTT | SEQ ID NO: 7 |
| 5 | nt 2743 | GCTCCAAGCAA GAGATAAAGA | SEQ ID NO: 8 |
| 6 | nt 2797 | GGACGGAAATG ATGGACAATA | SEQ ID NO: 9 |
| 7 | nt 3115 | GGGATAAGACA TCTGTGTTCC | SEQ ID NO: 10 |
| 8 | nt 3206 | GCACCCAGACT GCATCAATGT | SEQ ID NO: 11 |

TABLE 1-continued

Exemplary shRNA sequences that specifically bind to mRNA encoded by the C43 nucleotide sequence SEQ ID NO: 1 (FIG. 2) and that reduce expression of the encoded C43 polypeptide SEQ ID NO: 4 (FIG. 10).

| Reference No. | nt | Sequence | SEQ ID NO: |
|---|---|---|---|
| 9 | nt 3370 | GCACCCATTAC CAGCAATACC | SEQ ID NO: 12 |
| 10 | nt 3595 | GGACCTTGCAG ATGGACAAAG | SEQ ID NO: 13 |
| 11 | nt 5377 | GCCCACTCATG ATGGAGAAGT | SEQ ID NO: 14 |
| 12 | nt 5412 | GCAATGGGCTT TGCTGCTTAT | SEQ ID NO: 15 |
| 13 | nt 5826 | GGAAATGACTA GAGTAGAATG | SEQ ID NO: 16 |
| 14 | nt 6397 | GGTCTTTCCCA CCAAACATCT | SEQ ID NO: 17 |

The terms "test compound," "compound," "agent," "test agent," "molecule," and "test molecule," as used herein, (such as agents that reduce the biological activity of C43 protein), refer to any type of molecule (for example, a peptide, polypeptide, vaccine, antibody, nucleic acid, nucleic acid sequence, carbohydrate, saccharide, polysaccharide, lipid, organic molecule, inorganic molecule, etc.) obtained from any source (for example, plant, animal, and environmental source, etc.), or prepared by any method (for example, purification of naturally occurring molecules, chemical synthesis, and genetic engineering methods, etc.).

A test compound may have a known, or unknown, structure and/or composition. Examples of test compounds that have unknown compositions include cell extracts, tissue extracts, growth medium in which prokaryotic, eukaryotic, and archaebacterial cells have been cultured, fermentation broths, protein expression libraries, DNA libraries, and the like.

The "test compound," can be synthetic, naturally occurring, or a combination thereof. A synthetic test compound can be a member of a library of test compounds (e.g., a combinatorial chemical library). Methods for making these libraries of compounds are known in the art, such as methods for preparing oligonucleotide libraries (Gold et al., U.S. Pat. No. 5,270, 163, incorporated by reference); peptide libraries (Koivunen et al. J. Cell Biol., 124: 373-380 (1994)); peptidomimetic libraries (Blondelle et al., Trends Anal. Chem. 14:83-92 (1995)) oligosaccharide libraries (York et al., Carb. Res. 285: 99-128 (1996); Liang et al., Science 274:1520-1522 (1996); and Ding et al., Adv. Expt. Med. Biol. 376:261-269 (1995)); lipoprotein libraries (de Kruif et al., FEBS Lett., 399:232-236 (1996)); glycoprotein or glycolipid libraries (Karaoglu et al., J. Cell Biol. 130:567-577 (1995)); or chemical libraries containing, for example, drugs or other pharmaceutical agents (Gordon et al., J. Med. Chem. 37:1385-1401 (1994); Ecker and Crook, Bio/Technology 13:351-360 (1995), U.S. Pat. No. 5,760,029, incorporated by reference). Additional examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994);

Carell et al., Angew. Chem. Int. Ed. Engl. 33:2061 (1994); and Gallop et al., J. Med. Chem. 37:1233 (1994).

A synthetic test compound may be a member of a biological library or peptoid library (i.e., library of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)). The biological library and peptoid library are particularly suited for use with peptide libraries.

In addition, a synthetic test compound may be a member of a spatially addressable parallel solid phase library or solution phase library, of a synthetic library that uses methods such as a deconvolution method, a 'one-bead one-compound' library method, affinity chromatography selection. These methods are particularly suited to peptide libraries, non-peptide oligomer libraries, and small molecule libraries of compounds (Lam (1997) Anticancer Drug Des. 12:145).

Libraries of diverse molecules also can be obtained from commercial sources, e.g., Brandon Associates (Merrimack, N.H.) and Aldrich Chemical Co (Milwaukee, Wis.).

A naturally occurring test compound can be a component of a cellular extract or bodily fluid (e.g., urine, blood, tears, sweat, or saliva). A naturally occurring test compound may be obtained by extraction and/or purification of commercially available libraries of bacterial, fungal, plant, and animal extracts.

A test compound includes both known therapeutic compounds, and potentially therapeutic compounds. An agent can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

Retrovirus delivery and hydrodynamic infusion of siRNAs into primary tissues allows analysis of gene function in a physiological context without the production of knockout mice through homologous recombination. siRNA-based gene silencing offers the ability for gene-function determination as well as therapeutic gene silencing.

III. Methods of Administration

Methods of administering the therapeutic or prophylactic agents include, but are not limited to, parenteral administration (e.g., intradermal, intramuscular, intravenous and subcutaneous, including injection directly into the tumor) and mucosal administration (e.g., intranasal, rectal, vaginal, sublingual, buccal or oral routes including inhalation and insufflation). Therapeutic or prophylactic agents can also be administered by infusion or bolus injection. Administration can be local or systemic. In a preferred embodiment, local or systemic parenteral administration is used.

a) Parenteral

Therapeutic or prophylactic agents can be formulated for parenteral administration by injection (e.g., bolus injection) or continuous infusion. Formulations for injection can be presented in unit dosage form, e.g., in ampules or in multi-dose containers, with an added preservative. The pharmaceutical compositions can include such forms as suspensions, solutions or emulsions in oily or aqueous vehicles, and can contain formulatory agents such as suspending, stabilizing and/or dispersing agents. Such long acting formulations can be administered by implantation (for example subcutaneously or intramuscularly) or by intramuscular injection.

In a preferred embodiment, the therapeutic or prophylactic agent is formulated in accordance with routine procedures as pharmaceutical compositions adapted for intravenous administration to human beings. Typically, the active compounds for intravenous administration are solutions in sterile isotonic aqueous buffer. Where necessary, the compositions can also include a solubilizing agent. Generally, the ingredients are supplied either separately or mixed together in unit dosage form, for example, as a dry lyophilized powder or water free concentrate in a hermetically sealed container such as an ampule or sachette indicating the quantity of active agent. Where the active compound is to be administered by infusion, it can be dispensed, for example, with an infusion bottle containing sterile pharmaceutical grade water or saline. Where the therapeutic or prophylactic agent is administered by injection, an ampule of sterile water for injection or saline can be provided so that the ingredients can be mixed prior to administration.

b) Oral/Oropharyngeal

Compositions for oral delivery can be in the form of tablets, lozenges, aqueous or oily suspensions, granules, powders, emulsions, capsules, syrups, or elixirs, for example. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for oral administration. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade. Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosal (such as buccal, vaginal, rectal, sublingual) administration. In one embodiment, local or systemic parenteral administration is used.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of gelatin (for example) for use in an inhaler or insufflator can be formulated containing a mixture of the compound and a suitable powder base such as lactose or starch.

c) Dosages

The amount of the active compound that is effective in the treatment or prevention of breast cancer can be determined by standard research techniques. For example, the dosage of the therapeutic or prophylactic agent which will be effective in the treatment or prevention of breast cancer can be determined by administering the therapeutic or prophylactic agent to an animal in a model such as, e.g., the animal models known to those skilled in the art. In addition, in vitro assays can optionally be employed to help identify optimal dosage ranges. Selection of a particular effective dose can be determined (e.g., via clinical trials) by a skilled artisan based upon the consideration of several factors, which will be known to one skilled in the art. Such factors include the disease to be treated or prevented, the symptoms involved, the subject's body mass, the subject's immune status and other factors known by the skilled artisan. The dose of the active compound to be administered to a subject, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

Antibody treatment of human beings with cancer is well-known in the art, for example in U.S. Pat. No. 5,736,137 (herein incorporated by reference). Anti-sense treatment of human beings with cancer is also well-known in the art, for example U.S. Pat. No. 7,273,855 (herein incorporated by reference).

B. C43 Promoter Methylation

1. Methods for Detecting a Cancer Cell

Data herein demonstrate hypomethylation of CpG island spanning the 5' end of the regulatory region of C43 gene in aggressive cancers (Example VII). Thus, in one embodiment, the invention provides a method for detecting a cancer cell, comprising detecting decreased methylation of the promoter region of C43 nucleotide sequence (SEQ ID NO:1) compared to a normal cell. The invention's methods are particularly useful for detecting metastatic cancer cells.

"Detecting decreased methylation of C43 promoter region" is exemplified by detecting decreased levels of methylation of CpG-rich island #157 of the of the 5' UTR spanning the transcription start site (+1) of C43 gene from the 81,071,268 to 81,073,220 within chromosome 15.

2. Methods for Reducing Cancer Metastasis in a Subject

The invention provides a method for reducing cancer metastasis in a subject (and/or reducing one or more symptoms of cancer), comprising a) providing i) a mammalian subject in need of reducing cancer metastasis, and ii) a composition comprising an agent that reduces demethylation of the promoter region of C43 nucleotide sequence (SEQ ID NO:1), b) administering a therapeutic amount of the composition that reduces cancer metastasis (and/or reduces one or more symptoms of cancer) to the subject.

Agents for inhibiting demethylation are known in the art, and are exemplified by S-adenosyl-L-methionine (SAM), 5'-methylthioadenosine (MTA), and methylated DNA binding domain 2 (MBD2) antisense oligonucleotide (Szyf (2009) Annu. Rev. Pharmacol. Toxicol. 49:243-263).

C. In Vitro 3-Dimensional Invasion Assay

1. Methods for Detecting Migrating and/or Invading Cells in a Sample

The invention provides a method for detecting migrating and/or invading cells in a sample, comprising a) introducing the sample into a first 3-dimensional matrix (such as a gel that comprises type I collagen), b) contacting the first 3-dimensional matrix with a second 3-dimensional matrix (such as a gel that comprises type I collagen), and c) detecting the presence of cells in the second 3-dimensional matrix, thereby detecting migrating and/or invading cells in the sample. The invention's methods are useful for detecting the presence of metastatic cancer cells, screening compounds that alter cell migration and/or cell invasion and/or cancer metastasis, and for identifying genes that alter cell migration and/or cell invasion and/or cancer metastasis. The invention's methods are exemplified in FIGS. 5-9, 13, 15B, and 19. Examples V and VIII demonstrate the efficacy of the invention's 3-dimensional matrix assay in detecting compounds capable of inhibiting cell migration/invasion. Example IX demonstrates the efficacy of the invention's 3-dimensional matrix assay in identifying genes that alter cell migration and/or invasion and/or metastasis.

In one embodiment, the methods further comprises d) determining the number of cells in the second 3-dimensional matrix. The invention's methods are particularly useful for determining migration of any cell, including cancer cells (e.g., metastatic cancer cells), normal cells (e.g., fibroblasts, muscle cells, neural cells, etc.), and normal cells and/or cancer cells that are transfected with metastasis genes and/or with anti-metastasis genes.

In a particular embodiment, the invention provides a method for detecting migrating and/or invading cells in a cell sample, comprising a) providing i) a first well, ii) a cell sample, and ii) a solution (such as a solution comprising type I collagen), b) mixing the cell sample and the solution to produce a cell suspension, c) introducing the cell suspension into the first well, d) incubating the cell suspension under conditions such that the suspension forms a first 3-dimensional matrix having a first matrix surface that is not in contact with a surface of the first well surface, e) introducing the solution into the first well and in contact with the first matrix surface, f) incubating the solution under conditions such that the solution forms a second 3-dimensional matrix in contact with the first matrix surface, g) incubating the first well that comprises the first 3-dimensional matrix and the second 3-dimensional matrix under conditions for cell migration and/or invasion (e.g., adding cell culture medium in contact with the first and/or second matrices, and incubating in a humidified incubator at 37° C.), and h) detecting the presence of cells in the second 3-dimensional matrix, thereby detecting the presence of migrating and/or invading cells in the cell sample.

A "well" is a cavity, indentation, space, dent, crater, depression, hollow, recess or impression that is formed in the surface of a structure. The cross section of a well that is used for cell culture may be any shape, including, but not limited to, cross sections with curved lines (e.g., with a hemispheric and/or semicircular well bottom as in FIG. 19), straight line (e.g., flat well bottoms), converging straight lines (e.g., "V" shaped well bottom as in FIG. 9). Thus, cross sectional shape in plan view include, square, round, hexagonal, other geometric or non-geometric shapes, and combinations (intra-well and inter-well) thereof. Cross sectional shape in vertical view include shear vertical or chamfered walls, wells with flat or round bottoms, conical walls with flat or round bottoms, and curved vertical walls with flat or round bottoms, and combinations thereof.

While not intending to limit the configuration of the wells that contain the 3-dimensional matrices of the invention's assay, in one embodiment, the wells are comprised in a 96-well plate.

The invention's 3-dimensional invasion assay may be used to test agents for their effect on cell migration and/or invasion. This may be accomplished by introducing the test agent into a solution and contacting the solution with the second matrix that is in contact with the first matrix into which the cells were suspended. Alternatively, the test agent may be mixed with the cell suspension in the first matrix, and/or mixed with the second matrix that is in contact with the first matrix into which the cells were suspended.

Figure 9:
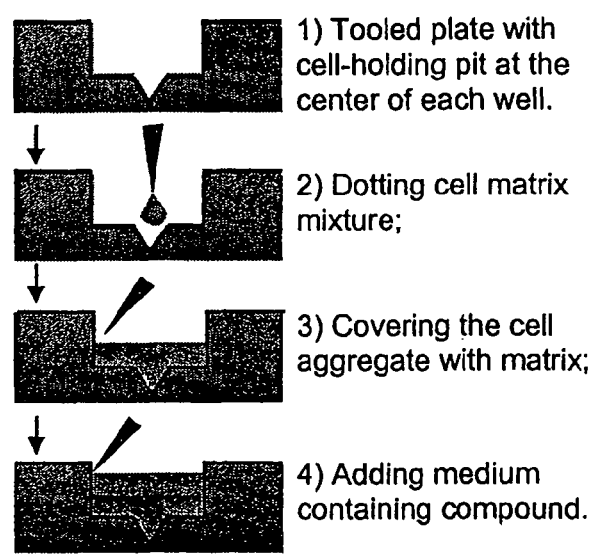
FIG. 9 depicts a flow chart of the steps involved in producing a single well of the 3D invasion assay.
Figure 11:
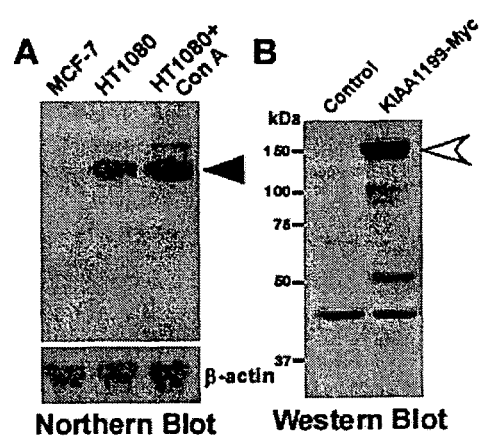
FIG. 11 shows Examination of KIAA1199 (C43 protein) expression in cells: A) Northern blot analysis of C43. Total RNAs of MCF-7 cells, HT1080 or HT1080 cells treated with Con A were probed with $p^{32}$-labeled C43 probe. A single 9.5 kb mRNA transcript corresponding to C43 was detected (arrowhead). Con A enhances C43 expression in HT1080 cells. B) Expression of C43 in transfected COS-1 cells: COS-1 cells transfected with vector or C43-Myc chimera were examined by Western blotting using anti-Myc antibody. C43 was detected as a 150 kDa protein band along with degradation products.
Figure 19:
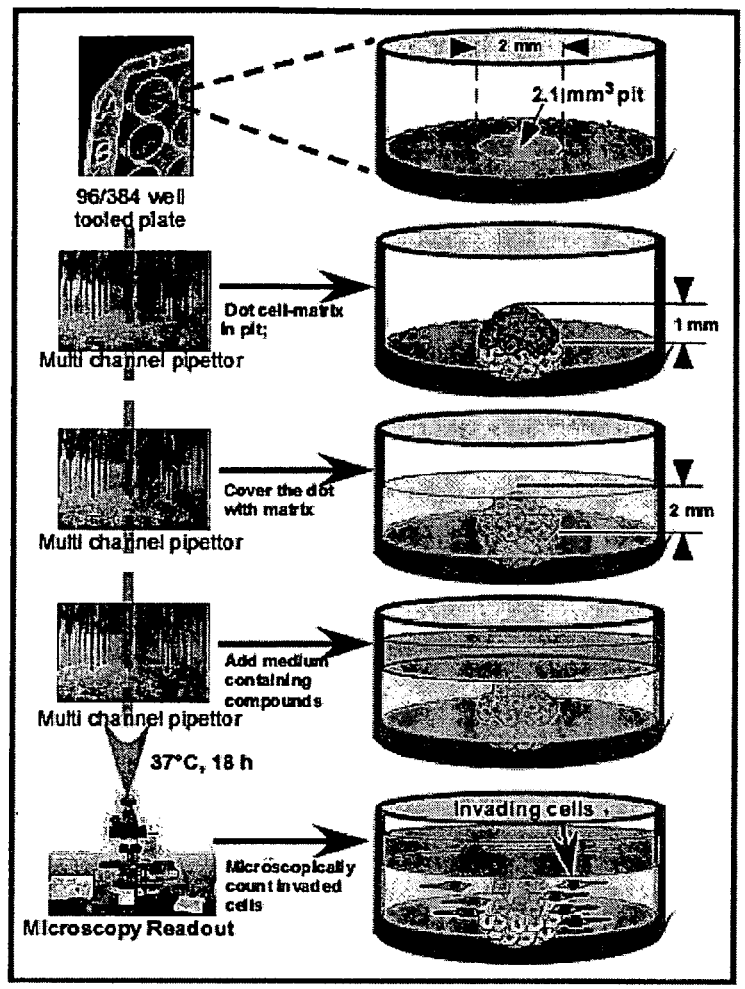
FIG. 19 shows a schematic diagram of the cell invasion assay (3-dimensional assay). A 96 well plate with 2.1 mm$^3$ hemisphere at the center of each well will be loaded with cell-matrix mixture. After gelation, the cell-matrix will be covered with a layer of matrix. Compounds will be then added and incubated for 18 hours. Inhibition of cell invasion will be microscopically examined. Diagram not to scale.

In one embodiment, the invention provides a multi-well platform comprising a plurality of wells, wherein at least one well has a surface that comprises a second well., as exemplified in FIGS. 9 and 19. "Plurality" means at least 2. In one embodiment, the well surface is at the bottom of the well. In a further embodiment, the second well comprises a 3-dimensional matrix containing cells. In a further embodiment, the plurality of wells is arranged in a two-dimensional linear array pattern.

"Matrix" refers to a substance (such as a gel) within which something else (e.g. a cell) is enclosed or embedded. "Gel" refers to a semi-solid colloid in a more solid form than a liquid, and a more liquid form than a solid. Examples of 3-dimensional matrices for cell culture are known in the art (Kim et al. (2004) Breast Cancer Research and Treatment 85:281-291; U.S. Patent Application Publication No. US 2006/0003311 to Fulde et al., and Debnath et al. 92005) Nature Reviews 5:675-688). Examples of 3-dimensional matrices include natural scaffolds and synthetic scaffolds. Natural scaffolds include collagen (such as pre-engineered collagen scaffolds), matrigel (e.g., from BD Biosciences), alginate, agarose, hyaluronic acid, and proteoglycan. Synthetic scaffolds include Skelite™, Poly (2-hydroxyethyl methacrylate) (polyHEMA), polyglycolic acid (PGA), polylactic acid (PLA), and mixtures of PGA and PLA.

The multi-well platforms of the present invention comprise a frame that contains a plurality of wells in which a 3-dimensional matrix, cells and/or solutions may optionally be introduced. The frame can be made of any material, such as polymers (e.g., polystyrene, cycloolefins, etc.), glass, quartz, etc. The frame can be of any thickness, such as from 0.5, 1, 2, 3, or 5 millimeters to 2, 3, 5, 10 or 20 millimeters.

The frame can be of any shape, and typically defines the footprint of the multi-well platform (e.g., square, rectangular, circular, oblong, triangular, kidney, or other geometric or non-geometric shape). Preferably, the footprint has a shape that is substantially similar to the footprint of existing multi-well platforms, such as the standard 96-well microtiter plate, whose footprint is approximately 85.5 mm in width by 127.75 mm in length or other sizes. Multi-well platforms of the present invention having this footprint can be compatible with robotics and instrumentation, such as multi-well platform translocators and readers.

Each well comprises side walls and a bottom surface. The bottom surface contains another well into which cells, and/or a three dimensional matrix that contains the cells, may be introduced Typically, wells are arranged in two-dimensional linear arrays on the multi-well platform. However, the wells can be provided in any type of array, such as geometric or non-geometric arrays. Commonly used numbers of wells include 24, 96, 384, 864, 1536, 3456, and 9600. The number of wells can be from 24, 50, 100, 200, 500, 700, 800 or 1000 wells, to 150, 250, 600, 800, 1,000, 2,000, 4,000 5,000, or 10,000 wells. Preferably, the number of wells is from 24 to 10,000, more preferably from 800 to 5,000, and most preferably from 900 to 4,000. The number of wells can be a multiple of 96 within these ranges, preferably an integer (such as 1, 2, 3, 4, 5, etc.) multiplied by 96 and/or the square of an integer multiplied by 96.

Well volumes may vary depending on well depth and cross sectional area. Exemplary well volumes can range from 0.5, 1, 5, 10, 25, 50, 75, 100 or 200 microliter to 5, 15, 40, 80, 100, 200, 500, or 1,000 microliters. In some embodiments, the well volume is from 500 nanoliters to 500 microliters, and in another embodiment, from 1 microliter to 200 microliter, and in yet a further embodiment, from 0.5 microliters to 10 microliters.

2. Methods for Identifying a Test Agent (e.g., Anti-Cancer Agent) as Reducing Cell Migration and/or Invasion The invention also provides a method for identifying a test agent as reducing cell migration, comprising a) providing i) a target cell that expresses C43 protein (SEQ ID NO:4), and ii) a test agent, b) contacting the test agent with the target cell to produce a contacted cell, and c) detecting migration by the contacted cell, wherein reduced migration of the contacted cell compared to migration of a control cell in the absence of the test agent identifies the test agent as reducing migration of a cell (including of a cancer cell). The invention's methods are useful for screening compounds that alter cell migration and/or cell invasion and/or cancer metastasis.

The invention's methods are exemplified by Example VIII, which demonstrates the efficacy of the invention's 3-dimensional invasion assay in detecting compounds capable of inhibiting cell migration/invasion.

In one embodiment, detecting migration of step c) comprises detecting migration in a 3-dimensional matrix (such as a gel comprising collagen type I). In another embodiment, the method further comprises detecting invasion by the contacted cell, wherein reduced invasion by the contacted cell compared to invasion by a control cell in the absence of the test agent identifies the test agent as reducing invasion by a cell (including of a cancer cell, such as a metastatic cancer cell). In a particular embodiment, detecting invasion comprises detecting invasion in a 3-dimensional matrix (such as a gel comprising collagen type I).

The present invention also relates to a method of identifying an anti-cancer agent comprising: providing; a cell that expresses C43; and a candidate agent suspected of being capable of inhibiting C43 expression; contacting said agent with said cell; and determining whether said agent inhibits an activity of said cell. In one embodiment, the agent is an antibody that binds the C43 protein. In another embodiment, the agent is an shRNA that inhibits C43 RNA. In yet another embodiment, the agent kills the cell. In a further embodiment, said agent inhibits the motility of the cell. In one embodiment, cell motility is determined using a collagen matrix. In some embodiments, the present invention contemplates a method of identifying an anti-cancer agent comprising: providing a cancer cell(s), and a type I collagen matrix; suspending the cancer cells in the type I collagen matrix; extracting a droplet containing said cancer cells and said matrix; introducing said droplet to a multi-well plate; solidifying said droplet via heating to form a gel; layering said gel with an additional droplet of collagen, and examining properties associate with said cancer cells. In one embodiment, the present invention contemplated a method of identifying an anti-cancer agent comprising: providing a cancer cell(s), and a type I collagen matrix; suspending the cancer cell(s) in the type I collagen matrix; mixing the cancer cells in the matrix with an agent suspected of having anti-cancer activity; and assessing the anti-cancer activity of the agent. In one embodiment, the cancer cells are labeled with a fluorescent dye. In another embodiment, the cancer cells are examined with a fluorimeter. In another embodiment, the cancer cells are examined via fluorescent emission.

The target cell that may be used in the invention's methods may be any type of cell, such as a cancer cell, such as a primary cancer cell (derived from a tumor without immortalization by subculture and selection), and a cancer cell line. Cancer cells are exemplified by a breast cancer cell (exemplified by MCF-7 cell (non-invasive), MDA-MB-231 cell, MDA-MB-435 cell, MDA-MB-436 cell, and Hs578 cell), prostate cancer cell (exemplified by LNCaP cell (non-invasive), DU145 cell, and PC3 cell), colon cancer cell (exemplified by SW62 cell, HCT116 cell, and HT29 cell), fibrosarcoma cell (exemplified by HT1080 cell), and lymphoma cell (exemplified by P493-6 cell).

The target cell that may be used in the invention's methods includes a transgenic cell, such as a transgenic normal cell and a transgenic cancer cell. "Transgenic" cell refers to a cell that contains a transgene, or whose genome has been altered by the introduction of a "transgene" i.e., any nucleic acid sequence which is introduced into the cell by experimental manipulations.

The term "transgene" as used herein refers to any nucleic acid sequence that is introduced into the cell by experimental manipulations. A transgene may be an "endogenous DNA sequence" or a "heterologous DNA sequence" (i.e., "foreign DNA"). The term "endogenous DNA sequence" refers to a nucleotide sequence that is naturally found in the cell into which it is introduced so long as it does not contain some modification (e.g., a point mutation, the presence of a selectable marker gene, etc.) relative to the naturally occurring sequence. The term "heterologous DNA sequence" refers to a nucleotide sequence that is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence that contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins that confer drug resistance), etc.

Normal cells (whether transgenic or wild type) that may be used in the invention's methods are exemplified by wherein the normal cell is selected from the group consisting of MCF-10A cell (breast epithelial cell), COS-1 cell (African green monkey cell), NIH3T3 cell (fibroblast cell), HUVEC (Human Umbilical Vein Endothelial Cell), HFF (human foreskin fibroblast) cell, and Smooth muscle cell (SMC).

The transgenic cells may contain a heterologous (and/or endogenous) oncogenes. The term "oncogene" refers to a gene that is capable of transforming a normal cell to a cancer cell. An oncogene may be a viral oncogene or a cellular oncogene. A "viral oncogene" may be an early gene of a DNA virus (e.g., polyomavirus, papillomavirus, T-cell leukemia virus), or a cellular proto-oncogene incorporated into the genome of a transducing retroviruses such that the cellular proto-oncogene (e.g., c-src) is activated into an oncogene (e.g., v-src). In contrast to a viral oncogene, a "cellular oncogene" is a mutated cellular gene formed in situ in the chromosome of a cell rather than introduced into the cell by a DNA virus or a transducing virus. Exemplary oncogenes include c-Sis gene, epidermal growth factor receptor (EGFR) gene, platelet-derived growth factor receptor (PDGFR) gene, vascular endothelial growth factor receptor (VEGFR) gene, Her2/neu gene, v-Src gene, c-Src gene, Syk-SAP-70 gene, BTK gene, Abl gene, Raf kinase gene, cyclin-dependent kinase gene, Ras gene, and myc gene.

In another embodiment, the transgenic cells may contain a heterologous (and/or endogenous) gene that alters (i.e., increases or decreases) one or more of cell migration, cell invasion, and cell metastasis. Such genes are exemplified by genes that increase cell migration and/or invasion, including, MT1-MMP gene, C43 gene (FIG. 1), and metastasis genes. Metastasis genes that increase cell migration and/or invasion are exemplified by breast cancer metastasis metadherin (MTDH) gene, Bromodomain 4 (Brd4) gene, and CEACAM6 (carcinoembryonic antigen-related cell adhesion molecule 6) gene; melanoma metastasis gene NEDD9, which is abnormally abundant in more than a third of melanomas; and colon cancer Metastasis-Associated in Colon Cancer 1 (MACC1) gene.

In another embodiment, the transgenic cells may contain a heterologous (and/or endogenous) gene that decreases cell migration and/or invasion, including anti-metastasis genes. Anti-metastasis genes are illustrated by colon cancer Caspase 8 gene. Loss or suppression of Caspase 8 gene is seen in about 70 percent of small cell lung cancer, about 10 percent of colon cancer and about 35 percent of medulloblastoma. While genetic mutation will sometimes delete both copies of the caspase 8 gene, typically the gene is simply silenced. Anti-metastasis genes are also illustrated by lung cancer Caspase 8 gene, medulloblastoma Caspase 8 gene, liver cancer metastasis NM23-M1 gene (more mice that lacked the NM23-M1 gene developed metastases than mice that expressed the gene), renal cell carcinoma Ca9 gene (decreased CA9 expression was noted in non-metastatic renal cell carcinoma tumors compared to metastatic tumors), and breast cancer Maspin gene and prostate cancer Maspin gene (Maspin has anti-metastatic activity in breast and prostate cancers).

3. Methods for Identifying Genes that Alter Cell Migration (Including Metastasis)

The invention also provides a method for identifying a nucleotide sequence of interest as altering cell migration, comprising a) providing a cell comprising a nucleotide sequence of interest, and b) introducing the transgenic cell into a first 3-dimensional matrix (such as a gel comprising collagen type I), c) contacting the first 3-dimensional matrix with a second 3-dimensional matrix (such as a gel comprising collagen type I), and d) detecting migration of the transgenic cells from the first 3-dimensional matrix to the second 3-dimensional matrix, wherein altered migration of the transgenic cells compared to migration of a control cell lacking the nucleotide sequence of interest identifies the nucleotide sequence of interest as altering cell migration. The invention's methods are useful for identifying naturally occurring genes, mutations, regulatory genetic sequences that alter cell migration and/or cell invasion and/or cancer metastasis. For example, data herein (Example IX) show that the invention's assay successfully identified the MT1-MMP gene and the C43 gene as increasing cell migration and/or cell invasion and/or cancer metastasis.

The term "nucleotide sequences of interest" includes, but is not limited to, coding sequences of structural genes (e.g., oncogenes, metastasis genes, anti-metastasis genes, etc.), and non-coding regulatory sequences which do not encode an mRNA or protein product, (e.g., promoter sequence, enhancer sequence, etc.). "Metastasis gene" refers to a DNA sequence whose presence and/or expression in a cell increases the level of the cell's migration and/or invasion and/or metastasis compared to a control cell lacking the DNA sequence. "Anti-metastasis gene" refers to a DNA sequence whose presence and/or expression in a cell reduces the level of the cell's migration and/or invasion and/or metastasis compared to a control cell lacking the DNA sequence.

In one embodiment, the cell used in the invention's methods is transgenic and the nucleotide sequence of interest is heterologous to the cell. In another embodiment, the cell is a wild-type cell (e.g., a cancer cell derived from a subject) containing the nucleotide sequence of interest.

D. Kits

The present invention also contemplates kits. In one embodiment, the kit comprises a) a first containing means (e.g. tubes, vials, etc) containing a cell or cell line that expresses the C43 gene; and b) a second containing means containing a candidate agent suspected of being capable of inhibiting C43 expression. In another embodiment, the kit comprises a) a first containing means (e.g. tubes, vials, etc) containing an in vivo C43 transcription and translation system; and b) a second containing means containing a candidate agent suspected of being capable of inhibiting C43 expression. In another embodiment, the kit comprises a) a first containing means (e.g. tubes, vials, etc) containing an in vitro C43 transcription and translation system; and b) a second containing means containing a candidate agent suspected of being capable of inhibiting C43 expression. Such kits may include antibodies, including but not limited to antibodies specific for the C43 gene product, and anti-sense nucleic acid molecules specific for C43 RNA, including but not limited to shRNA nucleic acid molecules. Importantly, the kit is not limited to the particular components of said C43 screening system; a variety of components are contemplated (e.g. ribosomes), as for example in U.S. Pat. No. 7,312,060, herein incorporated by reference.

EXPERIMENTAL

The following are examples that further illustrate embodiments contemplated by the present invention. It is not intended that these examples provide any limitations on the present invention.

In the experimental disclosure that follows, the following abbreviations apply: eq. or eqs. (equivalents); M (Molar); .mu.M (micromolar); N (Normal); mol (moles); mmol (millimoles); .mu.mol (micromoles); nmol (nanomoles); pmoles (picomoles); g (grams); mg (milligrams); .mu.g (micrograms); ng (nanogram); vol (volume); w/v (weight to volume); v/v (volume to volume); L (liters); ml (milliliters); .mu.l (microliters); cm (centimeters); mm (millimeters); .mu.m (micrometers); nm (nanometers); C (degrees Centigrade); rpm (revolutions per minute); Roche Molecular (Roche Molecular Biochemicals, Indianapolis, Ind.); DNA (deoxyribonucleic acid); kdal (kilodaltons).

Example I

PCR Subtraction Hybridization

Cell motility and invasiveness are determinants of cancer metastasis. To further illuminate aspects of cancer cell migration and invasion, a PCR subtraction hybridization approach was employed to identify differentially expressed genes involved in Concanavalin A (Con A)-stimulated human HT1080 fibrosarcoma cells. This approach led to the identification of a 150-kDa gene, hereinafter termed C43 (SEQ ID NO: 1), involved in cancer cell migration and invasion. The C43 gene is identical to a KIAA gene (KIAA1199) previously reported in the HUGE (Human Unidentified Gene-Encoded Large Proteins) database. Previous publication(s) have disclosed that KIAA1199 upregulation is associated with cellular mortality, which is not directly related to cancer (Cancer Letters 239(1): 71-77 (2006)), herein incorporated by reference. Matsuzaki et al. Ann. Surg. Oncol (2009) 16:2042-2051 disclose KIAA1199 overexpression.

PCR Subtraction Hybridization is a widely used method for separating DNA molecules that distinguish two closely related DNA samples. This method is based on a suppression PCR effect that combines normalization and subtraction in a single procedure. The normalization step equalizes the abundance of DNA fragments within the target population, while the subtraction step excludes sequences that are common to the populations being compared. This dramatically increases the probability of obtaining low-abundance differentially expressed cDNA fragments. Full-length genes can then be isolated by means of RACE (Rapid Amplification of cDNA Ends) cDNA amplification or cDNA library screening. The PCR-Subtraction Hybridization protocol was performed according to the manufacturer's instruction (Clontech, Protocol #PT 1117-1).

Example II

Mining DNA Microarray Databases

Tissue RNA and DNA microarray database mining demonstrate that C43 expression is normally limited to the central nervous system and lymph nodes. Upregulation of C43 in human cancer tissues was found to correlate with cancer grade, cancer stage and cancer recurrence. Examination of human cancer cell lines demonstrated that C43 is highly expressed in various disseminated carcinoma cell lines compared to less aggressive counterparts.

The large volume of gene expression profile data publicly available through GEO/NCBI and other cancer profiling databases (e.g. Oncomine; http://www.oncomine.org/main/mainx.jsp), herein incorporated by reference, has resulted in the use of data mining as an increasingly valuable tool in mainstream cancer research. Microarray data mining involves the following steps: 1) accessing a microarray database, from for example Oncomine; 2) entering a search term, e.g. KIAA1199; 3) setting the threshold value, for example $p \leq 0.01$; 4) obtaining the microarray data; and 4) performing statistical analysis, (for example the GraphPad Prism 4 software). By mining DNA microarray databases for C43 (KIAA1199) expression in human specimens (both normal and cancerous) employing a cut-off of $p \leq 0.01$, an upregulation of C43 was identified in cancer tissues as compared with adjacent normal prostate tissue in two microarray data sets.

Example III

C43 Immunohistochemistry

The following immunohistochemical protocol was used analysis of tissue sections: 1) Mouse tumors are harvested by excising the entire tumor, followed by immersion in 4% paraformaldehyde; 2) the fixed tumors are embedded in paraffin; 3) paraffin sections of approximately 5 μm thickness are prepared and mounted onto glass slides; 4) the tissue sections are rehydrated via 10 minutes of each of the following in successive order: a) Xylene, b) Xylene, c) 100% ethanol, d) 90% ethanol, e) 80% ethanol, f) 70%, g) 50% ethanol, h) Water, and i) TBS; 5) the tissue sections are immersed in 0.01 M sodium citrate, pH 4.0 at 100° C. for 15 minutes in a beaker, with the temperature monitored with a thermometer. Tissue sections are then removed and allowed to cool in TBS (0.025M Tris, 150 mM NaCl, pH 7.2); 6) endogenous peroxidase is quenched with 0.3% $H_2O_2$ for 30 minutes; 7) tissue sections are blocked with TNB buffer blocking solution (Perkin-Elmer TSA Plus DNP HRP system kit, herein incorporated by reference) for 30 minutes at room temperature; 8) tissue sections are incubated with rabbit anti-C43 antibody at 1:25 dilution in TNB solution (Perkin-Elmer TSA Plus kit) overnight at 4° C. or 2 hours at room temp; 9) tissue sections are washed 3× for 10 minutes each in TNT buffer (Perkin-Elmer TSA Plus kit) with agitation using a stir bar in the staining jar over a stir plate; 10) tissue sections are incubated in TSA amplification mixture, consisting of diluting TSA Stock in the 1× Plus amplification diluent, for 3-10 minutes at room temperature; 11) tissue sections are incubated with anti-DNT-HRP (Perkin-Elmer TSA Plus kit) at 1:100 dilution in TNB buffer for 30 minutes at room temperature; 12) tissue sections are washed 3× for 10 minutes each in TNT buffer (Perkin-Elmer TSA Plus Kit) with agitation using a stir bar in the staining jar over a stir plate; 13) tissue sections are covered with ImmPACT DAB (Vector Laboratories) for 3-5 minutes, followed by rinsing with $dH_2O$ from a spray bottle; 14) tissue sections are immersed in a solution of hematoxylin (Hematoxylin QS; Vector Laboratories) for 45 seconds; followed by rinsing with $dH_2O$ from a spray bottle; 15) tissue sections are dehydrated by repeating step 4 (above) in reverse order; and 16) tissue sections are mounted in Permount mounting solution.

Example IV

Preliminary Studies

The most life-threatening aspect of cancer is metastasis. Steps in this disseminated process include cell migration and invasion of tumor cells into the vasculature and surrounding matrices. Evidence suggests that at the time of diagnosis a high proportion of patients already have micrometastasis. There is a pressing need to identify mechanisms responsible for the metastatic process. C43 appears to play a central role in breast cancer progression. Development of inhibitory drugs to counteract C43 will provide a new approach to treat cancer. Low levels expression of C43 in non-malignant cells suggests that anti-C43 treatment strategies will provide a safe treatment to prevent progression to disseminated cancer.

Preliminary analysis of C43 demonstrated that: 1) the C43 gene is highly expressed in various disseminated carcinoma cell lines as compared to less aggressive counterparts; 2) downregulation of the C43 gene in human MDA-MB-231, and MDA-MB-435 breast cancer cells using a short hairpin RNA (shRNA) results in inhibition of cancer cell migration and invasion; 3) overexpression of the C43 gene in COS-1 cells (monkey kidney epithelial cells) or less aggressive human MCF-7 breast cancer cells enhances cell migration and cell invasion; 4) knockdown of C43 in MDA-MB-435 cells induces a morphologic transition from fibroblast-like to epithelial-like cells (MET-epithelial to mesenchymal transformation) consistent with reversal of the metastatic phenotype; 5) C43 is involved in endoplasmic stress (i.e. hypoxia); and 6) inhibition of endogenous C43 in the highly invasive prostate cancer PC3 cells decreases cell migration. In addition, C43 overexpression does not alter in vitro cell growth or colony formation in agar, thus indicating that C43 does not function via a cell proliferation mechanism. Based on these data, C43 is proposed to play an important role in cancer cell migration, invasion, and metastasis. Based on these observations, C43 potentially represents a powerful therapeutic target for treating breast cancer.

Data demonstrate that C43 plays an important role in cancer dissemination and represents a potential therapeutic target for preventing cancer invasion and metastasis. C43 overexpression in non-malignant COS-1 cells or weakly aggressive human MCF-7 breast cancer cells significantly enhanced cell migration. C43 downregulation in human breast cancer MDA-MB-435 cells using short hairpin RNA (shRNA) inhibits cancer cell migration and invasion in Transwell Chamber migration assays and 3D type-I collagen gel invasion assays. Knockdown of C43 levels in MDA-MB-435 cells induces a morphologic transition from fibroblast-like to epithelial-like cells, suggesting that C43 plays a role in the cascade of epithelial-to-mesenchymal transition (EMT).

It is further demonstrated that shRNA mediated downregulation of C43 in orthotopically implanted MDA-MB-435 cells results in delayed tumor appearance, progression, and prolonged survival in immunodeficient mice as compared to luciferase shRNA controls. C43 specific antibody demonstrates that C43 distribution is limited to the endoplasmic reticulum, suggesting a role as a molecular chaperone involved in regulating the cell migratory cascade.

Figure 1:
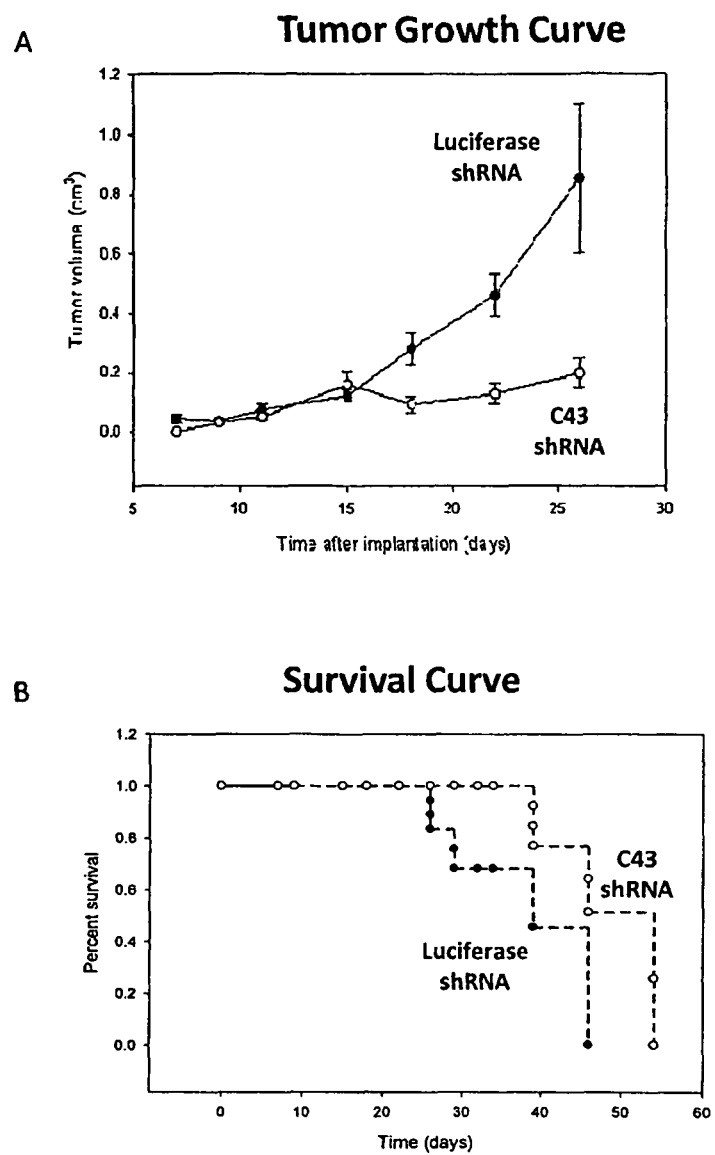
FIG. 1 depicts tumor growth and survival curves comparing the effect of C43 shRNA (SEQ ID NO: 2) (FIG. 1A) and control luciferase shRNA (FIG. 1B) on tumor appearance, progression, and survival following orthotopic implantation of MDA-MB-435 breast cancer cells into immunodeficient mice.
Figure 5:
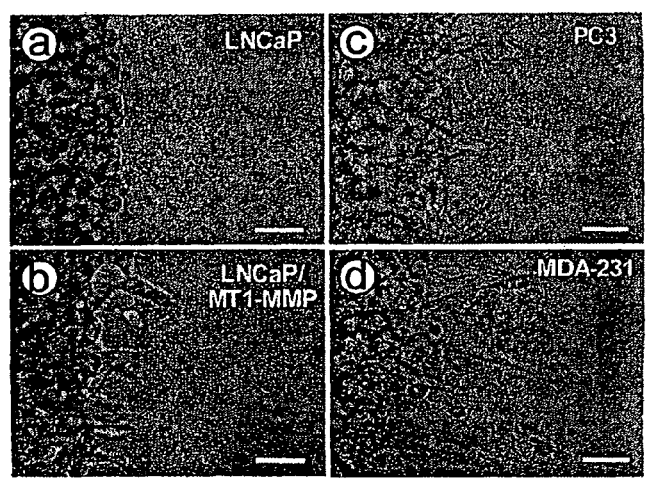
FIG. 5 depicts the evaluation of the invasive ability of cancer cells using the 3D invasion assay.

As summarized in FIG. 1, $2 \times 10^6$ MDA-MB-435 cancer cells expressing either C43 shRNA or luciferase shRNA control were orthotopically injected into mammary tissue of nu/nu immunodeficient mice. Tumor growth was measured with calipers twice a week. Tumor size was determined using the formula: (tumor size=tumor diameter(×)square root of tumor diameter(÷)2). Downregulation of C43 with shRNA in MDA-MB-435 infected cells resulted in delayed tumor appearance and progression (FIG. 1A) and prolonged survival (FIG. 1B) as compared to luciferase shRNA control mice. In contrast to in vivo tumor growth, downregulation of C43 had no effect on cancer MDA-MB-435 cell proliferation in tissue culture (not shown), emphasizing the unique role of C43 on protease-independent aspects of cell invasion and tumor progression.

I. shRNA Synthesis

Small interfering oligonucleotides specific for either C43 or luciferase (control) to express short hairpin RNA (shRNA) were designed using an online software system (Block-iT RNAi Designer; Invitrogen) for mammalian RNA interference. Specific 21-nucleotide sequences spanning nucleotides 1735-1757 of the human C43 gene (see FIG. 2: SEQ ID NO: 1) and nucleotides 103-123 of luciferase from firefly *Pyrocoelia pectoralis* as a control were synthesized by Operon Biotechnologies, Inc. Annealed double stranded oligonucleotides were cloned into the RNAi-Ready pSIREN-Retra Q vector (Clontech). A retroviral supernatant was obtained by co-transfection of a vector encoding the envelope gene (pAmphotropic) and the retroviral expression vector containing the C43 shRNA, or luciferase shRNA control into human embryonic kidney GP2-293 packaging cells (Clontech) according to the manufacturer's protocol. MDA-MB-435 cells were infected with the viral supernatant, and the cells were then selected with 4 µg/ml puromycin for 1-2 weeks. The shRNA's effect on gene expression was evaluated by real time RT-PCR using RNA of pooled resistant cells.

II. Method(s) of Identifying ER Localization:

To determine the subcellular distribution of C43, an immunofluorescent staining approach (as described previously) was employed using antibodies against distinct cellular markers. COS-1 cells transfected with C43 cDNA were incubated with anti C43 antibodies along with antibodies for an ER marker protein (Calreticulin), a trans-Golgi network marker protein (TGN38), an early endosome marker protein (early endosome antigen 1, EEA1), a late endosome marker protein (Cation Independent mannose-6-phosphate receptor, CI-MPR), and a cell surface marker protein (transferrin receptor). Subcellular distribution of C43 protein was determined by a confocal fluorescent microscopy (Zeiss LSM 510 META NLO Two-Photon Laser Scanning Confocal Microscope System). C43 gene product was c-localized with the ER marker protein, calreticulin, suggesting C43 protein is ER resident protein. To further confirm the ER subcellular distribution of C43, COS-1 cells were sequentially infected with the ER marker protein, calreticulin fused with orange fluorescent protein (OFP) (Invitrogen) cDNA, and transfected with C43-GFP chimeric cDNA. Distribution of C43-GFP and ER-OFP in COS-1 cells was observed under confocal microscopy. Co-localization (yellow) of C43 with the ER marker is determined by superimposition of green and red-labeled proteins. 83% of C43 protein was co-localized with ER marker calreticulin (ER-OFP) in the transfected cells using Zeiss LSM 510 Meta software analysis (Co-localization Function Measurement).

Example V

In Vitro Assay of Cancer Invasion: Detection of Anti-Cancer Drugs

The following methodology permits the detection of cancer cell invasion into a collagen matrix and the inhibitory activity of anti-cancer drugs. This assay is useful in identifying pharmacologic agents (drugs) that interfere with cancer progression. The assay consists of adding and mixing cancer cells ($1-4\times10^7$/ml) in a solution containing type I collagen (final concentration of collagen: 1.5 mg/ml) and carefully placing a drop (1 microliter) of the solution on the plastic (hydrophobic) surface of a 96-well non-tissue culture plate. After the collagen solidifies at 37° C., a second layer of collagen is placed over the gelled droplet. This produces is a 3-dimensional (3D) matrix with a clear region surrounding the original cancer cell droplet that may be examined using microscopy. The matrix is then covered in culture medium along with pharmacologic agents (drugs, nutraceuticals, small molecules etc.). In some cases, the cancer cells have been previously transfected with green fluorescent protein (GFP) cDNA to permit rapid visualization of cancer invasion of the collagen matrix and to permit automation of the technique. Invading cancer cells leaving the perimeter of the original collagen droplet are readily visualized extending into the surrounding collagen matrix after 18 h incubation. Both qualitative and quantitative analyses are performed microscopically. The invasive ability of cancer cells (cells outside the original droplet), as well as the effect of pharmacologic agents on the cancer cell invasion, can be determined microscopically. The effect of pharmacologic agents on invasion of cancer cells is determined by counting invading cells in the presence versus the absence of pharmacologic agents. Inhibition of in vitro cancer invasion identifies drugs that have the potential to be useful in cancer treatment. This assay will be readily adaptable for high throughput screening of libraries of compounds that may be useful for cancer treatment. This assay is also useful for identifying drugs capable of interfering with invasion of other cell types such as endothelial cells, nerve cells, etc. In addition, this assay provides a rapid, convenient, and reliable approach to evaluate cancer invasion-related genes or anti-metastasis-related genes.

The advantage of this technology is that it permits high throughput screening of large numbers of pharmaceutical agents for their ability to inhibit cancer invasion in a 3D format. The 3D assay is more relevant to in vivo invasion than previously described 2-dimensional (2D) technology. This 3D assay can be adapted for rapid screening of large libraries of compounds. Agents identified in this assay will then be useful for testing as anti-invasive and anti-metastatic drugs.

I. Clinical Significance

Cell migration and invasion are critical aspects of cancer metastasis that account for 90% of treatment failures in cancer (Hanahan et al., Cell 100, 57-70 (2000)), herein incorporated by reference). Conversion of epithelial cancer cells to a mesenchymal-like phenotype (epithelial-to-mesenchymal transition, EMT) often occurs during the early stages of cancer and results in enhanced cancer cell migration and invasion (Thiery et al., Nat. Rev. Cancer 2, 442-454 (2002)), herein incorporated by reference. Therefore, targeting early stage cancer cell migration/invasion holds considerable promise in cancer treatment. Despite considerable efforts, drug development programs targeting metastasis have lagged behind those targeting tumor growth. Rational drug design based on selective targeting of single cancer progression pathways has had limited effectiveness for most types of cancers. There is, therefore, a pressing need for novel strategies in cancer drug discovery.

Target specificity and selectivity are of critical importance in developing new treatments for cancer. Many solid cancers escape drug targeting of a specific pathway by utilizing alternative pathways (Dancey et al., Nat. Rev. Drug Discov. 5, 649-659 (2006)), herein incorporated by reference. Phenotypic screening for new inhibitors has the potential to circumvent this problem by performing unbiased testing of compounds in cells (i.e. without knowing the exact pathway/target of the compound) and assaying for the desired cellular effect. Both target specific and phenotypic screening require high throughput screening (HTS) methods in order to accelerate drug discovery. Chemical based HTS approaches which measure chemical interactions between a candidate compound and a selected target molecule such as a receptor or kinase can screen compounds at high speed, but provide no information about the biological responses of cells. As a result, a large number of potential drug candidates fail in the later stages of drug development due to lack of biological efficacy, unfavorable pharmacokinetic properties, and toxicity. Although more complex than cell-free biochemical test systems, HTS assays using two-dimensional (2D) cultured cells still reflect a highly artificial cellular environment, display limited reproducibility, and may thus have limited predictive value for the clinical efficacy of a compound in cancer. Drug discovery programs require simple, HTS-amenable testing systems that mimic the human tissue environment in order to optimize preclinical study of the most active molecules from a large pool of potential effectors.

Three-dimensional (3D) cultured cancer cells have been demonstrated to display gene expression patterns similar to in vivo tumors using DNA microarray technology and better reflect the in vivo behavior of most cell types than 2D cultured cells (Capdeville et al., Nat. Rev. Drug Discov. 1, 493-502 (2002)), herein incorporated by reference. However, these 3D systems have not yet been incorporated into mainstream drug development programs due to the lack of simple, reproducible techniques and protocols for rapid, standardized assays of cellular responses in vitro.

Preliminary data now demonstrate an assay for quantitative evaluation of cancer cell migration/invasion in a 3D matrix that is simple, precise and easy to replicate. This assay allows simultaneous observation of cell migration, cell invasion and cell death using image-based analysis, and may be converted into a fully automated high-throughput 3D invasion assay to accelerate anti-cancer drug discovery for treatment/prevention of metastasis. To date, 3D culture systems including multicellular spheroids, multi-layer matrix-embedded cellular cultures, hollow-fiber bioreactors, and ex vivo cultures have been utilized in basic and applied tumor biology.

II. Preliminary Evidence/Feasibility

The overall goal of this proposal is to develop a HTS 3D invasion assay for anti-cancer drug development. As such, the following have been established: 1) a 3D assay for evaluating cancer cell migration/invasion (cancer cells embedded in type I collagen gel); 2) a prototype assay plate (96-well) for scaled-up compound screening; and 3) an automated microscopy and cell imaging analysis system for data readout. Experiments performed to accomplish these tasks are described below.

a). 3D Invasion Assay for Evaluating Cancer Cell Migration/Invasion

Multicellular spheroids, the most commonly used 3D cell culture system, have been previously proposed as a drug-screening tool (Schughart et al., J. Biomol. Screen. 9, 273-285 (2004)), herein incorporated by reference. However, HTS using the multicellular spheroid assay is hampered by a lack of standardized and rapid procedures. Recognizing the potential of a 3D drug discovery assay, a simple and rapid 3D cell invasion assay has been developed that involves: 1) "gluing" cancer cells within a matrix, 2) dotting the cell/matrix mixture into a 96-well plate; 3) embedding the cell aggregate in the matrix, and 4) assessing cell migration/invasion into the surrounding matrix using an imaging analysis tool. Due to rapid solidification of the matrix, cancer cell aggregates are formed within 15 min at 37° C. as compared to multicellular spheroid formation that requires 7 days in culture.

Figure 6:
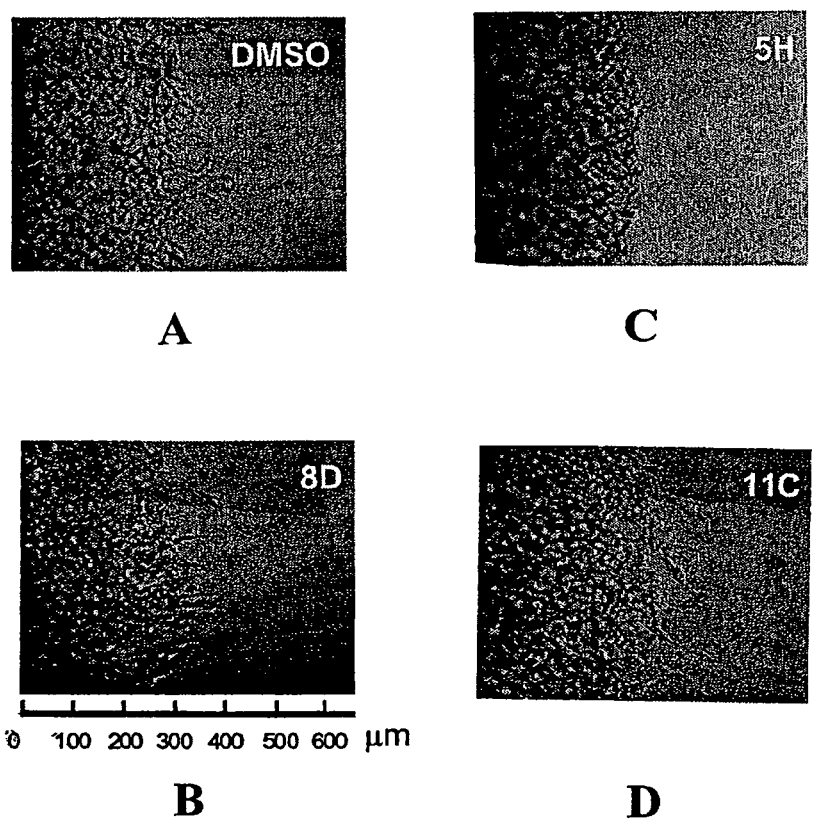
FIG. 6 depicts the screening of the NCI compound library for preventing MT1-MMP induced prostate cancer cell invasion.
Figure 7:
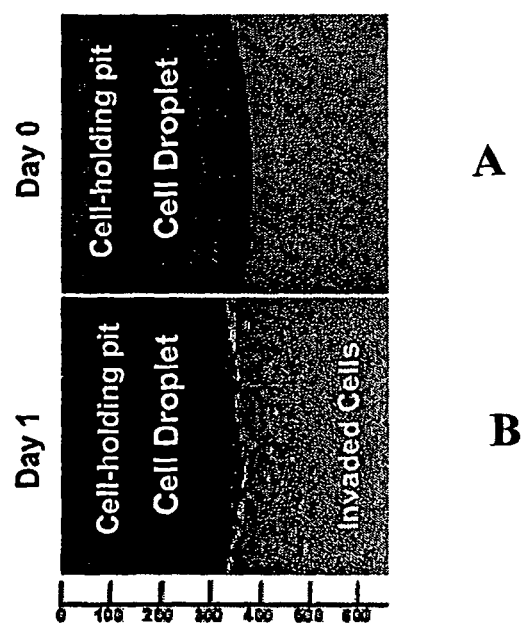
FIG. 7 depicts the standardized 3D invasion assay.

This assay has been used to evaluate cancer cell migration/invasion using an invasive human breast cancer cell line (MDA-MB-231 cells), an invasive prostate cancer cell line (PC3 cells), a non-invasive prostate cancer cell line (LNCaP cells) and LNCaP cells expressing membrane type 1-matrix metalloproteinase (MT1-MMP), a membrane bound protease which enhances cell invasive ability. This assay demonstrates that LNCaP cells expressing MT1-MMP (FIG. 5B), PC3 cells (FIG. 5C) and MDA-MB-231 cells (FIG. 5D) are able to gradually invade the surrounding matrix, while no invasion into the surrounding matrix is observed with the non-transfected LNCaP cells (FIG. 5A) after an 18-hour incubation. This study indicates potential applications for this assay including: 1) screening a small molecule compound library to identify novel candidates for prevention of cancer cell migration/invasion (FIG. 6); 2) screening an antibody library for identification of inhibitory antibodies; 3) validating selected compounds identified in chemical-based screening; 4) determining the effect of selected compounds on different types of cancers; 5) studying genes involved in cancer invasion; and 6) screening a compound library against cell migration in other disease-related studies, e.g. macrophage migration in atherosclerosis. As demonstrated by FIG. 6, compound 5H/4130/23 completely blocks LNCaP cells expressing MT1-MMP-induced cell invasion (FIG. 6C), whereas other compounds had no effect on cell invasion (FIGS. 6 A, B and D).

b) Prototype of Invasive Plate for Standardization of the Invasion Assay

To increase the throughput and to standardize and automate the readout using imaging software, a 96-well prototype plate with a 1 mm$^3$ pit in the center of each well has been designed. IBC human prostate cancer cells were loaded into a 96-well plate with a tooled pit at the center in each well. Cells were covered with type I collagen gel (FIG. 7A) and incubated for 24 hours (FIG. 7B). Following fixation, cells that migrated outside of the pit were captured and counted manually. This 96-well plate restricts the cell/matrix mixture to an identical size and location within each well, thus permitting automated microscopic imaging of cell invasion.

c) Automated Analysis of Cell Invasion

Figure 8:
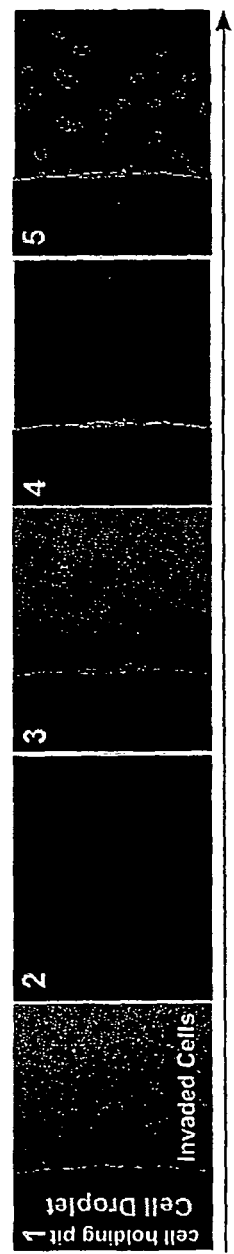
FIG. 8 depicts the steps used to analyze invaded cells using the 3D invasion assay and the Nikon NIS Elements imaging software.

A motorized stage (Prior Scientific, Inc.) has been adapted to a Nikon TE2000s inverted microscope. Image acquisition and data analysis is performed using the automated microscopy system controlled by NIS-Elements imaging software (Nikon). It takes 6 minutes to scan an entire 96 well plate using a 10× objective. To quantitatively analyze cells that invade into the matrix, both phase contrast and nuclear-stained images are required. Preliminary data indicate that automated quantification of invading cancer cells can be accomplished in the invasion assay using the 96-well plates and an automated microscopy imaging system. The steps (1-5) used to analyze invaded cells using the Nikon NIS Elements imaging software are shown in FIG. 8. HT1080 cells were evaluated using the 3D invasion assay. After 18 h incubation, the cells were fixed and permeabilized. DAPI staining was then performed. The plate was placed in a motorized stage and both phase contrast and fluorescent images were acquired using a Nikon TE-2000s controlled by NIS Elements imaging software (FIG. 8, steps 1 and 2). Invaded cells (those outside of a cell hold pit) in the first well the 96-well plate were defined by adjusting thresholds from the phase contrast image to create a binary (FIG. 8, step 3). The defined binary was applied to the DAPI image (FIG. 8, step 4) and invaded cells were then automatically counted (FIG. 8, step 5). The invaded cells in the remaining wells were determined based on the given threshold. A flow chart (FIG. 9) illustrates the steps involved in the 3D invasion assay.

Using 12 aggressive cancer cell lines and 5 non-aggressive cancer cell lines transfected with various oncogene/metastasis genes the 3D invasion assay proved highly reproducible and efficient in detecting compounds capable of inhibiting cell invasion and in characterizing genes capable of inducing cell invasion (data not shown). In some embodiments, a liquid handling system and an automated microscopy system is incorporated into the 3D invasion assay to build a novel HTS screening pipeline for anti-cancer invasion drug screening.

III. Experimental Design & Methods

Drug development programs targeting metastasis have lagged behind those targeting tumor growth (Lang et al., Recent Patents on Anti-Cancer Drug Discovery 1, 69-80 (2006)), herein incorporated by reference. One reason for this lag is the lack of simple, controlled techniques and protocols for rapid, standardized HTS of cellular responses in vitro (Schughart et al., J. Biomol. Screen. 9, 273-285 (2004)), herein incorporated by reference. The HTS 3D invasion assay may be validated by screening the NCI diversity compound library targeting invasive cancer cells.

a) Converting the 3D Invasion Assay into an Automated Image-Based HTS Drug Discovery Assay The automated HTP 3D invasion system includes: 1) automated tissue culture incubators; 2) liquid handling/dispensing system for dotting cancer cells, overlaying with type I collagen, and adding test samples; 3) automated imaging acquisition; and 4) automated data analysis. The fully automated 3D screening system will expedite novel anti-cancer drug discovery.

Standardization (e.g. size and position of cell aggregates) is important for automated imaging acquisition and data analysis. A computer-guided drilling system is employed to produce invasion plates with standardized cell holding wells fitted into a 96-well plate.

Advanced liquid handling technologies have made sample management systems more reliable and integration-ready. Modules are available that can maintain a warm temperature to serve as an incubator, or with cooling mechanisms to keep the plates at refrigerator-like temperatures. In recent years, technologies have improved to allow reliable and consistent automated pipetting for the dispensing of volumes as low as 1 ul.

HT1080 cells and/or human breast cancer MDA-MB-231 cells ($4 \times 10^7$/ml) mixed with type I collagen (1.5 mg/ml at final) are dispensed into the cell-holding wells in invasion assay plates (2 ul/well, optimum volume) using the liquid handling system at 4° C. working temperature to prevent the collagen from solidifying within the liquid handling system. After dotting, the plate is inserted in an incubator chamber at 37° C. for 15 min followed by the addition of type I collagen to cover the gelled cell aggregates. Following solidification of the gel overlay, culture medium containing positive (e.g. anti-β1 integrin antibody, MAPK inhibitor PD98059, etc. which block HT1080 and/or human breast cancer MDA-MB-231 cell invasion) and negative controls (vehicle only) is added and incubated for 24 hours. The cells are then fixed and permeabilized with 4% PFA/0.2% Triton X-100/PBS for 30 min, and incubated with a nuclear staining buffer (100 nM DAPI/PBS) for 30 min. The plate is then placed on an automated microscopy stage for image acquisition. Images are acquired from transmission (phase contrast) and fluorescence (DAPI) sources by an external light shutter device that gathers two images per time point in time-lapse sequences. Preliminary observations indicate that 12 minutes will be required to scan one 96-well plate for cell invasion. Data analysis will be performed using NIS-Element imaging software (Nikon) based on pre-determined criteria.

b) Validation of the Automated HTS 3D Invasion Assay by Screening the NCI Diversity Compound Library Targeting Invasive Cancer Cells An NCI compound library containing 1990 diverse compounds will be screened using the automated HTP 3D invasion system to target cell migration/invasion. The results of this screen are expected to identify multiple compounds that effectively inhibit cancer dissemination.

The following steps will be performed to screen the compound library targeting cancer cell migration/invasion using the automated 3D invasion HTS system: 1) Cell plating: HT1080 cells and/or human breast cancer MDA-MB-231 cells are used for selecting inhibitory compounds because these cells display invasive ability and represent mesenchymal cancer cells. HT1080 cells and/or human breast cancer MDA-MB-231 cells ($8 \times 10^4$/well) mixed with type I collagen gel are dotted into the specialized 96-well plate using an automated liquid handling system. After the gel solidifies, cell clumps will be covered with collagen gel, 2) Compound exposure: The NCI compound library contains 1990 diverse compounds covering a broad display of pharmacophores derived from 140,000 compounds. For the phenotypic screening, compounds (10 μM final concentration) are added to cell-holding wells at a final dimethyl sulfoxide (DMSO) concentration of 0.1% (non-toxic), and 3) Plate readout: After a 24-hour incubation the cells are fixed, permeabilized, and stained with DAPI. Images acquired by an automated Nikon inverted microscope (TE2000s) equipped with a motorized stage (Prior Scientific) are then analyzed using the NIS-Elements software (Nikon). Invading cells are then automatically and quantitatively identified. Positive and negative controls will be included on each 96-well plate to provide clear functional plate pass/fail criteria. Using positive controls (20 μM MAPK inhibitor PD98059 and 5 μg/ml anti-β1 integrin antibody) and a negative control for HT1080 cells and/or human breast cancer MDA-MB-231 cells, the approach of Zhang et al. (Zhang et al. J. Biomol. Screen. 4, 67-73 (1999)), herein incorporated by reference, is used to test signal windows of the 3D invasion assay; a Z-factor of 0.525 is obtained, consistent with an excellent assay for HTS. A 50% inhibition of cell migration/invasion will initially be used as the threshold to detect inhibitory compounds (~0.5% of selected library) using this HTP 3D invasion assay. If few inhibitors are identified, compounds in the 30-50% inhibitory range will then be considered.

Selected inhibitors that induce cytotoxicity will be eliminated using a Cellular Cytotoxicity Assay Kit (Oxford Biomedical Research). The rest of the compounds in the selected library will be tested for dose-dependent inhibition of cell migration/invasion. Structural modification of selected compound will be performed to enhance solubility, efficacy and pharmacokinetics.

Tumor xenografts will be produced by subcutaneous injection of HT1080 cells and/or human breast cancer MDA-MB-231 cells in immunodeficient mice to determine the in vivo effectiveness of selected compounds on cancer development. The effect of the selected compounds on cancer invasion/metastasis will be examined by administering selected and modified inhibitory compound(s) to cancer-bearing mice. The compound(s) will be administered to mice by intravenous injection, initially at a dose of ~20 mg/kg twice a week; subsequent doses will be determined based on pilot studies. The half-life, toxicity, and stability of the inhibitory compound(s) in mice will be determined as previously described (Williams et al., PNAS 104, 2074-2079 (2007)), herein incorporated by reference. Pathological examination will then be performed to characterize invasion and metastasis.

Example VII

Hypomethylation of CpG Island Spanning the 5' End of the Regulatory Region of C43 Gene in Aggressive Cancers DNA methylation plays critical rules in the control of gene expression and the architecture of the nucleus of the cell. One of the hallmarks of cancer is abnormal methylation patterns with malignancies generally governed by widespread DNA hypomethylation (a decrease in the epigenetic methylation of cytosine residues in DNA) of tumor-promoting genes along with site-specific DNA hypermethylation (an increase in the epigenetic methylation of cytosine residues in DNA) of tumor suppressor genes. We found that the expression of C43 is correlated with aggressiveness of cancer cell lines and tissues. This observation led us to hypothesize that if hypomethylation is a common mechanism for activation of C43 genes in aggressive cancers, then demethylation inhibitors would suppress the C43 expression leading to reduced migration and invasive capacity of cancer cells.

By analyzing C43 gene in genome using the UCSC Genome Browser data at genome.ucsd.edu, we identified a potential CpG-rich island (#157) spanning the transcription start site (+1) of C43 gene from the 81,071,268 to 81,073,220 within chromosome 15.

To determine the methylation status of C43 gene in cancer cell lines including highly and minimally invasive breast cancer cell lines, we developed a methylation specific PCR assay using methylation- and non-methylation-specific primers. A pair of human breast cancer cell lines, MCF-7 (minimally invasive) and MDA-MB-231 (highly invasive), which displays a low and high expression of C43 gene, respectively, was employed. By the methylation specific PCR assay, we found that the promoter region of C43 gene was highly methylated in MCF-7 cells, but not in MDA-MB-231 cells. In addition, sequencing of bisulfate-modified DNA showed that one of the CpG rich regions within the CpG island 157 of the 5' UTR of the C43 gene was highly methylated in minimally invasive breast cancer MCF-7 cells compared to highly invasive breast cancer MDA-MB-231 cells, confirming the methylation specific PCR result. To further confirm these observations, another pair of primary cultured cells, Human Umbilical Vein Endothelial Cells (HUVEC) and human foreskin fibroblast (HFF) was analyzed using the same strategy. Hypermethylation was found in low C43 expression HUVEC and hypomethylation was found in high C43 expression HFF cells. Altogether, these results showed that demethylation of the C43 gene promote the induction of C43 in cells leading to enhanced cell migration and invasion.

Figure 16:
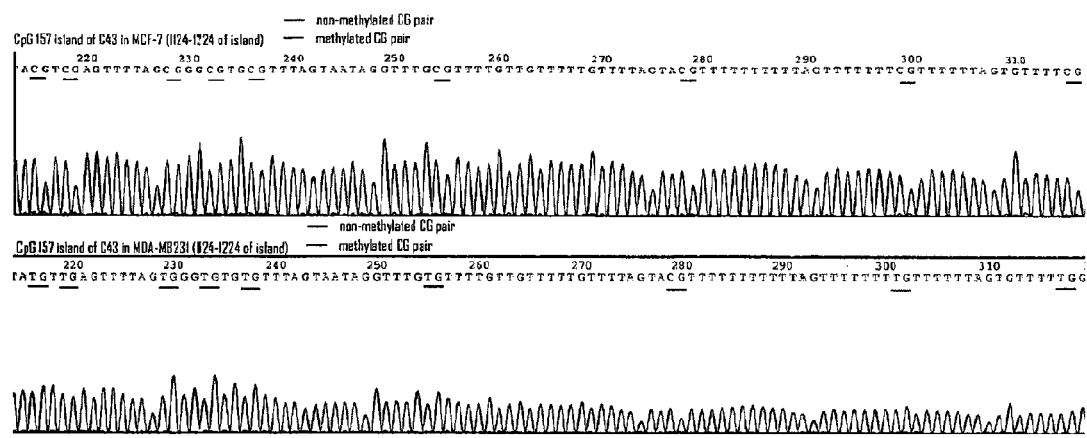
FIG. 16 shows determination of the methylation status of CpG sites by sequencing of bisulfate-modified DNA. Chromosomal DNA from MCF-7 cells and MDA-MB-231 cells were treated with bisulfate followed by PCR amplification of putative CpG island of C43 (from 81,072,237 to 81,072,771 in chromosome 15). The PCR product was purified and sequenced. Sequencing of the bisulfate-modified DNA showed that one of the CpG rich regions within the CpG island 157 of the 5' UTR of the C43 gene was highly methylated in minimally invasive breast cancer MCF-7 cells compared to highly invasive breast cancer MDA-MB-231 cells.
Figure 18:
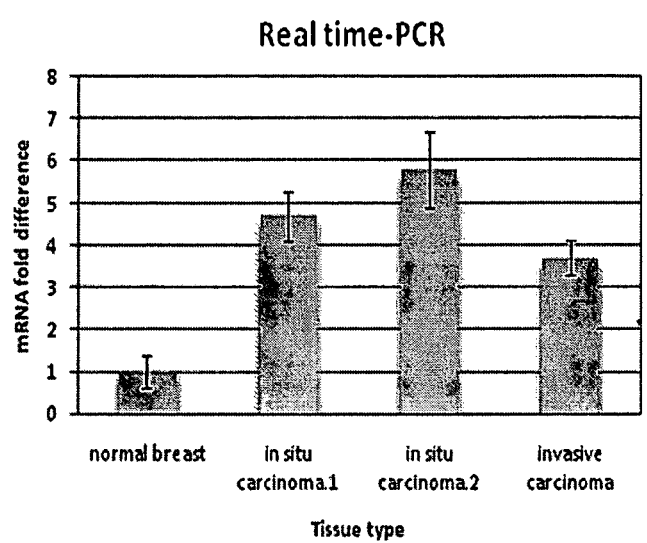
FIG. 18 shows expression of C43 in human breast cancer specimens. To determine the correlation of C43 expression with breast cancers, cancer cells from breast ductal carcinoma in situ and invasive ductal carcinoma were isolated from paraffin embedded HE stained breast cancer specimens using a laser capture microdissection technique. Non-neoplastic breast epithelium (epithelial cells without contamination with stromal cells) were also isolated from normal tissues as a control. Total RNA was extracted and amplified followed by a real time RT PCR analysis using specific primers of C43. House keeping genes were used as an endogenous control. Initial studies indicate that the C43 gene is increased 5-6 fold in breast cancer cells compared to normal breast cells.

Data discussed in Example VII is illustrated by FIGS. 16-18

Example VIII

Cell Invasion Assay Using a 3-Dimensional Matrix

To increase the throughput as well as to standardize and automate the readout using imaging software, we have designed and tooled a 96-well plate with a 2.1 mm3 pit in the center of each well. This tooled plate restricts the cell/matrix mixture to an identical pit (size and location) within each well, thus permitting automated microscopic imaging of cell invasion (FIG. 19). To test if imaging acquisition and data analysis can be automated, we have employed a motorized stage (Prior Scientific, Inc.) installed on the existing Nikon TE2000s inverted microscope. The automated microscopy system is controlled by the NIS-Elements imaging software (Nikon) for imaging acquisition and data analysis. Using a 10× objective, we have shown that it takes 6 minutes to scan the entire 96 well plate. To quantitatively analyze cells that invade into the matrix, using both phase contrast and nuclear-stained images is optimal. Our preliminary data indicate that automated quantification of invading cancer cells can be accomplished in the invasion assay employing the tooled plates and automated microscopy imaging system (FIG. 19).

To establish the efficacy of the assay for screening libraries, we have tested the effect of well-established inhibitory compounds on cell invasion. Using human breast cancer MDA-MB-231 cells, we demonstrated dose-dependent inhibition of cell invasion by anti-β1 integrin antibodies and a MAPK inhibitor (PD98059) (data not shown). The results of this study demonstrated that this 3D invasion assay is highly effective in detecting compounds capable of inhibiting cell invasion. Moreover, this 3D invasion assay is simple, precise, easy to replicate, and has multiple applications.

Example IX

The 3-Dimensional Invasion Assays Identifies Cancer Cell Invasion and/or Metastasis Genes To study the genes enhancing cancer cell invasion, minimally invasive breast cancer MCF-7 cells and minimally invasive prostate Cancer LNCaP cells were separately and stably transfected with Membrane type 1-matrix metalloproteinase (MT1-MMP) and C43, followed by determining cell migration of the transfected cells in the herein described 3-dimensional invasion assay. Overexpression of these genes significantly promoted cell invasive ability. Therefore, this novel 3D invasion assay can be used to evaluate genes involving cancer invasion. In another embodiment, using highly invasive cancer cell lines, this assay can be also used to evaluate anti-metastasis genes.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiment, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

I claim:

1. A multi-well platform comprising a plurality of wells, wherein said plurality of wells is a multiple of 96, and wherein
   a) at least one well is a 3-dimensional well that has a bottom surface that comprises a second well, and
   b) said second well
      i) has a bottom surface that is continuous with said bottom surface of said at least one well, and is below said bottom surface of said at least one well, and
      ii) comprises a 3-dimensional matrix that
         1) contains cells, and
         2) comprises a surface that is above said bottom surface of said at least one well.

2. The multi-well platform of claim 1, wherein said plurality of wells is arranged in a two-dimensional linear array pattern.

3. The multi-well platform of claim 1, wherein said plurality of wells is from 96 wells to 9,600 wells.

4. A multi-well platform comprising a plurality of wells, wherein said plurality of wells is a multiple of 96, and wherein
   a) at least one well has a surface that comprises a second well, and
   b) said second well comprises a first 3-dimensional matrix that
      i) contains cells, and
      ii) is in contact with a second 3-dimensional matrix that is
         1) free of said cells,
         2) present on top of said first 3-dimensional matrix, and
         3) comprised within said at least one well.

5. The multi-well platform of claim 4, further comprising a fluid in contact with said second 3-dimensional matrix.

6. The multi-well platform of claim 5, wherein said fluid comprises a test compound.

7. The multi-well platform of claim 4, wherein said second well is comprised in a bottom surface of said at least one well, wherein said second well has a bottom surface, and wherein said bottom surface of said second well is below said bottom surface of said at least one well.

* * * * *